(12) United States Patent
Daines et al.

(10) Patent No.: US 7,312,212 B2
(45) Date of Patent: Dec. 25, 2007

(54) AMINOPIPERIDINE DERIVATIVES

(75) Inventors: Robert A Daines, Collegeville, PA (US); William Henry Miller, Collegeville, PA (US); Neil David Pearson, Harlow (GB); Israil Pendrak, Collegeville, PA (US); Mark Andrew Seefeld, Collegeville, PA (US)

(73) Assignee: Glaxo Group Limited, Greenford, Middlesex (GB)

( * ) Notice: Subject to any disclaimer, the term of this patent is extended or adjusted under 35 U.S.C. 154(b) by 518 days.

(21) Appl. No.: 10/502,233

(22) PCT Filed: Jan. 27, 2003

(86) PCT No.: PCT/EP03/00823

§ 371 (c)(1), (2), (4) Date: Jul. 22, 2004

(87) PCT Pub. No.: WO03/064421

PCT Pub. Date: Aug. 7, 2003

(65) Prior Publication Data

US 2005/0159411 A1 Jul. 21, 2005

(30) Foreign Application Priority Data

Jan. 29, 2002 (GB) ................. 0202026.1
Dec. 20, 2002 (GB) ................. 0229824.8

(51) Int. Cl.
*C07D 471/04* (2006.01)
*A61K 31/4375* (2006.01)

(52) U.S. Cl. ............... 514/228.2; 524/228.5; 524/230.8; 524/300; 524/312; 524/313; 524/314; 544/58.6; 544/105; 546/122; 546/153; 546/159

(58) Field of Classification Search ............... 514/312, 514/313, 314, 300, 228.2, 228.5, 230.5; 546/122, 546/153, 159; 544/58.5, 105
See application file for complete search history.

(56) References Cited

U.S. PATENT DOCUMENTS

| 5,264,431 | A | 11/1993 | Wacker et al. ........... 514/211 |
|---|---|---|---|
| 5,310,743 | A | 5/1994 | Schilling et al. ........ 514/311 |
| 5,541,195 | A | 7/1996 | Schilling et al. ........ 514/311 |
| 5,646,144 | A | 7/1997 | Schilling et al. ........ 514/241 |
| 6,403,610 | B1 | 6/2002 | Malleron et al. ........ 514/314 |
| 6,602,882 | B1 | 8/2003 | Davies et al. ........... 514/300 |
| 6,602,884 | B2 | 8/2003 | Bacque et al. .......... 514/314 |
| 6,603,005 | B2 | 8/2003 | Baque et al. ............ 546/176 |
| 6,803,369 | B1 | 10/2004 | Erskine et al. ......... 514/253.06 |
| 6,815,547 | B2 | 11/2004 | Bacque et al. .......... 546/174 |
| 6,841,562 | B2 | 1/2005 | Bacque et al. .......... 514/314 |
| 6,903,217 | B2 | 6/2005 | Bacque et al. .......... 546/180 |
| 6,911,442 | B1 | 6/2005 | Davies et al. ........... 514/230.5 |
| 6,962,917 | B2 | 11/2005 | Davies et al. ........... 514/264.1 |
| 6,989,447 | B2 | 1/2006 | Markwell et al. ........ 546/152 |
| 7,001,913 | B1 | 2/2006 | Davies et al. ........... 514/300 |
| 7,141,564 | B2 | 11/2006 | Brooks et al. .......... 514/248 |
| 7,186,730 | B2 | 3/2007 | Dartois et al. ......... 514/266.22 |
| 7,205,408 | B2 | 4/2007 | Davies et al. ........... 514/243 |
| 2003/0203917 | A1 | 10/2003 | Erskine et al. ........ 514/253.06 |
| 2004/0087619 | A1 | 5/2004 | Bacque et al. .......... 514/314 |
| 2005/0085494 | A1 | 4/2005 | Daines et al. ......... 514/266.22 |
| 2006/0014749 | A1 | 1/2006 | Davies et al. ........... 514/249 |
| 2006/0040925 | A1 | 2/2006 | Davies et al. .......... 514/222.8 |
| 2006/0040949 | A1 | 2/2006 | Surivet et al. ........ 514/253.04 |
| 2006/0041123 | A1 | 2/2006 | Axten et al. ........... 544/48 |
| 2006/0058287 | A1 | 3/2006 | Axten et al. .......... 514/224.2 |
| 2006/0116512 | A1 | 6/2006 | Axten et al. ........... 544/48 |
| 2006/0166977 | A1 | 7/2006 | Axten et al. .......... 514/224.2 |
| 2006/0189604 | A1 | 8/2006 | Axten et al. .......... 514/224.2 |
| 2007/0004710 | A1 | 1/2007 | Axten et al. .......... 514/224.2 |

FOREIGN PATENT DOCUMENTS

| BE | 772190 A1 | 1/1972 |
|---|---|---|
| CA | 2004986 A1 | 6/1990 |
| EP | 0238868 A2 | 9/1987 |
| EP | 0304493 A1 | 3/1989 |
| EP | 0374095 A2 | 6/1990 |
| EP | 0532456 A1 | 3/1993 |
| EP | 0541486 A1 | 5/1993 |
| EP | 0532456 B1 | 3/1995 |
| EP | 0823429 A1 | 2/1998 |
| EP | 1218370 B1 | 12/2004 |
| GB | 1345872 | 2/1974 |
| GB | 1537867 | 1/1979 |
| JP | 1995179407 A | 7/1995 |
| WO | WO 95/09853 | 4/1995 |

(Continued)

OTHER PUBLICATIONS

U.S. Appl. No. 11/604,045, filed Nov. 22, 2006, Brooks et al.
U.S. Appl. No. 10/868,351, filed Jun. 15, 2004, Erskine et al. Compounds and Methods for the Treatment of Disease.
U.S. Appl. No. 10/199,933, filed Jul. 19, 2002, Erskine et al. Compounds and Methods for the Treatment of Disease.
U.S. Appl. No. 10/937,468, filed Sep. 9, 2004, Erskine et al. Compounds and Methods for the Treatment of Disease.

*Primary Examiner*—Zinna N. Davis
(74) *Attorney, Agent, or Firm*—Loretta J. Sauermelch; Mary E. McCarthy; Charles M. Kinzig

(57) ABSTRACT

Piperidine derivatives and pharmaceutically acceptable derivatives thereof useful in methods of treatment of bacterial infections in mammals, particularly in man.

14 Claims, No Drawings

FOREIGN PATENT DOCUMENTS

| | | |
|---|---|---|
| WO | WO 96/15128 | 5/1996 |
| WO | WO 96/38144 | 12/1996 |
| WO | WO 97/03069 | 1/1997 |
| WO | WO 97/17957 | 5/1997 |
| WO | WO 97/28167 | 8/1997 |
| WO | WO 97/45119 | 12/1997 |
| WO | WO 98/02438 | 1/1998 |
| WO | WO 99/37635 | 7/1999 |
| WO | WO 00/21948 | 4/2000 |
| WO | WO 00/21952 | 4/2000 |
| WO | WO 00/43383 | 7/2000 |
| WO | WO 00/78748 A1 | 12/2000 |
| WO | WO 01/07432 | 2/2001 |
| WO | WO 01/07433 A2 | 2/2001 |
| WO | WO 01/25227 A2 | 4/2001 |
| WO | WO 01/087839 A1 | 11/2001 |
| WO | WO 02/08224 | 1/2002 |
| WO | WO 02/24684 A1 | 3/2002 |
| WO | WO 02/40474 A2 | 5/2002 |
| WO | WO 02/50040 A1 | 6/2002 |
| WO | WO 02/50061 A1 | 6/2002 |
| WO | WO 02/056882 | 7/2002 |
| WO | WO 02/072572 A1 | 9/2002 |
| WO | WO 02/96907 A1 | 12/2002 |
| WO | WO 03/010138 A2 | 2/2003 |
| WO | WO 03/064431 A2 | 8/2003 |
| WO | WO 03/087098 | 10/2003 |
| WO | WO 04/002490 A2 | 1/2004 |
| WO | WO 04/002992 A1 | 1/2004 |
| WO | WO 04/014361 A1 | 2/2004 |
| WO | WO 04/024712 A1 | 3/2004 |
| WO | WO 04/024713 A1 | 3/2004 |
| WO | WO 04/035569 A2 | 4/2004 |
| WO | WO 04/041210 A2 | 5/2004 |
| WO | WO 04/050036 A2 | 6/2004 |
| WO | WO 04/058144 A2 | 7/2004 |
| WO | WO 04/096982 A2 | 11/2004 |

AMINOPIPERIDINE DERIVATIVES

This invention relates to novel compounds, compositions containing them and their use as antibacterials.

WO99/37635, WO00/21948, WO00/21952, WO00/43383, WO00/78748, WO01/07432 and WO01/07433 disclose piperidine and piperazine derivatives having antibacterial activity.

We have now found a novel group of aminopiperidines which have antibacterial activity.

This invention provides a compound of formula (I) or a pharmaceutically acceptable derivative thereof:

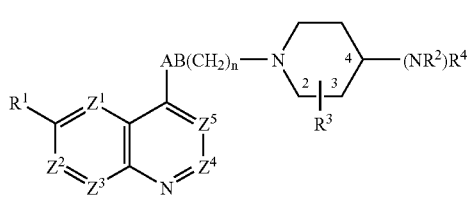

(I)

wherein:
one of $Z^1$, $Z^2$, $Z^3$, $Z^4$ and $Z^5$ is N, one is $CR^{1a}$ and the remainder are CH, or one of $Z^1$, $Z^2$, $Z^3$, $Z^4$ and $Z^5$ is $CR^{1a}$ and the remainder are CH;

$R^1$ and $R^{1a}$ are independently hydrogen; hydroxy; $(C_{1-6})$alkoxy optionally substituted by $(C_{1-6})$alkoxy, amino, piperidyl, guanidino or amidino any of which is optionally N-substituted by one or two $(C_{1-6})$alkyl, acyl or $(C_{1-6})$alkylsulphonyl groups, $CONH_2$, hydroxy, $(C_{1-6})$alkylthio, heterocyclylthio, heterocyclyloxy, arylthio, aryloxy, acylthio, acyloxy or $(C_{1-6})$alkylsulphonyloxy; $(C_{1-6})$alkoxy-substituted$(C_{1-6})$alkyl; halogen; $(C_{1-6})$alkyl; $(C_{1-6})$alkylthio; trifluoromethyl; trifluoromethoxy; nitro; azido; acyl; acyloxy; acylthio; $(C_{1-6})$alkylsulphonyl; $(C_{1-6})$alkylsulphoxide; arylsulphonyl; arylsulphoxide or an amino, piperidyl, guanidino or amidino group optionally N-substituted by one or two $(C_{1-6})$alkyl, acyl or $(C_{1-6})$alkylsulphonyl groups; or when $Z^5$ is $CR^{1a}$, $R^{1a}$ may instead be cyano, hydroxymethyl or carboxy;

or $R^1$ and $R^{1a}$ on adjacent positions may together form ethylenedioxy; provided that when none of $Z^1$, $Z^2$, $Z^3$, $Z^4$ and $Z^5$ is N, then $R^1$ is not hydrogen;

$R^2$ is hydrogen, or $(C_{1-4})$alkyl or $(C_{2-4})$alkenyl optionally substituted with 1 to 3 groups selected from:
amino optionally substituted by one or two $(C_{1-4})$alkyl groups; carboxy; $(C_{1-4})$alkoxycarbonyl; $(C_{1-4})$alkylcarbonyl; $(C_{2-4})$alkenyloxycarbonyl; $(C_{2-4})$alkenylcarbonyl; aminocarbonyl wherein the amino group is optionally substituted by hydroxy, $(C_{1-4})$alkyl, hydroxy$(C_{1-4})$alkyl, aminocarbonyl$(C_{1-4})$alkyl, $(C_{2-4})$alkenyl, $(C_{1-4})$alkylsulphonyl, trifluoromethylsulphonyl, $(C_{2-4})$alkenylsulphonyl, $(C_{1-4})$alkoxycarbonyl, $(C_{1-4})$alkylcarbonyl, $(C_{2-4})$alkenyloxycarbonyl or $(C_{2-4})$alkenylcarbonyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; 5-oxo-1,2,4-oxadiazol-3-yl; halogen; $(C_{1-4})$alkylthio; trifluoromethyl; hydroxy optionally substituted by $(C_{1-4})$alkyl, $(C_{2-4})$alkenyl, $(C_{1-4})$alkoxycarbonyl, $(C_{1-4})$alkylcarbonyl, $(C_{2-4})$alkenyloxycarbonyl, $(C_{2-4})$alkenylcarbonyl; oxo; $(C_{1-4})$alkylsulphonyl; $(C_{2-4})$alkenylsulphonyl; or $(C_{1-4})$ aminosulphonyl wherein the amino group is optionally substituted by $(C_{1-4})$alkyl or $(C_{2-4})$alkenyl;

$R^3$ is in the 2-, 3- or 4-position and is trifluoromethyl or is in the 2-position and is oxo; or $R^3$ is in the 3-position and is fluorine or amino wherein the amino group is optionally substituted by: hydroxy, $(C_{1-6})$alkylsulphonyl; trifluoromethylsulphonyl; $(C_{2-6})$alkenylsulphonyl; $(C_{1-6})$alkylcarbonyl; $(C_{2-6})$alkenylcarbonyl; $(C_{1-6})$alkoxycarbonyl; $(C_{2-6})$alkenyloxycarbonyl; $(C_{1-6})$alkyl; or $(C_{2-6})$alkenyl; wherein a $(C_{1-6})$alkyl or $(C_{2-6})$alkenyl moiety may be optionally substituted with up to 2 groups $R^{12}$ independently selected from:
halogen; $(C_{1-6})$alkylthio; trifluoromethyl; cyano; carboxy; tetrazolyl; 2-oxo-oxazolidinyl; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; or 5-oxo-1,2,4-oxadiazol-3-yl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy optionally substituted by $(C_{1-6})$alkyl, $(C_{2-6})$alkenyl, $(C_{1-6})$alkylcarbonyl, $(C_{2-6})$alkenylcarbonyl or aminocarbonyl wherein the amino group is optionally substituted by $(C_{1-6})$alkyl, $(C_{2-6})$alkenyl; amino optionally mono- or disubstituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$alkenylsulphonyl or aminocarbonyl wherein the amino group is optionally substituted by $(C_{1-6})$alkyl or $(C_{2-6})$alkenyl; in addition when $R^3$ is disubstituted with a hydroxy or amino containing substituent and carboxy containing substituent these may together form a cyclic ester or amide linkage, respectively;

$R^4$ is a group —U—$R^5$ where
U is selected from CO, $SO_2$ and $CH_2$ and
$R^5$ is an optionally substituted bicyclic carbocyclic or heterocyclic ring system (A):

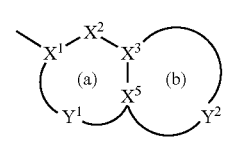

(A)

containing up to four heteroatoms in each ring in which ring (a) is aromatic and ring (b) is non-aromatic;
$X^1$ is C or N;
$X^2$ is N, $NR^{13}$, O, $S(O)_x$, CO or $CR^{14}$;
$X^3$ and $X^5$ are independently N or C;
$Y^1$ is a 0 to 4 atom linker group each atom of which is independently selected from N, $NR^{13}$, O, $S(O)_x$, CO and $CR^{14}$;
$Y^2$ is a 2 to 6 atom linker group, each atom of $Y^2$ being independently selected from N, $NR^{13}$, O, $S(O)_x$, CO, $CR^{14}$ and $CR^{14}R^{15}$;
each of $R^{14}$ and $R^{15}$ is independently selected from: H; $(C_{1-4})$alkylthio; halo; carboxy$(C_{1-4})$alkyl; halo$(C_{1-4})$alkoxy; halo$(C_{1-4})$ayl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy, $(C_{1-4})$alkoxycarbonyl$(C_{1-4})$alkyl; hydroxy; hydroxy$(C_{1-4})$alkyl; mercapto$(C_{1-4})$alkyl; $(C_{1-4})$alkoxy; trifluoromethoxy; nitro; cyano; carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally mono- or di-substituted by $(C_{1-4})$alkyl or $(C_{2-4})$alkenyl; aryl; aryl$(C_{1-4})$alkyl; aryl$(C_{1-4})$alkoxy;

each $R^{13}$ is independently H; trifluoromethyl; $(C_{1-4})$alkyl optionally substituted by hydroxy, $(C_{1-6})$alkoxy, $(C_{1-6})$alkylthio, halo or trifluoromethyl; $(C_{2-4})$alkenyl; aryl; aryl $(C_{1-4})$alkyl; arylcarbonyl; heteroarylcarbonyl; $(C_{1-4})$alkoxycarbonyl; $(C_{1-4})$alkylcarbonyl; formyl; $(C_{1-6})$alkylsulphonyl; or aminocarbonyl wherein the amino group is optionally substituted by $(C_{1-4})$alkoxycarbonyl, $(C_{1-4})$alkylcarbonyl, $(C_{2-4})$alkenyloxycarbonyl, $(C_{2-4})$alkenylcarbonyl, $(C_{1-4})$alkyl or $(C_{2-4})$alkenyl and optionally further substituted by $(C_{1-4})$alkyl or $(C_{2-4})$alkenyl;

each x is independently 0, 1 or 2 n is 0 and AB is $NR^{11}CO$, $CO-CR^8R^9$, $CR^6R^7-CO$, $NHR^{11}SO_2$, $CR^6R^7-SO_2$ or $CR^6R^7-CR^8R^9$, provided that $R^8$ and $R^9$ are not optionally substituted hydroxy or amino and $R^6$ and $R^8$ do not represent a bond:

or n is 1 and AB is $NR^{11}CO$, $CO-CR^8R^9$, $CR^6R^7-CO$, $NR^{11}SO_2$, $CONR^{11}$, $CR^6R^7-CR^8R^9$, $O-CR^8R^9$ or $NR^{11}-CR^8R^9$;

each of $R^6$, $R^7$, $R^8$ and $R^9$ is independently selected from: hydrogen; $(C_{1-6})$alkoxy; $(C_{1-6})$alkylthio; halo; trifluoromethyl; azido; $(C_{1-6})$alkyl; $(C_{2-6})$alkenyl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy, amino or aminocarbonyl optionally substituted as for corresponding substituents in $R^3$; $(C_{1-6})$alkylsulphonyl; $(C_{2-6})$alkenylsulphonyl; or aminosulphonyl wherein the amino group is optionally substituted by $(C_{1-6})$alkyl or $(C_{2-6})$alkenyl;

or when n=1 $R^6$ and $R^8$ together represent a bond and $R^7$ and $R^9$ are as above defined; or $R^6$ and $R^7$ or $R^8$ and $R^9$ together represent oxo;

$R^{10}$ is selected from $(C_{1-4})$alkyl; $(C_{2-4})$alkenyl and aryl any of which may be optionally substituted by a group $R^{12}$ as defined above; carboxy; aminocarbonyl wherein the amino group is optionally substituted by hydroxy, $(C_{1-6})$alkyl, $(C_{2-6})$alkenyl, $(C_{1-6})$alkylsulphonyl, trifluoromethylsulphonyl, $(C_{2-6})$alkenylsulphonyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl or $(C_{2-6})$alkenyl; and $R^{11}$ is hydrogen; trifluoromethyl; $(C_{1-6})$alkyl; $(C_{2-6})$alkenyl; $(C_{1-6})$alkoxycarbonyl; $(C_{1-6})$alkylcarbonyl; or aminocarbonyl wherein the amino group is optionally substituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl or $(C_{2-6})$alkenyl and optionally further substituted by $(C_{1-6})$alkyl or $(C_{2-6})$alkenyl;

or where one of $R^3$ and $R^6$, $R^7$, $R^8$ or $R^9$ contains a carboxy group and the other contains a hydroxy or amino group they may together form a cyclic ester or amide linkage.

This invention also provides a method of treatment of bacterial infections in mammals, particularly in man, which method comprises the administration to a mammal in need of such treatment an effective amount of a compound of formula (I), or a pharmaceutically acceptable derivative thereof.

The invention also provides the use of a compound of formula (I), or a pharmaceutically acceptable derivative thereof, in the manufacture of a medicament for use in the treatment of bacterial infections in mammals.

The invention also provides a pharmaceutical composition comprising a compound of formula (I), or a pharmaceutically acceptable derivative thereof, and a pharmaceutically acceptable carrier.

Preferably $Z^5$ is CH, C—Cl or N, $Z^3$ is CH or CF and $Z^1$, $Z^2$ and $Z^4$ are each CH, or $Z^1$ is N, $Z^3$ is CH and $Z^2$ and $Z^4$ are each CH and $Z^5$ is CH or C—Cl.

When $R^1$ or $R^{1a}$ is substituted alkoxy it is preferably $(C_{2-6})$alkoxy substitituted by optionally N-substituted amino, guanidino or amidino, or $(C_{1-6})$alkoxy substituted by piperidyl. Suitable examples of $R^1$ and $R^{1a}$ alkoxy include methoxy, trifluoromethoxy, n-propyloxy, iso-butyloxy, aminoethyloxy, aminopropyloxy, aminobutyloxy, aminopentyloxy, guanidinopropyloxy, piperidin-4-ylmethyloxy, phthalimido pentyloxy or 2-aminocarbonylprop-2-oxy.

Preferably $R^1$ and $R^{1a}$ are independently methoxy, $(C_{1-6})$alkyl, $(C_{1-6})$alkylthio, amino$(C_{3-5})$alkyloxy, guanidino$(C_{3-5})$alkyloxy, piperidyl$(C_{3-5})$alkyloxy, nitro, fluoro or chloro; $R^1$ is more preferably methoxy, fluoro or chloro. $R^{1a}$ is more preferably H, F or Cl. Most preferably $R^1$ is methoxy and $R^{1a}$ is H or when $Z^3$ is $CR^{1a}$ it may be C—F or when $Z^5$ is $CR^{1a}$ it may be C—F or C—Cl.

When $Z^5$ is $CR^{1a}$, $R^{1a}$ is preferably hydrogen, chloro, cyano, hydroxymethyl or carboxy, most preferably hydrogen or chloro.

Preferably n is 0.

$R^2$ is preferably hydrogen; $(C_{1-4})$alkyl substituted with carboxy, optionally substituted hydroxy, optionally substituted aminocarbonyl, optionally substituted amino or $(C_{1-4})$ alkoxycarbonyl; or $(C_{2-4})$alkenyl substituted with $(C_{1-4})$ alkoxycarbonyl or carboxy. More preferred groups for $R^2$ are hydrogen, carboxymethyl, hydroxyethyl, aminocarbonylmethyl, ethoxycarbonylmethyl, ethoxycarbonylallyl and carboxyallyl, most preferably hydrogen.

Examples of $R^3$ include $CF_3$, fluoro and oxo.

When $R^3$ is amino it is preferably unsubstituted or substituted by $(C_{1-6})$alkyl or $(C_{2-6})$alkenyl.

$R^3$ is preferably in the 3- or 4-position.

Most preferably $R^3$ is 3-F and more preferably it is cis to $(NR^2)R^4$.

Preferably n=0.

When A is CH(OH) the R-stereochemistry is preferred.

Preferably A is NH, $NCH_3$, $CH_2$, CHOH, $CH(NH_2)$, $C(Me)(OH)$ or $CH(Me)$.

Preferably B is $CH_2$ or CO.

Preferably A-B is $CHOH-CH_2$, $NR^{11}-CH_2$, $NR^{11}-CO$ or $CH_2-CH_2$.

Particularly preferred are those compounds where n=0, A is NH and B is CO, or A is $CH_2$ or CHOH and B is $CH_2$, when more preferably A is the R-isomer of CHOH.

Preferably $R^{11}$ is hydrogen or $(C_{1-4})$alkyl e.g. methyl, more preferably hydrogen.

U is most preferably $CH_2$.

Preferably in the heterocyclic ring (A) ring (a) is selected from optionally substituted benzo and pyrido and $Y^2$ has 3-5 atoms, more preferably 4 atoms, including a heteroatom bonded to $X^5$ selected from $NR^{13}$, O or S, where $R^{13}$ is other than hydrogen, and NHCO bonded via N to $X^3$, or O or NH bonded to $X^3$. The ring (a) preferably contains aromatic nitrogen, and more preferably ring (a) is pyridine. When ring (a) is pyridine, preferably $X^2$ is N and $Y^2$ has NHCO bonded via N to $X^3$ or preferably $Y^1$ has N bonded to $X^5$ and $Y^2$ has O bonded to $X^3$.

Examples of rings (A) include optionally substituted: 1,1,3-trioxo-1,2,3,4-tetrahydrol $1^6$-benzo[1,4]thiazin-3-one-6-yl, benzo[1,3]dioxol-5-yl, 2,3-dihydro-benzo[1,4]dioxin-6-yl, 2-oxo-2,3-dihydro-benzooxazol-6-yl, 3-substituted-3H-benzooxazol-2-one-6-yl, 3-substituted-3H-benzooxazole-2-thione-6-yl, 3-substituted-3H-benzothiazol-2-one-6-yl, 4H-benzo[1,4]oxazin-3-one-6-yl (3-oxo-3,4-dihydro-2H-benzo[1,4]oxazin-6-yl), 4H-benzo

[1,4]thiazin-3-one-6-yl (3-oxo-3,4-dihydro-2H-benzo[1,4]thiazin-6-yl), 4H-benzo[1,4]oxazin-3-one-7-yl, 4-oxo-2,3,4,5-tetrahydro-benzo[b][1,4]thiazepine-7-yl, 5-oxo-2,3-dihydro-5H-thiazolo[3,2-a]pyrimidin-6-yl, benzo[1,3]dioxol-5-yl, 1H-pyrido[2,3-b][1,4]thiazin-2-one-7-yl (2-oxo-2,3-dihydro-1H-pyrido[2,3-b]thiazin-7-yl), 2,3-dihydro-1H-pyrido[2,3-b][1,4]thiazin-7-yl, 2-oxo-2,3-dihydro-1H-pyrido[2,3-b]thiazin-7-yl, 2,3-dihydro-[1,4]dioxino[2,3-b]pyridin-6-yl, 2,3-dihydro-[1,4]dioxino[2,3-c]pyridin-7-yl, 2,3-dihydro-[1,4]dioxino[2,3-b]pyridin-7 -yl, 3,4-dihydro-2H-benzo[1,4]oxazin-6-yl, 3,4-dihydro-2H-benzo[1,4]thiazin-6-yl, 3-oxo-3,4-dihydro-2H-pyrido[3,2-b][1,4]oxazin-6-yl, 3,4-dihydro-2H-pyrido[3,2-b][1,4]thiazin-6-yl, 3-oxo-3,4-dihydro-2H-pyrido[3,2-b][1,4]thiazin-6-yl, 3,4-dihydro-1H-quinolin-2 -one-7-yl, 3,4-dihydro-1H-quinoxalin-2-one-7-yl, 6,7-dihydro-4H-pyrazolo[1,5-a]pyrimidin-5-one-2-yl, 5,6,7,8-tetrahydro-[1,8]naphthyridin-2-yl, 2-oxo-3,4-dihydro-1H-[1,8]naphthyridin-6-yl, 6,7-dihydro-[1,4]dioxino[2,3-d]pyrimidin-2-yl, 2-oxo-2,3-dihydro-1H-pyrido[3,4-b][1,4]oxazin-7-yl, 2-oxo-2,3-dihydro-1H-pyrido[2,3-b][1,4]oxazin-7-yl, 6-oxo-6,7-dihydro-5H-8-thia-1,2,5-triaza-naphthalen-3-yl.

$R^{13}$ is preferably H if in ring (a) or in addition ($C_{1-4}$)alkyl such as methyl or isopropyl when in ring (b). More preferably, in ring (b) $R^{13}$ is H when $NR^{13}$ is bonded to $X^3$ and ($C_{1-4}$)alkyl when $NR^{13}$ is bonded to $X^5$.

$R^{14}$ and $R^{15}$ are preferably independently selected from hydrogen, halo, hydroxy, ($C_{1-4}$)alkoxy, trifluoromethoxy, nitro, cyano, aryl($C_{1-4}$)alkoxy and ($C_{1-4}$)alkylsulphonyl. More preferably $R^{15}$ is hydrogen.

More preferably each $R^{14}$ is selected from hydrogen, chloro, fluoro, hydroxy, methoxy, trifluoromethoxy, benzyloxy, nitro, cyano and methylsulphonyl. Most preferably $R^{14}$ is selected from hydrogen, fluorine or nitro. Preferably 0-3 groups $R^{14}$ are substituents other than hydrogen. Preferably when $R^{14}$ is not hydrogen, $X^4$ is $CR^{14}$ and/or $CR^{14}$ is a component of $Y^2$.

More preferred groups $R^5$ include:
2,3-dihydro-benzo[1,4]dioxin-6-yl
benzo[1,3]dioxol-5-yl
2,2-difluoro-benzo[1,3]dioxol-5-yl
4H-benzo[1,4]oxazin-3-one-6-yl
4H-benzo[1,4]thiazin-3-one-6-yl
7-fluoro-4H-benzo[1,4]oxazin-3-one-6-yl
6-chloro-benzo[1,3]dioxol-5-yl
5-fluoro-3-methyl-3H-benzooxazol-2-one-6-yl
2,3-dihydro-[1,4]dioxino[2,3-c]pyridin-7-yl
3-oxo-3,4-dihydro-2H-pyrido[3,2-b][1,4]thiazin-6-yl
3,4-dihydro-2H-pyrido [3,2-b][1,4]thiazin-6-yl
3-oxo-3,4-dihydro-2H-pyrido[3,2-b][1,4]oxazin-6-yl
7-chloro-3-oxo-3,4-dihydro-2H-pyrido[3,2-b][1,4]oxazin-6-yl
7-bromo-3-oxo-3,4-dihydro-2H-pyrido[3,2-b][1,4]thiazin-6-yl
7-chloro-3-oxo-3,4-dihydro-2H-pyrido[3,2-b][1,4]thiazin-6-yl.

Most preferred groups $R^5$ include:
4H-benzo[1,4]oxazin-3-one-6-yl
4H-benzo[1,4]thiazin-3-one-6-yl
2,3-dihydro-[1,4]dioxino[2,3-c]pyridin-7-yl
3-oxo-3,4-dihydro-2H-pyrido[3,2-b]([1,4]thiazin-6-yl
3-oxo-3,4-dihydro-2H-pyrido[3,2-b][1,4]oxazin-6-yl
7-chloro-3-oxo-3,4-dihydro-2H-pyrido[3,2-b][1,4]oxazin-6-yl
7-chloro-3-oxo-3,4-dihydro-2H-pyrido[3,2-b][1,4]thiazin-6-yl.

When used herein, the term "alkyl" includes groups having straight and branched chains, for instance, methyl, ethyl, n-propyl, iso-propyl, n-butyl, iso-butyl, sec-butyl, t-butyl, pentyl and hexyl. The term 'alkenyl' should be interpreted accordingly.

Halo or halogen includes fluoro, chloro, bromo and iodo.
Haloalkyl moieties include 1-3 halogen atoms.

Unless otherwise defined, the term "heterocyclic" as used herein includes optionally substituted aromatic and non-aromatic, single and fused, rings suitably containing up to four hetero-atoms in each ring selected from oxygen, nitrogen and sulphur, which rings may be unsubstituted or C-substituted by, for example, up to three groups selected from ($C_{1-4}$)alkylthio; halo; carboxy($C_{1-4}$)alkyl; halo($C_{1-4}$)alkoxy, halo($C_{1-4}$)alkyl; ($C_{1-4}$)alkyl; ($C_{2-4}$)alkenyl; ($C_{1-4}$)alkoxycarbonyl; formyl; ($C_{1-4}$)alkylcarbonyl; ($C_{2-4}$)alkenyloxycarbonyl; ($C_{2-4}$)alkenylcarbonyl; ($C_{1-4}$)alkylcarbonyloxy; ($C_{1-4}$)alkoxycarbonyl($C_{1-4}$)alkyl; hydroxy; hydroxy($C_{1-4}$)alkyl; mercapto($C_{1-4}$)alkyl; ($C_{1-4}$)alkoxy; nitro; cyano, carboxy; amino or aminocarbonyl optionally substituted as for corresponding substituents in $R^3$; ($C_{1-4}$)alkylsulphonyl; ($C_{2-4}$)alkenylsulphonyl; or aminosulphonyl wherein the amino group is optionally substituted by ($C_{1-4}$)alkyl or ($C_{2-4}$)alkenyl; optionally substituted aryl, aryl($C_{1-4}$)alkyl or aryl($C_{1-4}$)alkoxy and oxo groups.

Each heterocyclic ring suitably has from 4 to 7, preferably 5 or 6, ring atoms. A fused heterocyclic ring system may include carbocyclic rings and need include only one heterocyclic ring.

Compounds within the invention containing a heterocyclyl group may occur in two or more tautometric forms depending on the nature of the heterocyclyl group; all such tautomeric forms are included within the scope of the invention.

Where an amino group forms part of a single or fused non-aromatic heterocyclic ring as defined above suitable optional substituents in such substituted amino groups include H; trifluoromethyl; ($C_{1-4}$)alkyl optionally substituted by hydroxy, ($C_{1-6}$)alkoxy, ($C_{1-6}$)alkylthio, halo or trifluoromethyl; ($C_{2-4}$)alkenyl; aryl; aryl ($C_{1-4}$)alkyl; ($C_{1-4}$)alkoxycarbonyl; ($C_{1-4}$)alkylcarbonyl; formyl; ($C_{1-6}$)alkylsulphonyl; or aminocarbonyl wherein the amino group is optionally substituted by ($C_{1-4}$)alkoxycarbonyl, ($C_{1-4}$)alkylcarbonyl, ($C_{2-4}$)alkenyloxycarbonyl, ($C_{2-4}$)alkenylcarbonyl, ($C_{1-4}$)alkyl or ($C_{2-4}$)alkenyl and optionally further substituted by ($C_{1-4}$)alkyl or ($C_{2-4}$)alkenyl.

When used herein the term "aryl", includes optionally substituted phenyl and naphthyl.

Aryl groups may be optionally substituted with up to five, preferably up to three, groups selected from ($C_{1-4}$)alkylthio; halo; carboxy($C_{1-4}$)alkyl; halo($C_{1-4}$)alkoxy; halo($C_{1-4}$)alkyl; ($C_{1-4}$)alkyl; ($C_{2-4}$)alkenyl; ($C_{1-4}$)alkoxycarbonyl; formyl; ($C_{1-4}$)alkylcarbonyl; ($C_{2-4}$)alkenyloxycarbonyl; ($C_{2-4}$)alkenylcarbonyl; ($C_{1-4}$)alkylcarbonyloxy; ($C_{1-4}$)alkoxycarbonyl($C_{1-4}$)alkyl; hydroxy, hydroxy($C_{1-4}$)alkyl; mercapto($C_{1-4}$)alkyl; ($C_{1-4}$)alkoxy, nitro; cyano; carboxy; amino or aminocarbonyl optionally substituted as for corresponding substituents in $R^3$; ($C_{1-4}$)alkylsulphonyl; ($C_{2-4}$)alkenylsulphonyl; or aminosulphonyl wherein the amino group is optionally substituted by ($C_{1-4}$)alkyl or ($C_{2-4}$)alkenyl; phenyl, phenyl($C_{1-4}$)alkyl or phenyl($C_{1-4}$)alkoxy.

The term "acyl" includes formyl and ($C_{1-6}$)alkylcarbonyl group.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the formula (I) or pharmaceutically acceptable derivative thereof.

Particular compounds according to the invention include those mentioned in the examples and their pharmaceutically acceptable derivatives.

Pharmaceutically acceptable derivatives of the above-mentioned compounds of formula (I) include the free base form or their acid addition or quaternary ammonium salts, for example their salts with mineral acids e.g. hydrochloric, hydrobromic, sulphuric nitric or phosphoric acids, or organic acids, e.g. acetic, fumaric, succinic, maleic, citric, benzoic, p-toluenesulphonic, methanesulphonic, naphthalenesulphonic acid or tartaric acids. Compounds of formula (I) may also be prepared as the N-oxide. Compounds of formula (I) having a free carboxy group may also be prepared as an in vivo hydrolysable ester. The invention extends to all such derivatives.

Examples of suitable pharmaceutically acceptable in vivo hydrolysable ester-forming groups include those forming esters which break down readily in the human body to leave the parent acid or its salt. Suitable groups of this type include those of part formulae (i), (ii), (iii), (iv) and (v):

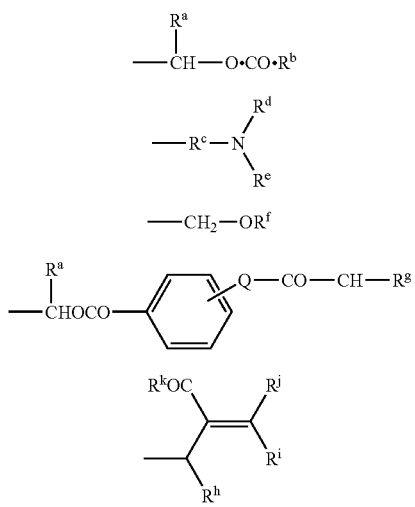

wherein $R^a$ is hydrogen, $(C_{1-6})$ alkyl, $(C_{3-7})$ cycloalkyl, methyl, or phenyl, $R^b$ is $(C_{1-6})$ alkyl, $(C_{1-6})$ alkoxy, phenyl, benzyl, $(C_{3-7})$ cycloalkyl, $(C_{3-7})$ cycloalkyloxy, $(C_{1-6})$ alkyl $(C_{3-7})$ cycloalkyl, 1-amino $(C_{1-6})$ alkyl, or 1-$(C_{1-6}$ alkyl)amino $(C_{1-6})$ alkyl; or $R^a$ and $R^b$ together form a 1,2-phenylene group optionally substituted by one or two methoxy groups; $R^c$ represents $(C_{1-6})$ alkylene optionally substituted with a methyl or ethyl group and $R^d$ and $R^e$ independently represent $(C_{1-6})$ alkyl; $R^f$ represents $(C_{1-6})$ alkyl; $R^g$ represents hydrogen or phenyl optionally substituted by up to three groups selected from halogen, $(C_{1-6})$ allyl, or $(C_{1-6})$ alkoxy; Q is oxygen or NH; $R^h$ is hydrogen or $(C_{1-6})$ alkyl; $R^i$ is hydrogen, $(C_{1-6})$ alkyl optionally substituted by halogen, $(C_{2-6})$ alkenyl, $(C_{1-6})$ alkoxycarbonyl, aryl or heteroaryl; or $R^h$ and $R^i$ together form $(C_{1-6})$ alkylene; $R^j$ represents hydrogen, $(C_{1-6})$ alkyl or $(C_{1-6})$ alkoxycarbonyl; and $R^k$ represents $(C_{1-8})$ alkyl, $(C_{1-8})$ alkoxy, $(C_{1-6})$ alkoxy$(C_{1-6})$alkoxy or aryl.

Examples of suitable in vivo hydrolysable ester groups include, for example, acyloxy$(C_{1-6})$alkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; $(C_{1-6})$alkoxycarbonyloxy$(C_{1-6})$alkyl groups, such as ethoxycarbonyloxymethyl, α-ethoxycarbonyloxyethyl and propoxycarbonyloxyethyl; di$(C_{1-6})$alkylamino$(C_{1-6})$alkyl especially di$(C_{1-4})$alkylamino$(C_{1-4})$alkyl groups such as dimethylaminomethyl, dimethylaminoethyl, diethylaminomethyl or diethylaminoethyl; 2-(($C_{1-6}$)alkoxycarbonyl)-2-($C_{2-6}$)alkenyl groups such as 2-(isobutoxycarbonyl)pent-2-enyl and 2-(ethoxycarbonyl)but-2-enyl; lactone groups such as phthalidyl and dimethoxyphthalidyl.

A further suitable pharmaceutically acceptable in vivo hydrolysable ester-forming group is that of the formula:

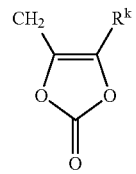

wherein $R^k$ is hydrogen, $C_{1-6}$ alkyl or phenyl.

R is preferably hydrogen.

Compounds of formula (I) may also be prepared as the corresponding N-oxides.

Certain of the compounds of formula (I) may exist in the form of optical isomers, e.g. diastereoisomers and mixtures of isomers in all ratios, e.g. racemic mixtures. The invention includes all such forms, in particular the pure isomeric forms. For example the invention includes compound in which an A-B group CH(OH)—CH$_2$ is in either isomeric configuration, the R-isomer is preferred. The different isomeric forms may be separated or resolved one from the other by conventional methods, or any given isomer may be obtained by conventional synthetic methods or by stereospecific or asymmetric syntheses.

In a further aspect of the invention there is provided a process for preparing compounds of formula (I), and pharmaceutically acceptable derivatives thereof, which process comprises reacting a compound of formula (V) with a compound of formula (V):

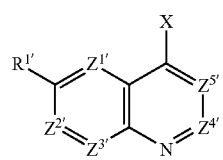

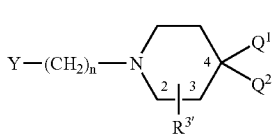

wherein n is as defined in formula (I); $Z^{1'}$, $Z^2$, $Z^{3'}$, $Z^{4'}$, $Z^{5'}$, $R^{1'}$, and $R^{3'}$ are $Z^1$, $Z^2$, $Z^3$, $Z^4$, $Z^5$, $R^1$, and $R^3$ as defined in formula (I) or groups convertible thereto;

$Q^1$ is $NR^{2'}R^{4'}$ or a group convertible thereto wherein $R^{2'}$ and $R^{4'}$ are $R^2$ and $R^4$ as defined in formula (I) or groups convertible thereto and $Q^2$ is H or $R^3$ or $Q^1$ and $Q^2$ together form an optionally protected oxo group;

(i) X is A'-COW, Y is H and n is 0;
(ii) X is $CR^6=CR^8R^9$, Y is H and n is 0;
(iii) X is oxirane, Y is H and n is 0;
(iv) X is N=C=O and Y is H and n is 0;
(v) one of X and Y is $CO_2R^y$ and the other is $CH_2CO_2R^x$;
(vi) X is $CHR^6R^7$ and Y is $C(=O)R^9$;
(vii) X is $CR^7=PR^z_3$ and Y is $C(=O)R^9$ and n=1;
(viii) X is $C(=O)R^7$ and Y is $CR^9=PR^z_3$ and n=1;
(ix) Y is COW and X is $NHR^{11'}$ or $NR^{11'}COW$ and n=0 or 1 or when n=1 X is COW and Y is $NHR^{11'}$ or $NR^{11'}COW$;
(x) X is $NHR^{11'}$ and Y is $C(-O)R^8$ and n=1;
(xi) X is $NHR^{11'}$ and Y is $CR^8R^9W$ and n=1;
(xii) X is $NR^{11'}COCH_2W$ or $NR^{11'}SO_2CH_2W$ and Y is H and n=0;
(xiii) X is $CR^6R^7SO_2W$ and Y is H and n=0;
(xiv) X is W or OH and Y is $CH_2OH$ and n is 1;
(xv) X is $NHR^{11'}$ and Y is $SO_2W$ or X is $NR^{11'}SO_2W$ and Y is H, and n is 0;
(xvi) X is W and Y is $CONHR^{11'}$;

in which W is a leaving group, e.g. halo or imidazolyl; $R^x$ and $R^y$ are $(C_{1-6})$alkyl; $R^z$ is aryl or $(C_{1-6})$alkyl; A' and $NR^{11'}$ are A and $NR^{11}$ as defined in formula (I), or groups convertible thereto; and oxirane is:

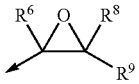

wherein $R^6$, $R^8$ and $R^9$ are as defined in formula (I);

and thereafter optionally or as necessary converting $Q^1$ and $Q^2$ to $NR^{2'}R^{4'}$; converting A', $Z^{1'}$, $Z^{2'}$, $Z^{3'}$, $Z^{4'}$, $Z^{5'}$, $R^{1'}$, $R^{2'}$, $R^{3'}$, $R^{4'}$ and $NR^{11'}$; to A, $Z^1$, $Z^2$, $Z^3$, $Z^4$, $Z^5$, $R^1$, $R^2$, $R^3$, $R^4$ and $NR^{11}$; converting A-B to other A-B, interconverting $R^1$, $R^2$, $R^3$ and/or $R^4$, and/or forming a pharmaceutically acceptable derivative thereof.

Process variant (i) initially produces compounds of formula (I) wherein A-B is A'-CO.

Process variant (ii) initially produces compounds of formula (I) wherein A-B is $CHR^6$—$CR^8R^9$.

Process variant (iii) initially produces compounds of formula (I) wherein A-B is $CR^6(OH)$—$CR^8R^9$.

Process variant (iv) initially produces compounds of formula (I) where A-B is NH—CO.

Process variant (v) initially produces compounds of formula (I) wherein A-B is CO—$CH_2$ or $CH_2$—CO.

Process variant (vi) initially produces compounds of formula (I) wherein A-B is $CR^6R^7$—$CR^9OH$.

Process variant (vii) and (viii) initially produce compounds of formula (I) wherein A-B is $CR^7=CR^9$.

Process variant (ix) initially produces compounds of formula (I) where A-B is CO—$NR^{11}$ or $NR^{11}$—CO.

Process variant (x) initially produces compounds of formula (I) wherein A-B is $NR^{11'}$—$CHR^8$.

Process variant (xi) initially produces compounds of formula (I) wherein A-B is $NR^{11'}$—$CR^8R^9$.

Process variant (xii) initially produces compounds of formula (I) where A-B is $NR^{11'}$—CO or $NR^{11'}$—$SO_2$ and n=1.

Process variant (xiii) initially produces compounds of formula (I) where A-B is $CR^6R^7$—$SO_2$.

Process variant (xiv) initially produces compounds of formula (I) wherein A-B is O—$CH_2$.

Process variant (xv) initially produces compounds where AB is $NR^{11}SO_2$.

Process variant (xvi) initially produces compounds of formula (I) where A-B is $NR^{11'}$—CO.

In process variants (i) and (ix) the reaction is a standard amide or urea formation reaction involving e.g.:

1. Activation of a carboxylic acid (e.g. to an acid chloride, mixed anhydride, active ester, O-acyl-isourea or other species), and treatment with an amine (Ogliaruso, M. A.; Wolfe, J. F. in *The Chemistry of Functional Groups* (Ed. Patai, S.) Suppl. B: *The Chemistry of Acid Derivatives*, Pt. 1 (John Wiley and Sons, 1979), pp 442-8; Beckwith, A. L. J. in *The Chemistry of Functional Groups* (Ed. Patai, S.) Suppl. B: *The Chemistry of Amides* (Ed. Zabricky, J.) (John Wiley and Sons, 1970), p 73 ff. The acid and amine are preferably reacted in the presence of an activating agent such as 1-(dimethylaminopropyl)-3-ethylcarbodiimide hydrochloride (EDC) or 1-hydroxybenzotriazole (HOBT) or O-(7-azabenzotriazol-1-yl)-N,N,N',N'-tetramethyluronium hexafluorophosphate (HATU); or 2. The specific methods of:
a. in situ conversion of an acid into the amine component by a modified Curtius reaction procedure (Shioiri, T., Murata, M., Hamada, Y., *Chem. Pharm. Bull.* 1987, 35, 2698)
b. in situ conversion of the acid component into the acid chloride under neutral conditions (Villeneuve, G. B.; Chan, T. H., *Tetrahedron. Lett.* 1997, 38, 6489).

A' may be, for example. protected hydroxymethylene.

The process variant (ii) is a standard addition reaction using methods well known to those skilled in the art. The process is preferably carried out in a polar organic solvent e.g. acetonitrile in the presence of an organic base e.g. triethylamine.

In process variant (iii) the coupling may be effected in a suitable solvent such as acetonitrile or dimethylformamide at room temperature in the presence of one equivalent of lithium perchlorate as catalyst (general method of J. E. Chateauneuf et al, *J. Org. Chem.*, 56, 5939-5942, 1991) or more preferably with ytterbium triflate in dichloromethane. In some cases an elevated temperature such as 40-70° C. may be beneficial. Alternatively, the piperidine may be treated with a base, such as one equivalent of butyl lithium, and the resulting salt reacted with the oxirane in an inert solvent such as tetrahydrofuran, preferably at an elevated temperature such as 80° C. Use of a chiral epoxide will afford single diastereomers. Alternatively, mixtures of diastereomers may be separated by preparative HPLC or by conventional resolution through crystallisation of salts formed from chiral acids.

The process variant (iv) is a standard urea formation reaction from the reaction of an isocyanate with an amine and is conducted by methods well known to those skilled in the art (for example see March, J; *Advanced Organic Chemistry, Edition* 3 (John Wiley and Sons, 1985), p 802-3). The process is preferably carried out in a polar solvent such as N,N-dimethylformamide.

In process variant (v) the process is two step: firstly a condensation using a base, preferably sodium hydride or alkoxide, sodamide, alkyl lithium or lithium dialkylamide, preferably in an aprotic solvent e.g. ether, THF or benzene; secondly, hydrolysis using an inorganic acid, preferably HCl in aqueous organic solvent at 0-100° C. Analogous routes are described in DE330945, EP31753, EP53964 and H. Sargent, J. Am. Chem. Soc. 68, 2688-2692 (1946). Similar Claisen methodology is described in Soszko et. al., Pr.Kom.Mat. Przyr.Poznan.Tow.Przyj.Nauk., (1962), 10, 15.

In process variant (vi) the reaction is carried out in the presence of a base, preferably organometallic or metal hydride e.g. NaH, lithium diisopropylamide or NaOEt, preferably in an aprotic solvent, preferably THF, ether or benzene at −78 to 25° C. (analogous process in Gutswiller et al. (1978) J. Am. Chem. Soc. 100, 576).

In process variants (vii) and (viii) if a base is used it is preferably NaH, KH, an alkyl lithium e.g. BuLi, a metal alkoxide e.g. NaOEt, sodamide or lithium dialkylamide e.g. di-isopropylamide. An analogous method is described in U.S. Pat. No. 3,989,691 and M. Gates et. al. (1970) J. Amer. Chem. Soc., 92, 205, as well as Taylor et al. (1972) JACS 94, 6218.

In process variant (x) where Y is CHO the reaction is a standard reductive alkylation using, e.g., sodium borohydride or sodium triacetoxyborohydride (Gribble, G. W. in *Encyclopedia of Reagents for Organic Synthesis (Ed. Paquette, L. A)* (John Wiley and Sons, 1995), p 4649).

The process variant (xi) is a standard alkylation reaction well known to those skilled in the art, for example where an alcohol or amine is treated with an alkyl halide in the presence of a base (for example see March, J; *Advanced Organic Chemistry, Edition* 3 (John Wiley and Sons, 1985), p 364-366 and p 342-343). The process is preferably carried out in a polar solvent such as N,N-dimethylformamide.

In process variant (xii) the reaction is an alkylation, examples of which are described in J. Med. chem. (1979) 22 (10) 1171-6. The compound of formula (IV) may be prepared from the corresponding compound where X is $NHR^{11'}$ by acylation with an appropriate derivative of the acid $WCH_2COOH$ such as the acid chloride or sulphonation with an appropriate derivative of the sulphonic acid $WCH_2SO_3H$ such as the sulphonyl chloride.

In process variant (xiii) the reaction is a standard sulphonamide formation reaction well known to those skilled in the art. This may be e.g. the reaction of a sulphonyl halide with an amine.

In process variant (xiv) where X is W such as halogen, methanesulphonyloxy or trifluoromethanesulphonyloxy, the hydroxy group in Y is preferably converted to an OM group where M is an alkali metal by treatment of an alcohol with a base. The base is preferably inorganic such as NaH, lithium diisopropylamide or sodium. Where X is OH, the hydroxy group in Y is activated under Mitsunobu conditions (Fletcher et. al. J Chem Soc. (1995), 623). Alternatively the X=O and Y=$CH_2OH$ groups can be reacted directly by activation with dichlorocarbodiimide (DCC) (Chem. Berichte 1962, 95, 2997 or Angewante Chemie 1963 75, 377).

In process variant (xv) the reaction is conducted in the presence of an organic base such as triethylamine or pyridine such as described by Fuhrman et. al., J. Amer. Chem. Soc.; 67, 1245, 1945. The $X=NR^{11'}SO_2W$ or $Y=SO_2W$ intermediates can be formed from the requisite amine e.g. by reaction with $SO_2Cl_2$ analogously to the procedure described by the same authors Fuhrman et. al., J. Amer. Chem. Soc.; 67, 1245, 1945.

In process variant (xvi) the leaving group W is preferably chloro, bromo or iodo or trifluoromethylsulphonyloxy and the reaction is the palladium catalysed process known as the "Buchwald" reaction (J. Yin and S. L. Buchwald, Org. Lett., 2000, 2, 1101).

Reduction of a carbonyl group A or B to CHOH can be readily accomplished using reducing agents well known to those skilled in the art, e.g. sodium borohydride in aqueous ethanol or lithium aluminium hydride in ethereal solution. This is analogous to methods described in EP53964, US384556 and J. Gutzwiller et al, J. Amer. Chem. Soc., 1978, 100, 576.

The carbonyl group A or B may be reduced to $CH_2$ by treatment with a reducing agent such as hydrazine in ethylene glycol, at e.g. 130-160° C., in the presence of potassium hydroxide.

Reaction of a carbonyl group A or B with an organometallic reagent yields a group where $R^6$ or $R^8$ is OH and $R^7$ or $R^9$ is alkyl.

A hydroxy group on A or B may be oxidised to a carbonyl group by oxidants well known to those skilled in the art, for example, manganese dioxide, pyridinium chlorochromate or pyridinium dichromate.

A hydroxyalkyl A-B group $CHR^7CR^9OH$ or $CR^7(OH)CHR^9$ may be dehydrated to give the group $CR^7=CR^9$ by treatment with an acid anhydride such as acetic anhydride.

Methods for conversion of $CR^7=CR^9$ by reduction to $CHR^7CHR^9$ are well known to those skilled in the art, for example using hydrogenation over palladium on carbon as catalyst. Methods for conversion of $CR^7=CR^9$ to give the A-B group $CR^7(OH)CHR^9$ or $CHR^7CR^9OH$ are well known to those skilled in the art for example by epoxidation and subsequent reduction by metal hydrides, hydration, hydroboration or oxymercuration.

An amide carbonyl group may be reduced to the corresponding amine using a reducing agent such as lithium aluminium hydride.

A hydroxy group in A or B may be converted to azido by activation and displacement e.g. under Mitsunobu conditions using hydrazoic acid or by treatment with diphenylphosphorylazide and base, and the azido group in turn may be reduced to amino by hydrogenation.

An example of a group $Q^1$ convertible to $NR^2R^4$ is $NR^{2'}R^{4'}$ or halogen. Halogen may be displaced by an amine $HNR^{2'}R^{4'}$ by a conventional alkylation.

When $Q^1 Q^2$ together form a protected oxo group this may be an acetal such as ethylenedioxy which can subsequently be removed by acid treatment to give a compound of formula (VI):

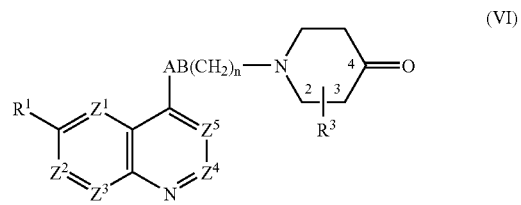

wherein the variables are as described for formula (I).

The ketone of formula (VI) is reacted with an amine $HNR^{2'}R^{4'}$ by conventional reductive alkylation as described above for process variant (x).

Examples of groups $Z^{1'}$, $Z^{2'}$, $Z^{3'}$, $Z^{4'}$, $Z^{5'}$ convertible to $Z^1$, $Z^2$, $Z^3$, $Z^4$ and $Z^5$ include $CR^{1a'}$ where $R^{1a'}$ is a group convertible to $R^{1a}$. $Z^{1'}$, $Z^{2'}$, $Z^{3'}$, $Z^{4'}$ and $Z^{5'}$ are preferably $Z^1$, $Z^2$, $Z^3$, $Z^4$ and $Z^5$.

$R^{1a'}$, $R^{1'}$ and $R^{2'}$ are preferably $R^{1a}$, $R^1$ and $R^2$. $R^{1'}$ is preferably methoxy. $R^{2'}$ is preferably hydrogen. $R^{3'}$ is $R^3$ or more preferably hydrogen, vinyl, alkoxycarbonyl or carboxy. $R^{4'}$ is $R^4$ or more preferably H or an N-protecting group such as t-butoxycarbonyl, benzyloxycarbonyl or 9-fluorenylmethyloxycarbonyl.

Conversions of $R^{1'}$, $R^{2'}$, $R^{3'}$ and $R^{4'}$ and interconversions of $R^1$, $R^2$, $R^3$ and $R^4$ are conventional. In compounds which contain an optionally protected hydroxy group, suitable conventional hydroxy protecting groups which may be removed without disrupting the remainder of the molecule include acyl and alkylsilyl groups. N-protecting groups are removed by conventional methods.

For example $R^{1'}$ methoxy is convertible to $R^{1'}$ hydroxy by treatment with lithium and diphenylphosphine (general method described in Ireland et al, *J. Amer. Chem. Soc.*, 1973, 7829) or HBr. Alkylation of the hydroxy group with a suitable alkyl derivative bearing a leaving group such as halide and a protected amino, piperidyl, amidino or guanidino group or group convertible thereto, yields, after conversion/deprotection, $R^1$ alkoxy substituted by optionally N-substituted amino, piperidyl, guanidino or amidino.

Substituted 2-oxo-oxazolidinyl containing $R^3$ groups may be prepared from the corresponding aldehyde by conventional reaction with a glycine anion equivalent, followed by cyclisation of the resulting amino alcohol (M. Grauert et al, *Ann. Chem.*, 1985, 1817; Rozenberg et al, *Angew. Chem. Int. Ed. Engl.*, 1994, 33 (1), 91). The resulting 2-oxo-oxazolidinyl group contains a carboxy group which can be converted to other $R^{10}$ groups by standard procedures.

Carboxy groups within $R^3$ may be prepared by Jones' oxidation of the corresponding alcohols $CH_2OH$ using chromium acid and sulphuric acid in water/methanol (E. R. H. Jones et al, *J. Chem. Soc.*, 1946, 39). Other oxidising agents may be used for this transformation such as sodium periodate catalysed by ruthenium trichloride (G. F. Tutwiler et al, *J. Med. Chem.*, 1987, 30 (6), 1094), chromium trioxide-pyridine (G. Just et al, *Synth. Commun.*, 1979, 9 (7), 613), potassium permanganate (D. E. Reedich et al, *J. Org. Chem.*, 1985, 50 (19), 3535), and pyridinium chlorochromate (D. Askin et al, *Tetrahedron Lett.*, 1988, 29 (3), 277).

The carboxy group may alternatively be formed in a two stage process, with an initial oxidation of the alcohol to the corresponding aldehyde using for instance dimethyl sulphoxide activated with oxalyl chloride (N. Cohen et al, *J. Am. Chem. Soc.*, 1983, 105, 3661) or dicyclohexylcarbodiimide (R. M. Wengler, *Angew. Chim. Int. Ed. Eng.*, 1985, 24 (2), 77), or oxidation with tetrapropylammonium perruthenate (Ley et al, *J. Chem. Soc. Chem Commun.*, 1987, 1625). The aldehyde may then be separately oxidised to the corresponding acid using oxidising agents such as silver (II) oxide (R. Grigg et al, *J. Chem. Soc. Perkin1*, 1983, 1929), potassium permanganate (A. Zurcher, *Helv. Chim. Acta.*, 1987, 70 (7), 1937), sodium periodate catalysed by ruthenium trichloride (T. Sakata et al, *Bull. Chem. Soc. Jpn.*, 1988, 61 (6), 2025), pyridinium chlorochromate (R. S. Reddy et al, *Synth. Commun.*, 1988, 18 (51), 545) or chromium trioxide (R. M. Coates et al, *J. Am. Chem. Soc.*, 1982, 104, 2198).

An $R^3$ $CO_2H$ group may also be prepared from oxidative cleavage of the corresponding diol, $CH(OH)CH_2OH$, using sodium periodate catalysed by ruthenium trichloride with an acetontrile-carbontetrachloride-water solvent system (V. S. Martin et al, *Tetrahedron Letters*, 1988, 29 (22), 2701).

Other routes to the synthesis of carboxy groups within $R^3$ are well known to those skilled in the art.

$R^3$ groups containing a cyano or carboxy group may also be prepared by conversion of an alcohol to a suitable leaving group such as the corresponding tosylate by reaction with para-toluenesulphonyl chloride (M. R. Bell, *J. Med. Chem.*, 1970, 13, 389), or the iodide using triphenylphosphine, iodine, and imidazole (G. Lange, *Synth. Commun.*, 1990, 2, 1473). The second stage is the displacement of the leaving group with cyanide anion (L. A. Paquette et al, *J. Org. Chem.*, 1979, 44 (25), 4603; P. A. Grieco et al, *J. Org. Chem.*, 1988, 53 (16), 3658. Finally acidic hydrolysis of the nitrile group gives the desired acids (H. Rosemeyer et al, *Heterocycles*, 1985, 23 (10), 2669). The hydrolysis may also be carried out with base e.g. potassium hydroxide (H. Rapoport, *J. Org. Chem.*, 1958, 23, 248) or enzymatically (T. Beard et al, *Tetrahedron Asymmetry*, 1993, 4 (6), 1085).

$R^{3'}$ cis or trans hydroxy may be introduced by the methods of van Deale et al., *Drug Development Research* 8: 225-232 (1986) or *Heterocycles* 39 (1), 163-170 (1994). For trans hydroxy, a suitable method converts N-protected tetrahydropyridine to the epoxide by treatment with metachloroperbenzoic acid, followed by opening of the epoxide with a suitable amine $NR^{2'}R^{4'}$. $R^{3'}$ hydroxy may then be converted to optionally substituted amino via preparation of the $R^{3'}$ amino derivative by standard transformations such as a Mitsunobu reaction (for eaxmple as reviewed in Misunobu, *Synthesisi*, (1981), 1), for example with succinimide in the presence of diethylazodicarboxylate and triphenylphosphine to give the phthalimidoethylpiperidine. Removal of the phthaloyl group, for example by treatment with methylhydrazine, affords the $R^{3'}$ amine. Optional substitution may then be introduced by standard methods for amine substitution well known to those skilled in the art.

$R^3$ 4-$CF_3$ may be introduced by the following scheme I:

Scheme I

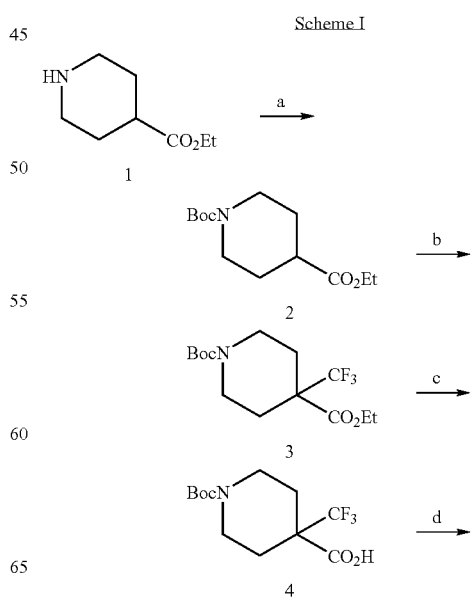

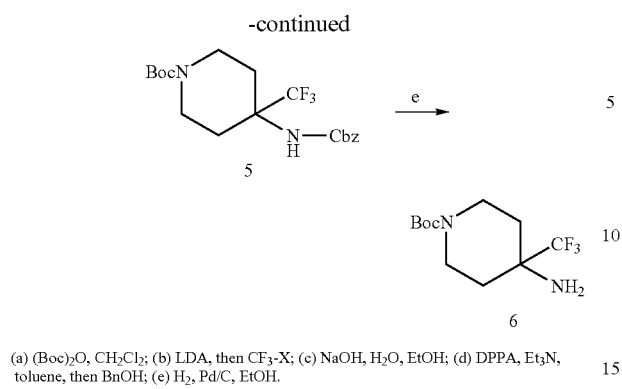

(a) (Boc)₂O, CH₂Cl₂; (b) LDA, then CF₃-X; (c) NaOH, H₂O, EtOH; (d) DPPA, Et₃N, toluene, then BnOH; (e) H₂, Pd/C, EtOH.

Commercially-available ethyl isonipecotate (I-1) reacts with an appropriate acylating agent, preferably di-tert-butyl dicarbonate, to afford the protected derivative I-2. Typical solvents for this reaction include CH₂Cl₂, THF, or DMF. The protecting group for the amine must be compatible with subsequent chemistry, and must be readily removable when desired. Methods for the protection of amines are well-known to those of skill in the art, and are described in standard reference volumes, such as Greene "Protective Groups in Organic Synthesis" (published by Wiley-Interscience). Alkylation of I-2 can be accomplished by reaction with an appropriate base, typically LDA or LiN(TMS)₂, in an aprotic solvent, usually THF or DME, followed by trapping of the enolate with an appropriate electrophile, to afford I-3. Trifluoromethyl iodide (CF₃I) or S-(trifluoromethyl)dibenzothiophenium trifluoromethanesulfonate are typically preferred as electrophilic trifluoromethylating reagents. The ethyl ester of I-3 is hydrolyzed using aqueous base, for example, LiOH in aqueous THF or NaOH in aqueous methanol or ethanol, and the intermediate carboxylate salt is acidified with a suitable acid, for instance TFA or HCl, to afford the carboxylic acid I-4. Curtius-type rearrangement of I-4 gives an intermediate isocyanate, which typically is not isolated, but rather is reacted in situ with an appropriate alcohol, such as benzyl alcohol, to give I-5. Diphenylphosphoryl azide in the presence of an amine base, generally triethylamine or diisopropylethylamine (Hunig's base), is the preferred reagent combination for effecting the Curtius-type rearrangement of I-4, but more classical conditions, such as formation of the acid chloride, reaction with azide anion, and warming of the acyl azide, can also be used. The benzyloxycarbonyl group in I-5 is removed by hydrogenolysis in the presence of a palladium catalyst, typically palladium on activated charcoal, in a suitable solvent, usually EtOH, MeOH, EtOAc, or mixtures thereof, to give amine I-6.

R³ 2-CF₃ may be introduced by the following scheme II:

Scheme II

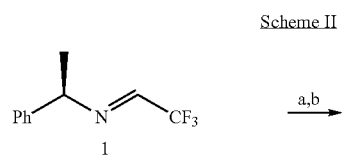

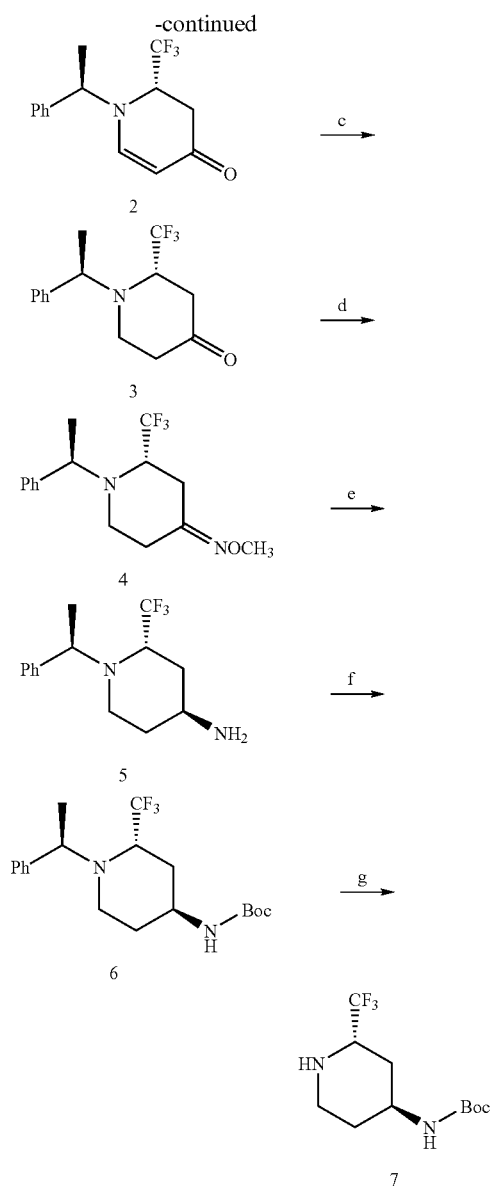

(a) 1-methoxy-3-(trimethylsilyloxy)-1,3-butadiene, ZnCl₂, CH₃CN;
(b) separate diastereomers; (c) L-Selectride® (lithium tri-sec-butylborohydride), THF then pyridinium dichromate, CH₂Cl as necessary; (d) NH₂OCH₃, p-TsOH, toluene; or NH₂OCH₃, NaOAc, EtOH; (e) LiAlH₄, THF; or Al-Ni, 2N NaOH, EtOH;
(f) (Boc)₂O, CH₂Cl₂ or THF or DMF; (g) H₂, Pd/C, EtOH.

Imine II-1, prepared in standard fashion by acid-catalyzed reaction of trifluoroacetaldehyde ethyl hemiacetal and (R)-(+)-α-methylbenzylamine, reacts with a silyloxydiene, for example 1-methoxy-3-(trimethylsilyloxy)-1,3-butadiene, in a Diels-Alder reaction to afford piperidone II-2. The reaction is conducted in a neutral solvent such as CH₃CN, THF, or CH₂Cl₂, and oftentimes is mediated by a Lewis acid such as ZnCl₂. Diastereomers are best separated at this point. The enone II-2 is reduced to the corresponding ketone or alcohol II-3 by reaction with L-Selectridet (lithium tri-sec-butylborohydride) in a suitable solvent, generally THF or DME, followed as necessary by subsequent oxidation of the alcohol to the ketone under standard conditions (pyridinium dichromate) and the ketone is converted to an oxime derivative under standard conditions well-known to those of skill in the art by reaction with O-methylhydroxylamine under standard conditions. Reduction of the oxime derivative under standard conditions (LiAlH₄ or according to the general method of Staskun and Van Es (*J. Chem. Soc. C* 1966, 531)) gives a mixture of diastereomeric amines from which the amine II-5 can be isolated. The amine is protected with an appropriate protecting group, preferably a tert-butyl carbamate (see Scheme I), to afford II-6. Typical solvents for this reaction include CH₂Cl₂, THF, or DMF. The protecting group for the amine must be compatible with subsequent chemistry, and must be readily removable when desired. Methods for the protection of amines are well-known to those of skill in the art, and are described in standard reference volumes, such as Greene "Protective Groups in Organic Synthesis" (published by Wiley-Interscience). The α-methylbenzyl group of II-6 is removed by hydrogenolysis in the presence of a palladium catalyst, typically palladium on activated charcoal, in a suitable solvent, usually EtOH, MeOH, EtOAc, or mixtures thereof, to give amine II-7.

R³ 3-CF₃ may be introduced by the following scheme III:

ylsilyl triflate, in the presence of an amine base, typically triethylamine, in a suitable solvent, such as diethyl ether, THF, DMF, or mixtures thereof. The silyl enol ether III-2 reacts with an electrophilic trifluoromethylating reagent, such as trifluoromethyl iodide (CF₃I) or more preferably S-(trifluoromethyl)dibenzothiophenium trifluoromethanesulfonate (see *Tet. Lett.* 1990, 31, 3579-3582)), in an appropriate solvent, such as THF, DMF, or mixtures thereof, to afford the α-trifluoromethyl ketone III-3. Ketone III-3 reacts with a chiral amine, for instance (R)-(+)-α-methylbenzylamine, under standard acidic catalysis, to afford the imine derivative III-4, which can be reduced to afford amine III-5. This type of reduction is typically conducted using sodium borohydride, sodium cyanoborohydride or sodium (triacetoxy)borohydride, in an appropriate solvent, such as EtOH, MeOH, THF, CH₂Cl₂, ClCH₂CH₂Cl, or mixtures thereof. Diastereomers are best separated at this point. The α-methylbenzyl group of III-5 is removed by hydrogenolysis in the presence of a palladium catalyst, typically palladium on activated charcoal, in a suitable solvent, usually EtOH, MeOH, EtOAc, or mixtures thereof, to give amine III-6.

R³ 2-oxo may be introduced by the following scheme IV:

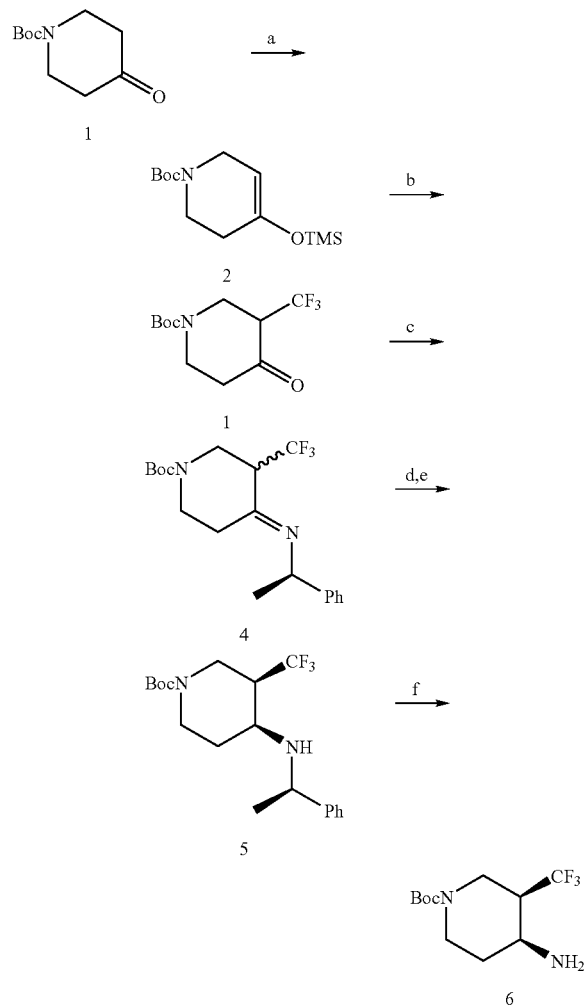

(a) TMSCl, Et₃N, DMF; (b) CF₃-X, DMF; (c) (R)-(+)-α-methylbenzylamine, p-TsOH, toluene; (d) NaBH₄, EtOH; (e) separate diastereomers; (f) H₂, Pd/C, EtOH.

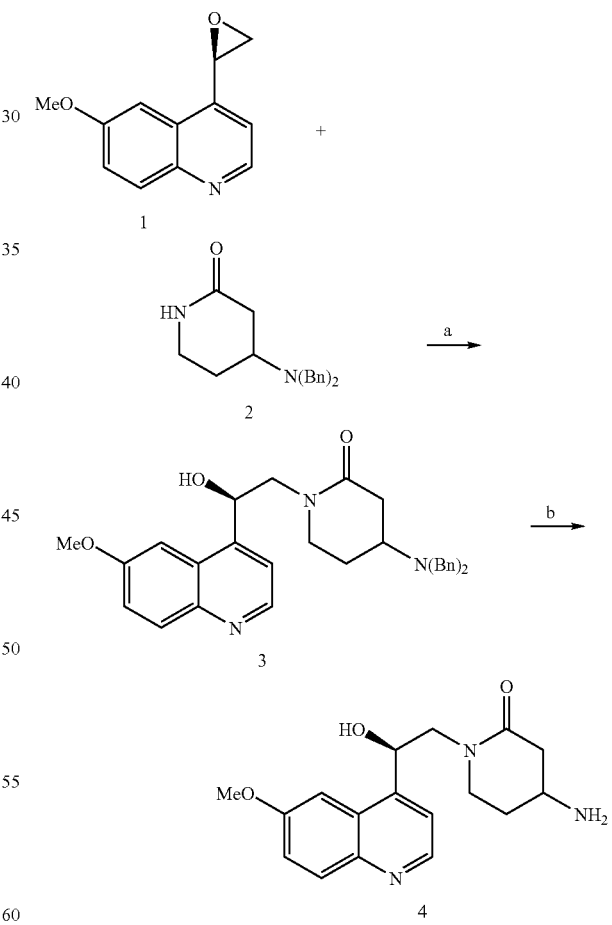

(a) NaH, THF, 0° C. to RT; (b) 10% Pd/C, H₂, MeOH.

The commercially-available ketone III-1 is converted to the corresponding silyl enol ether III-2 by reaction with a silylating reagent, such a trimethylsilyl chloride or trimeth- (R,S)-4-(Dibenzylamino)piperidin-2-one (IV-2, Homo-Freidinger Lactam, prepared from (R,S)-aspartic acid according to the procedure of Weber and Gmeiner, *Synlett*, 1998, 885-887) reacts with an appropriate epoxide, for instance 6-methoxy-4-(R)-oxiranylquinoline (VI-1) or 6-methoxy-4-(R)-oxiranyl-[1,5]naphthyridine, to afford the adduct IV-3. The reaction is mediated by a strong base, preferably sodium hydride, which is used to deprotonate IV-2, and is typically conducted in a polar, aprotic solvent, such as THF, DMF, or mixtures thereof. The benzyl groups in IV-3 are removed by hydrogenolysis in the presence of a palladium catalyst, typically palladium on activated charcoal, in a suitable solvent, usually EtOH, MeOH, EtOAc, or mixtures thereof, to give amine IV-4.

$R^3$ 3-F may be introduced by the following scheme V:

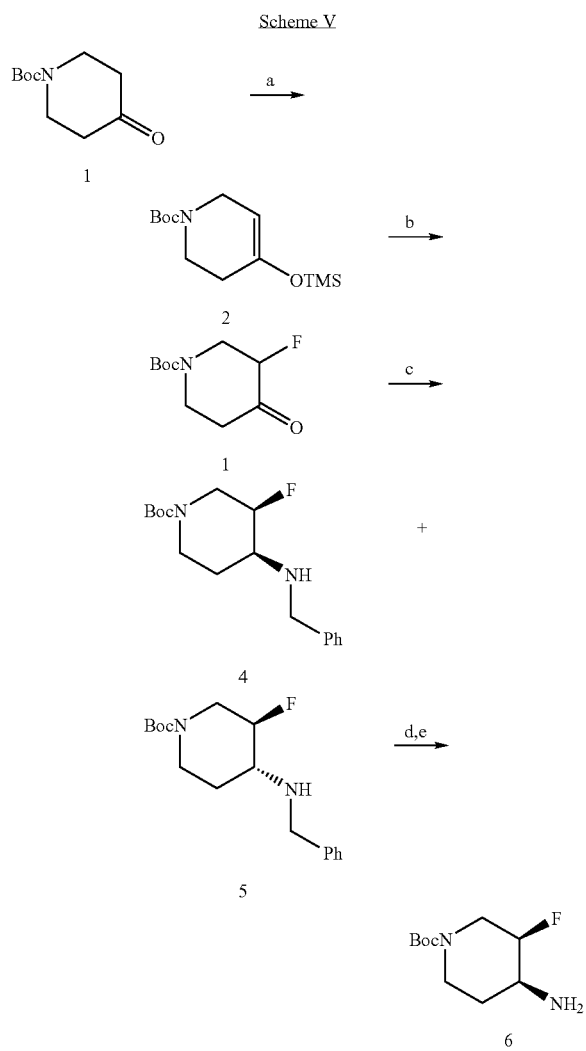

(a) TMSCl, Et₃N, DMF, 80° C.; (b) Selectflour, CH₃CN; (c) benzylamine, 1,2-dichloroethane, Na(OAc)₃BH; (d) separate diastereomers; (e) 10% Pd/C, H₂, HCl, EtOH.

The trimethylsilyl enol ether (V-2), prepared from commercially-available N-(tert-butoxycarbonyl)piperidone (V-1) as described in Scheme III, reacts with an electrophilic fluorinating reagent, preferably Selectfluor (1-chloromethyl-4-fluoro-1,4-diazabicyclo[2.2.2]octane bis(tetrafluoroborate), in a neutral solvent such as CH₃CN, to afford the c-fluoro ketone V-3. Reductive amination of V-3 with benzylamine according to the procedures described in Schemes I and III gives the expected 4-aminobenzyl-3-fluoro-N-(tert-butoxycarbonyl)piperidine derivatives V-4 and V-5 as a mixture of cis- and trans-isomers in an 8:1 ratio. These diastereomers are separable by chromatography on silica gel. The predominate cis-mixture of enantiomers is debenzylated by catalytic hydrogenation as described in Scheme II, to give the amino derivative V-6.

Other functional groups in $R^3$ may be obtained by conventional conversions of hydroxy, carboxy or cyano groups.

Tetrazoles are conveniently prepared by reaction of sodium azide with the cyano group (e.g. F. Thomas et al, Bioorg. Med. Chem. Lett., 1996, 6 (6), 631; K. Kubo et al, J. Med. Chem., 1993, 36, 2182) or by reaction of azidotri-n-butyl stannane with the cyano group followed by acidic hydrolysis (P. L. Ornstein, J. Org. Chem., 1994, 59 7682 and J. Med. Chem, 1996, 39 (11), 2219).

The 3-hydroxy-3-cyclobutene-1,2-dion-4-yl group (e.g. R. M. Soll, Bioorg. Med. Chem. Lett., 1993, 34 757 and W. A. Kinney, J. Med. Chem., 1992, 35 (25), 4720) can be prepared by the following sequence:—(1) a group (CH₂)ₙCHO (n=0, 1, 2) is treated with triethylamine, carbon tetrabromide-triphenylphosphine to give initially (CH₂)ₙCH=CHBr; (2) dehydrobromination of this intermediate to give the corresponding bromoethyne derivative (CH₂)ₙC≡CBr (for this 2 stage sequence see D. Grandjean et al, Tetrahedron Lett., 1994, 35 (21), 3529); (3) palladium-catalysed coupling of the bromoethyne with 4-(1-methylethoxy)-3-(tri-n-butylstannyl)cyclobut-3-ene-1,2-dione (Liebeskind et al, J. Org. Chem., 1990, 55, 5359); (4) reduction of the ethyne moiety to —CH₂CH₂— under standard conditions of hydrogen and palladium on charcoal catalysis(see Howard et al, Tetrahedron, 1980, 36, 171); and finally (4) acidic hydrolysis of the methyl ethoxyester to generate the corresponding 3-hydroxy-3-cyclobutene-1,2-dione group (R. M. Soll, Bioorg. Med. Chem. Lett., 1993, 3 (4), 757).

The tetrazol-5-ylaminocarbonyl group may be prepared from the corresponding carboxylic acid and 2-aminotetrazole by dehydration with standard peptide coupling agents such as 1,1'-carbonyldiimidazole (P. L. Ornstein et al, J. Med Chem, 1996, 39 (11), 2232).

The alkyl- and alkenyl-sulphonylcarboxamides are similarly prepared from the corresponding carboxylic acid and the alkyl- or alkenyl-sulphonamide by dehydration with standard peptide coupling agents such as 1,1'-carbonyldiimidazole (P. L. Ornstein et al, J. Med. Chem., 1996, 39 (11), 2232).

The hydroxamic acid groups are prepared from the corresponding acids by standard amide coupling reactions e.g. N. R. Patel et al, Tetrahedron, 1987, 43 (22), 5375.

2,4-Thiazolidinedione groups may prepared from the aldehydes by condensation with 2,4-thiazolidinedione and subsequent removal of the olefinic double bond by hydrogenation.

The preparation of 5-oxo-1,2,4-oxadiazoles from nitriles is decribed by Y. Koharau et al, Bioorg. Med. Chem. Lett., 1995, 5 (17), 1903.

1,2,4-Triazol-5-yl groups may be prepared from the corresponding nitrile by reaction with an alcohol under acid conditions followed by reaction with hydrazine and then an $R^{10}$-substituted activated carboxylic acid (see J. B. Polya in "Comprehensive Heterocyclic Chemistry" Edition 1, p 762, Ed A. R. Katritzky and C. W. Rees, Pergamon Press, Oxford, 1984 and J. J. Ares et al, J. Heterocyclic Chem., 1991, 28(5), 1197).

Other substituents on $R^3$ alkyl or alkenyl may be interconverted by conventional methods, for example hydroxy may be derivatised by esterification, acylation or etherification. Hydroxy groups may be converted to halogen, thiol, alkylthio, azido, alkylcarbonyl, amino, aminocarbonyl, oxo, alkylsulphonyl, alkenylsulphonyl or aminosulphonyl by conversion to a leaving group and substitution by the required group or oxidation as appropriate or reaction with an activated acid, isocyanate or alkoxyisocyanate. Primary and secondary hydroxy groups can be oxidised to an aldehyde or ketone respectively and alkylated with a suitable agent such as an organometallic reagent to give a secondary or tertiary alcohol as appropriate. A carboxylate group may be converted to an hydroxymethyl group by reduction of an ester of this acid with a suitable reducing agent such as lithium aluminium hydride.

An $NH_2$ substituent on piperidine is converted to $NR^2R^4$ by conventional means such as amide or sulphonamide formation with an acyl derivative $R^5COW$ or $R^5SO_2W$, for compounds where U is CO or $SO_2$ or, where U is $CH_2$, by alkylation with an alkyl halide $R^5CH_2$-halide in the presence of base, acylation/reduction with an acyl derivative $R^5COW$ or reductive alkylation with an aldehyde $R^5CHO$.

Where one of $R^3$ and $R^6$, $R^7$, $R^8$ or $R^9$ contains a carboxy group and the other contains a hydroxy or amino group they may together form a cyclic ester or amide linkage. This linkage may form spontaneously during coupling of the compound of formula (IV) and the piperidine moiety or in the presence of standard peptide coupling agents.

It will be appreciated that under certain circumstances interconversions may interfere, for example, A or B hydroxy groups in A or B and the piperidine substituent $NH_2$ will require protection e.g. as a carboxy- or silyl-ester group for hydroxy and as an acyl derivative for piperidine $NH_2$, during conversion of $R^{1'}$, $R^{2'}$, $R^{3'}$ or $R^{4'}$, or during the coupling of the compounds of formulae (IV) and (V).

Compounds of formulae (IV) and (V) are known compounds, (see for example Smith et al, *J. Amer. Chem. Soc.*, 1946, 68, 1301) or prepared analogously.

Compounds of formula (IV) where X is $CR^6R^7SO_2W$ may be prepared by a route analogous to that of Ahmed El Hadri et al, *J. Heterocyclic Chem.*, 1993, 30 (3), 631. Thus compounds of formula (IV) where X is $CH_2SO_2OH$ may be prepared by reacting the corresponding 4-methyl compound with N-bromosuccinimide, followed by treatment with sodium sulfite. The leaving group W may be converted to another leaving group W, e.g. a halogen group, by conventional methods.

The isocyanate of formula (IV) may be prepared conventionally from a 4-amino derivative such as 4-amino-quinoline, and phosgene, or phosgene equivalent (eg triphosgene) or it may be prepared more conveniently from a 4-carboxylic acid by a "one-pot" Curtius Reaction with diphenyl phosphoryl azide (DPPA) [see T. Shiori et al. *Chem. Pharm. Bull.* 35, 2698-2704 (1987)].

The 4-amino derivatives are commercially available or may be prepared by conventional procedures from a corresponding 4-chloro or 4-trifluoromethanesulphonate derivative by treatment with ammonia (O. G. Backeberg et. al., *J. Chem Soc.*, 381, 1942) orpropylamine hydrochloride (R. Radinov et. al., Synthesis, 886, 1986).

4-Alkenyl compounds of formula (IV) may be prepared by conventional procedures from a corresponding 4-halogeno-derivative by e.g. a Heck synthesis as described in e.g. *Organic Reactions*, 1982, 27, 345.

4-Halogeno derivatives of compounds of formula (IV) are commercially available, or may be prepared by methods known to those skilled in the art. A 4-chloroquinoline is prepared from the corresponding quinolin-4-one by reaction with phosphorus oxychloride ($POCl_3$) or phosphorus pentachloride, $PCl_5$. A 4-chloroquinazoline is prepared from the corresponding quinazolin-4-one by reaction with phosphorus oxychloride ($POCl_3$) or phosphorus pentachloride, $PCl_5$. A quinazolinone and quinazolines may be prepared by standard routes as described by T. A. Williamson in *Heterocyclic Compounds*, 6, 324 (1957) Ed. R. C. Elderfield.

4-Carboxy derivatives of compounds of formula (I) are commercially available or may be prepared by conventional procedures for preparation of carboxy heteroaromatics well known to those skilled in the art. For example, quinazolines may be prepared by standard routes as described by T. A. Williamson in *Heterocyclic Compounds*, 6, 324 (1957) Ed. R. C. Elderfield. These 4-carboxy derivatives may be activated by conventional means, e.g. by conversion to an acyl halide or anhydride.

Pyridazines may be prepared by routes analogous to those described in Comprehensive Heterocyclic Chemistry, Volume 3, Ed A. J. Boulton and A. McKillop and napthyridines may be prepared by routes analogous to those described in Comprehensive Heterocyclic Chemistry, Volume 2, Ed A. J. Boulton and A. McKillop.

A 4-oxirane derivative of compounds of formula (IV) is conveniently prepared from the 4-carboxylic acid by first conversion to the acid chloride with oxalyl chloride and then reaction with trimethylsilyldiazomethane to give the diazoketone derivative. Subsequent reaction with 5M hydrochloric acid gives the chloromethylketone. Reduction with sodium borohydride in aqueous methanol gives the chlorohydrin which undergoes ring closure to afford the epoxide on treatment with base, e.g. potassium hydroxide in ethanol-tetrahydrofuran.

Alternatively and preferably, 4-oxirane derivatives can be prepared from bromomethyl ketones which can be obtained from 4-hydroxy compounds by other routes well known to those skilled in he art. For example, hydroxy compounds can be converted to the corresponding 4-trifluoromethanesulphonates by reaction with trifluoromethanesulphonic anhydride under standard conditions (see K. Ritter, Synthesis, 1993, 735). Conversion into the corresponding butyloxyvinyl ethers can be achieved by a Heck reaction with butyl vinyl ether under palladium catalysis according to the procedure of W. Cabri et al, J. Org. Chem, 1992, 57 (5), 1481. (Alternatively, the same intermediates can be attained by Stille coupling of the trifluoromethanesulphonates or the analaogous chloro derivatives with (1-ethoxyvinyl)tributyl tin, T. R. Kelly, J. Org. Chem., 1996, 61, 4623.) The alkyloxyvinyl ethers are then converted into the corresponding bromomethylketones by treatment with N-bromosuccinimide in aqueous tetrahydrofuran in a similar manner to the procedures of J. F. W. Keana, J. Org. Chem., 1983, 48, 3621 and T. R. Kelly, J. Org. Chem., 1996, 61, 4623.

The 4-hydroxy derivatives can be prepared from an amino aromatic by reaction with methylpropiolate and subsequent cyclisation, analogous to the method described in N. E. Heindel et al, J. Het. Chem., 1969, 6, 77. For example, 5-amino-2-methoxy pyridine can be converted to 4-hydroxy-6-methoxy-[1,5]naphthyridine using this method.

If a chiral reducing agent such as (+) or (−)-B-chlorodi-isopinocamphenylborane ['DIP-chloride'] is substituted for sodium borohydride, the prochiral chloromethylketone is converted into the chiral chlorohydrin with ee values generally 85-95% [see C. Bolm et al, *Chem. Ber.* 125, 1169-1190, (1992)]. Recrystallisation of the chiral epoxide gives material in the mother liquor with enhanced optical purity (typically ee 95%).

The (R)-epoxide, when reacted with a piperidine derivative gives ethanolamine compounds as single diastereomers with (R)-stereochemistry at the benzylic position.

Alternatively, the epoxide may be prepared from the 4-carboxaldehyde by a Wittig approach using trimethylsulfonium iodide [see G. A. Epling and K-Y Lin, *J. Het. Chem.*, 1987, 24, 853-857], or by epoxidation of a 4-vinyl derivative.

4-Hydroxy-1,5-naphthyridines can be prepared from 3-aminopyridine derivatives by reaction with diethyl ethoxymethylene malonate to produce the 4-hydroxy-3-carboxylic acid ester derivative with subsequent hydrolysis to the acid, followed by thermal decarboxylation in quinoline (as for example described for 4-Hydroxy-[1,5]naphthyridine-3-carboxylic acid, J. T. Adams et al., *J. Amer. Chem. Soc.*, 1946, 68, 1317). A 4-hydroxy-[1,5]naphthyridine can be converted to the 4-chloro derivative by heating in phosphorus oxychlo'ride, or to the 4-methanesulphonyloxy or 4-trifluoromethanesulphonyloxy derivative by reaction with methanesulphonyl chloride or trifluoromethanesulphonic anhydride, respectively, in the presence of an organic base. A 4-amino 1,5-naphthyridine can be obtained from the 4-chloro derivative by reaction with n-propylamine in pyridine.

Similarly, 6-methoxy-1,5-naphthyridine derivatives can be prepared from 3-amino-6-methoxypyridine.

1,5-Naphthyridines may be prepared by other methods well known to those skilled in the art (for examples see P. A. Lowe in "Comprehensive Heterocyclic Chemistry" Volume 2, p 581-627, Ed A. R. Katritzky and C. W. Rees, Pergamon Press, Oxford, 1984).

The 4-hydroxy and 4-amino-cinnolines may be prepared following methods well known to those skilled in the art [see A. R. Osborn and K. Schofield, *J. Chem. Soc.* 2100 (1955)]. For example, a 2-aminoacetopheneone is diazotised with sodium nitrite and acid to produce the 4-hydroxycinnoline with conversion to chloro and amino derivatives as described for 1,5-naphthyridines.

For compounds of formula (V), suitable amines may be prepared from the corresponding 4-substituted piperidine acid or alcohol. In a first instance, an N-protected piperidine containing an acid bearing substituent, can undergo a Curtius rearrangement and the intermediate isocyanate can be converted to a carbamate by reaction with an alcohol. Conversion to the amine may be achieved by standard methods well known to those skilled in the art used for amine protecting group removal. For example, an acid substituted N-protected piperidine can undergo a Curtius rearrangement e.g. on treatment with diphenylphosphoryl azide and heating, and the intermediate isocyanate reacts in the presence of 2-trimethylsilylethanol to give the trimethylsilylethylcarbamate (T. L. Capson & C. D. Poulter, *Tetrahedron Lett.*, 1984, 25, 3515). This undergoes cleavage on treatment with tetrabutylammonium fluoride to give the 4-amine substituted N-protected piperidine.

In a second instance, an N-protected piperidine containing an alcohol bearing substituent undergoes a Mitsunobu reaction (for example as reviewed in Mitsunobu, *Synthesis*, (1981), 1), for example with succinimide in the presence of diethyl azodicarboxylate and triphenylphosphine to give the phthalimidoethylpiperidine. Removal of the phthaloyl group, for example by treatment with methylhydrazine, gives the amine of formula (V).

$R^5CH_2$-halides, acyl derivative $R^5COW$ and $R^5SO_2W$ or aldehydes $R^5CHO$ are commercially available or are prepared conventionally. The aldehydes may be prepared by partial reduction of the $R^5$-ester with lithium aluminium hydride or di-isobutylaluminium hydride or more preferably by reduction to the alcohol, with lithium aluminium hydride or sodium borohydride or lithium triethylborohydride (see *Reductions by the Alumino-and Borohydrides in Organic Synthesis*, 2nd ed., Wiley, N.Y., 1997; *JOC*, 3197, 1984; *Org. Synth. Coll.*, 102, 1990; 136, 1998; *JOC*, 4260, 1990; *TL*, 995, 1988; *JOC*, 1721, 1999; *Liebigs Ann./Recl.*, 2385, 1997; *JOC*, 5486, 1987), followed by oxidation to the aldehyde with manganese (II) dioxide. The aldehydes may also be prepared from carboxylic acids in two stages by conversion to a mixed carbonate for example by reaction with isobutyl chloroformate followed by reduction with sodium borohydride (R. J. Alabaster et al., Synthesis, 598, 1989) to give the hydroxymethyl substituted heteroaromatic or aromatic and then oxidation with a standard oxidising agent such as pyridinium dichromate or manganese (D) dioxide. Acyl derivative $R^5COW$ may be prepared by activation of the $R^5$-ester. $R^5CH_2$-halides such as bromides may be prepared from the alcohol $R^5CH_2OH$ by reaction with phosphorus tribromide in DCM/triethylamine.

Alternatively the aldehyde $R^5CHO$ and sulphonic acid derivative $R^5SO_2W$ may be generated by treatment of the $R^5H$ heterocycle with suitable reagents. For example benzoxazinones, or more preferably their N-methylated derivatives can be formylated with hexamine in either trifluoroacetic acid or methanesulfonic acid, in a modified Duff procedure [O. I. Petrov et al. *Collect. Czech. Chem. Commun.* 62, 494-497 (1997)]. 4 Methyl-4H-benzo[1,4]oxazin-3-one may also be formylated using dichloromethyl methyl ether and aluminium chloride giving exclusively the 6-formyl derivative. Reaction of a $R^5H$ heterocycle with chlorosulphonic acid gives the sulphonic acid derivative (by methods analogous to Techer et. al., *C. R. Hebd. Seances Acad. Sci. Ser. C;* 270, 1601, 1970).

The aldehyde $R^5CHO$ may be generated by conversion of an $R^5$halogen or $R^5$trifluoromethane sulphonyloxy derivative into an olefin with subsequent oxidative cleavage by standard methods. For example, reaction of a bromo derivative under palladium catalysis with trans-2-phenylboronic acid under palladium catalysis affords a styrene derivative which upon ozonolysis affords the required $R^5CHO$ (Stephenson, G. R., Adv. Asymmetric Synth. (1996), 275-298. Publisher: Chapman & Hall, London).

$R^5$ heterocycles are commercially available or may be prepared by conventional methods. For example where a benzoxazinone is required, a nitrophenol may be alkylated with for example ethyl bromoacetate and the resulting nitro ester reduced with Fe in acetic acid (alternatively Zn/AcOH/HCl or $H_2$ Pd/C or $H_2$ Raney Ni). The resulting amine will undergo spontaneous cyclisation to the required benzoxazinone. Alternatively a nitrophenol may be reduced to the aminophenol, which is reacted with chloroacetyl chloride [method of X. Huang and C. Chan, *Synthesis* 851 (1994)] or ethyl bromoacetate in DMSO [method of Z. Moussavi et al. *Eur. J. Med. Chim. Ther.* 24, 55-60 (1989)]. The same general routes can be applied to prepare benzothiazinones [See for example F. Eiden and F. Meinel, Arch. Pharm. 312, 302-312 (1979), H. Fenner and R Grauert *Liebigs. Ann. Chem.* 193-313 (1978)]]. A variety of routes are available to prepare aza analogues of benzothiazinones via the key corresponding aldehydes. For instance, 2-oxo-2,3-dihydro-1H-pyrido[3,4-b][1,4]thiazine-7-carbaldehyde may be accessed from 5-fluoro-2-picoline (E. J. Blanz, F. A. French, J. R. DoAmaral and D. A. French, J. Med. Chem. 1970, 13, 1124-1130) by constructing the thiazinone ring onto the pyridyl ring then functionalising the methyl substituent. The dioxin analogue of this aza substitution pattern, 2,3-dihydro-[1,4]dioxino[2,3-c]pyridine-7-carbaldehyde is accessible from Kojic acid by aminolysis from pyrone to pyridone then annelating the dioxin ring, as described in the subsequent experimental data. Other aza substitution patterns with pyridothiazin-3-one, pyridooxazin-3-one, and pyridodioxin ring systems are also accessible by analogous methods. Ortho-aminothiophenols may be conveniently prepared and reacted as their zinc complexes [see for example V. Taneja et al *Chem. Ind.* 187 (1984)]. Benzoxazolones may be prepared from the corresponding aminophenol by reaction with carbonyl diimidazole, phosgene ot triphosgene. Reaction of benzoxazolones with diphosporus pentasulfide affords the corresponding 2-thione. Thiazines and oxazines can be prepared by reduction of the corresponding thiazinone or oxazinone with a reducing agent such as lithium aluminium hydride.

The amines $R^{2'}R^{4'}NH$ are available commercially or prepared conventionally. For example amines $R^5CH_2NH_2$ may be prepared from a bromomethyl derivative by reaction with sodium azide in dimethylformamide (DMF), followed by hydrogenation of the azidomethyl derivative over palladium-carbon. An alternative method is to use potassium phthalimide/DMF to give the phthalimidomethyl derivative, followed by reaction with hydrazine in DCM to liberate the primary amine.

Conversions of $R^{1a'}$, $R^{1'}$, $R^{2'}$, $R^{3'}$ and $R^{4'}$ may be carried out on the intermediates of formulae (IV), and (V) prior to their reaction to produce compounds of formula (I) in the same way as described above for conversions after their reaction.

Further details for the preparation of compounds of formula (I) are found in the examples.

The compounds of formula (I) may be prepared singly or as compound libraries comprising at least 2, for example 5 to 1,000 compounds, and more preferably 10 to 100 compounds of formula (I). Libraries of compounds of formula (I) may be prepared by a combinatorial "split and mix" approach or by multiple parallel synthesis using either solution phase or solid phase chemistry, by procedures known to those skilled in the art.

Thus according to a further aspect of the invention there is provided a compound library comprising at least 2 compounds of formula (I) or pharmaceutically acceptable derivatives thereof.

Novel intermediates of formulae (IV) and (V) are also part of this invention.

The antibacterial compounds according to the invention may be formulated for administration in any convenient way for use in human or veterinary medicine, by analogy with other antibacterials.

The pharmaceutical compositions of the invention include those in a form adapted for oral, topical or parenteral use and may be used for the treatment of bacterial infection in mammals including humans.

The composition may be formulated for administration by any route. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 50-500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (I) or a pharmaceutically acceptable derivative thereof is administered in the above-mentioned dosage range.

The compound of formula (I) may be the sole therapeutic agent in the compositions of the invention or a combination with other antibacterials. If the other antibacterial is a β-lactam then a β-lactamase inhibitor may also be employed.

Compounds of formula (I) are active against a wide range of organisms including both Gram-negative and Gram-positive organisms.

All publications, including but not limited to patents and patent applications, cited in this specification are herein incorporated by reference as if each individual publication were specifically and individually indicated to be incorporated by reference herein as though fully set forth.

The following examples illustrate the preparation of certain compounds of formula (I) and the activity of certain compounds of formula (I) against various bacterial organisms.

Abbreviations in the examples:
RT=room temperature
ES=Electrospray mass spec.
LCMS=Liquid chromatography mass spec.
APCI+=Atmospheric pressure chemical ionisation mass spec
DCM=dichloromethane
DMF=dimethylformamide
THF=tetrahydrofuran

EXAMPLES

Example 1

6-({2S,4S}-1-[(R)-2-Hydroxy-2-(6-methoxy-[1,5]naphthyridin-4-yl)ethyl]-2-(trifluoromethyl)piperidin-4-ylamino}methyl)-4H-benzo[1,4]thiazin-3-one

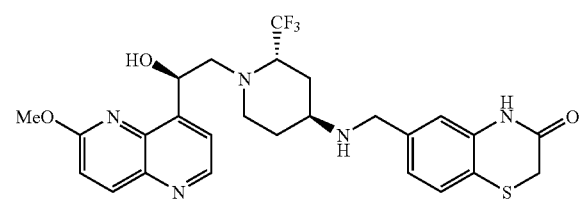

(a) (1-(R)-Phenylethyl)-(2,2,2-trifluoroethylidene) amine

To solution of (trifluoromethyl)acetaldehyde ethyl hemiacetal (1.2 equiv.) in toluene is added (R)-(+)-α-methylbenzylamine (1 equiv.) and catalytic amount of p-toluenesulfonic acid. The solution is heated at reflux under a Dean-Stark apparatus. After 3 hr, the reaction flask is fitted with a short-path condenser and the reaction contents were fractionally distilled to give the title compound as a colorless oil.

(b) 1-[1-(R)-Phenylethyl]-2-(S)-(trifluoromethyl)-2,3-dihydro-1H-pyridin-4-one and 1-[1-(R)-phenylethyl]-2-(R)-(trifluoromethyl)-2,3-dihydro-1H-pyridin-4-one To a suspension of $ZnCl_2$ (1.1 equiv.) in acetonitrile at −50° C. is added (1-(R)-phenylethyl)-(2,2,2-trifluoroethylidene) amine (1a) (1.0 equiv.). After 5 min, 1-methoxy-3-(trimethylsilyloxy)-1,3-butadiene (Danishefsky's diene, 1.1 equiv.) is added and stirring is continued for 14 hrs at −50° C. The reaction is warmed to RT, poured onto $H_2O$ and extracted with $CH_2Cl_2$. The combined organic fractions are washed with 1 M HCl, dried over $Na_2SO_4$ and concentrated. Purification by flash chromatography on silica gel affords the title compounds.

(c) 1-[(R)-1-Phenylethyl]-2-(S)-(trifluoromethyl) piperidin-4-one

To a solution of 1-[1-(R)-1-phenylethyl]-2-(S)-(trifluoromethyl)-2,3-dihydro-1H-pyridin-4-one (1b) (1 equiv.) at −78° C. in THF is added L-Selectride® (lithium tri-sec-butylborohydride) (1.3 equiv.) dropwise. After 2 hrs, the reaction is quenched with $H_2O$ and EtOAc is added. The organic layer is separated, washed with saturated aqueous $NaHCO_3$ and brine, and dried over $Na_2SO_4$. Purification by flash chromatography on silica gel affords the title compound.

1-[1-(R)-phenylethyl]-2-(R)-(trifluoromethyl)-2,3-dihydro-1H-pyridin-4-one is processed similarly to afford 1-[(R)-1-phenylethyl]-2-(R)-(trifluoromethyl)piperidin-4-one.

(d) ([1-(R)-Phenylethyl]-(2S,4S)-2-(trifluoromethyl) piperidin-4-yl)carbamic acid tert-butyl Ester and ([1-(R)-Phenylethyl]-(2S,4R)-2-(trifluoromethyl) piperidin-4-yl)carbamic acid tert-butyl ester To a solution of methoxylamine (2 equiv.) in toluene is added 1-[(R)-1-phenylethyl]-2-(S)-(trifluoromethyl)piperidin-4-one (1c) (1 equiv.) and a catalytic amount of p-toluenesulfonic acid. After 3 hrs at reflux, the solution is cooled to RT and washed with 10% aqueous $NaHCO_3$ solution. The toluene solution is then dried over $Na_2SO_4$ and concentrated to an oil. This oil (the O-methyloxime) is dissolved in THF and the solution is cooled to 0° C. A solution of $LiAlH_4$ (2 equiv.) in THF is added dropwise and the reaction is heated at 50° C. with for 24 hrs. After cooling to RT, the reaction is quenched under basic conditions and extracted with $CH_2Cl_2$. The organic fractions are dried over $Na_2SO_4$ and concentrated under vacuum. The resulting residue (the crude amine) is dissolved in dry THF at RT, and di-tert-butyl dicarbonate (1.5 equiv.) is added. After 12 hrs, the reaction solution is concentrated and the remaining residue is purified by flash chromatography on silica gel to afford the title compounds.

1-[(R)-1-phenylethyl]-2-(R)-(trifluoromethyl)piperidin-4-one is processed similarly to afford ([1-(R)-Phenylethyl]-(2R,4S)-2-(trifluoromethyl)piperidin-4-yl)carbamic acid tert-butyl ester and ([1-(R)-Phenylethyl]-(2R,4R)-2-(trifluoromethyl)piperidin-4-yl)carbamic acid tert-butyl ester (e) ((2S,4S)-2-(trifluoromethyl)piperidin-4-yl) carbamic acid tert-butyl ester.

The major diastereomer ([1-(R)-Phenylethyl]-(2S,4S)-2-(trifluoromethyl)piperidin-4-yl)carbamic acid tert-butyl ester, from step (d), is dissolved in ethanol and a catalytic amount of 10% Pd/C is added. The reaction is shaken under $H_2$ (50 psi) on a Parr hydrogenator apparatus. After 6 hrs the mixture is filtered through celite® filter medium, and the filter pad is washed with ethanol. The filtrate is concentrated under vacuum to give the title compound.

The other diastereomers from (d) are processed similarly to afford the following products:
((2S,4R)-2-(trifluoromethyl)piperidin-4-yl)carbamic acid tert-butyl ester ((2R,4S)-2-(trifluoromethyl)piperidin-4-yl)carbamic acid tert-butyl ester
((2R,4R)-2-(trifluoromethyl)piperidin-4-yl)carbamic acid tert-butyl ester

(f) 4-Hydroxy-6-methoxy-[1,5]-naphthyridine

5-Amino-2-methoxypyridine (55 g, 0.44 mol) in methanol (1000 ml) with methyl propiolate (40 ml, 0.44 mol) was stirred for 48 hours, then evaporated and the product purified by chromatography on silica gel (dichloromethane) followed by recrystallisation from dichloromethane-hexane (44.6 g, 48%).

The unsaturated ester (10.5 g, 0.05 mol) in warm Dowtherm A (50 ml) was added over 3 minutes to refluxing Dowtherm A, and after a further 20 minutes at reflux the mixture was cooled and poured into ether. The precipate was filtered to give the title compound (6.26 g, 70%).

(g) Bromomethyl-(6-methoxy-[1,5]-naphthyridin-4-yl)-ketone

The naphthyridine (1f) (10 g, 0.057 mol) in dichloromethane (200 ml) containing 2,6-lutidine (9.94 ml, 0.086 mol) and 4-dimethylaminopyridine (0.07 g, 0.0057 mol) was cooled in ice and treated with trifluoromethanesulfonic anhydride (10.5 ml, 0.063 mol). After stirring for 2.5 hours the mixture was washed with saturated ammonium chloride solution, dried, evaporated and purified on silica (dichloromethane). The triflate (13.2 g, 0.044 mol) in DMF (200 ml) with triethylamine (12 ml, 0.086 mol) butyl vinyl ether (22 ml, 0.17 mol), palladium (II) acetate (0.97 g, 0.0044 mol) and 1,3-bis(diphenylphosphino)propane (1.77 g, 0.0044 mol) was heated at 60° C. for 3 hours then evaporated and chromatographed on silica gel (dichloromethane) to give a yellow solid (10.7 g, 95%). This was dissolved in THF (250 ml), water (40 ml) and treated with N-bromosuccinimide (7.4 g. 0.042 mol) for 1 hour, then evaporated and chromatographed on silica gel (dichloromethane) to give the ketone (10.42 g, 98%).

(h) (R)-2-Bromo-1-(6-methoxy-[1,5]-naphthyridin-4-yl)ethanol

The ketone (1 g) (6.6 g, 0.023 mol) in toluene was treated with (+)-B-chlorodiisopinocamphenylborane ((+)-DIP-chloride) (12 g, 0.037 mol) and stirred overnight, then diethanolamine (15 g, 0.14 mol) added and the mixture stirred for 3 hours, filtered and evaporated. Chromatography on silica gel (ethyl acetate-hexane) gave a white solid (4.73 g, 73%).

(i) (R)-2-(6-Methoxy-[1,5]-naphthyridin-4-yl)oxirane

The alcohol (1 h) (4.8 g, 0.017 mol) in methanol (20 ml) was stirred with potassium carbonate (2.6 g, 0.019 mol) for 1 hour, then evaporated and chromatographed on silica gel (ethyl acetate-hexane-dichloromethane) to give a solid (3.14 g, 92%), (91% ee by chiral HPLC).
MS (+ve ion electrospray) m/z 203 (NH+).

(j) {(2S,4S)-[(R)-hydroxy-(6-methoxy-[1,5]naphthyridin-4-yl)ethyl]-2-(trifluoromethyl)piperidin-4-yl}carbamic acid tert-butyl ester To a solution of 6-methoxy-4(R)-oxiranyl-[1,5]naphthyridine (1i)(1 equiv.) and LiClO$_4$ (1 equiv.) in DMF is added ((2S,4S)-2-(trifluoromethyl)piperidin-4-yl) carbamic acid tert-butyl ester (1e) (1 equiv.). The reaction solution is heated to 70° C. for 18 hrs and then cooled to RT and concentrated under vacuum. Purification by flash chromatography on silica gel affords the title compound as a single stereoisomer.

(k) (R)-2-((2S,4S)-4-amino-2-(trifluoromethyl)piperidin-1-yl)-1-(6-methoxy-[1,5]naphthyridin-4-yl)ethanol {(2S,4S)-[(R)-hydroxy-(6-methoxy-[1,5]naphthyridin-4-yl)ethyl]-2-(trifluoromethyl)piperidin-4-yl}carbamic acid tert-butyl ester (1j) is dissolved in CH$_2$Cl$_2$ and TFA (1:1, v/v). After 2 hrs, the solution is concentrated to dryness under vacuum and the residue is redissolved in 4 M HCl in dioxane. After 30 min, the slurry is triturated with Et$_2$O and filtered. The solid is dissolved in H$_2$O and the solution is made basic with aqueous NaOH. The basic aqueous solution is concentrated to dryness under vacuum and the residue is dried under high vacuum. The resulting solid is extracted with CH$_2$Cl$_2$/MeOH (10:1, v/v), and the combined extracts are concentrated and dried under high vacuum to give the title compound.

The other 3 stereoisomers described in step (e) are processed similarly (steps (j) and k)) to afford the following products:
(R)-2-((2S,4R)-4-amino-2-(trifluoromethyl)piperidin-1-yl)-1-(6-methoxy-[1,5]naphthyridin-4-yl)ethanol
(R)-2-((2R,4S)-4-amino-2-(trifluoromethyl)piperidin-1-yl)-1-(6-methoxy-[1,5]naphthyridin-4-yl)ethanol and
(R)-2-((2R,4R)-4-amino-2-(trifluoromethyl)piperidin-1-yl)-1-(6-methoxy-[1,5]naphthyridin-4-yl)ethanol

(l) 3-Oxo-3,4-dihydro-2H-benzo[1,4]thiazine-6-carboxylic Acid

3-Oxo-3,4-dihydro-2H-benzo[1,4]thiazine-6-carboxylic acid methyl ester (6.74 g) was suspended in tetrahydrofuran (100 ml) and 2M sodium hydroxide (30 ml) was added followed by water (20 ml). The solution was stirred for 2.5 hours, evaporated to half volume and acidified with 2M hydrochloric acid. The product was collected, washed with water and dried in vacuo, to give a white solid (6.2 g).
MS (−ve ion electrospray) m/z 208 (M−H)−

(m) 6-Hydroxymethyl-4H-benzo[1,4]thiazin-3-one

The acid (6a) in tetrahydrofuran (50 ml) and triethylamine (4.7 ml) was cooled to 0° C. and isobutylchloroformate (4.02 ml) was added dropwise and the solution was stirred at 0° C. for 2 hours, when it was filtered into a stirred solution of sodium borohydride (3.14 g) in ice/water (50 ml). The mixture was stirred at 0° C. for 1 hour and allowed to warm to room temperature. It was acidified with 2M hydrochloric acid, evaporated to half volume, and the resulting product was collected, washed with water and dried in vacuo, to give a white solid (4.5 g).
MS (−ve ion electrospray) m/z 194 (M−H)−

(n) 3-Oxo-3,4-dihydro-2H-benzo[1,4]thiazine-6-carboxaldehyde

A stirred solution of the alcohol (6b) (3.5 g) in chloroform (150 ml) and tetrahydrofuran (300 ml) was treated with manganese dioxide (7.8 g) for 18 hours and was filtered and evaporated to give a white solid (2.5 g).
MS (−ve ion electrospray) m/z 194 (M−H)−

(o) 6-({2S,4S)-1-[(R)-2-Hydroxy-2-(6-methoxy-[1,5]naphthyridin-4-yl)ethyl ]-2-(trifluoromethyl)piperidin-4-ylamino}methyl)-4H-benzo[1,4]thiazin-3-one (Title Compound)

To a solution of (R)-2-((2S,4S)-4-amino-2-(trifluoromethyl)piperidin-1-yl)-1-(6-methoxy-[1,5]naphthyridin-4-yl) ethanol (1k) (1 equiv.) in acetonitrile is added Na$_2$SO$_4$ and 3-oxo-3,4-dihydro-2H-benzo[1,4]thiazine-6-carboxaldehyde (in) (1 equiv.). After 12 hr at RT, the reaction is filtered through a sintered-glass funnel and the filtrate is concentrated under vacuum. To the remaining residue is added EtOH and NaBH$_4$ (1 equiv.). After 12 h, the reaction is concentrated. The residue is dissolved in 6 N HCl, then the solution is neutralized with 6 N NaOH and extracted with EtOAc. The combined organic layers are dried over Na$_2$SO$_4$ and concentrated under vacuum. The crude product is purified by chromatography on silica gel to afford the title compound.

Example 2

6-({(3R,4S)-1-[(R)-2-Hydroxy-2-(6-methoxy-[1,5] naphthyridin-4-yl)ethyl]-3-(trifluoromethyl)piperidin-4-ylamino}methyl)-4H-benzo[1,4]thiazin-3-one

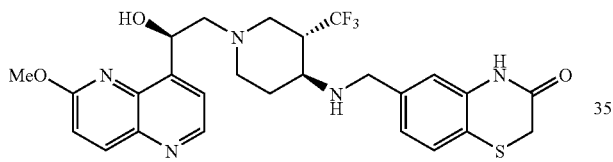

(a) 4-(Trimethylsilyloxy)-3,6-dihydro-2H-pyridine-1-carboxylic Acid tert-Butyl Ester To a solution of 4-oxo-piperidine-1-carboxylic acid tert-butyl ester (1 equiv.) in DMF is added TMSCl (1.5 equiv.) and triethylamine (1.5 equiv.) and the reaction solution is heated at 80° C. After 3 hrs the reaction is allowed to cool to RT and the DMF is removed in vacuo. The remaining residue is dissolved in CH$_2$Cl$_2$ and the solution is washed with 10% NaHCO$_3$, dried over Na$_2$SO$_4$, and concentrated to afford the crude title compound. This is used without further purification.

(b) (±)-4-Oxo-3-(trifluoromethyl)piperidine-1-carboxylic acid tert-butyl ester

To a solution of 4-(trimethylsilyloxy)-3,6-dihydro-2H-pyridine-1-carboxylic acid tert-butyl ester (2a) (1 equiv.) in DMF is added pyridine (1 equiv.) and (trifluoromethyl) dibenzothiophenium triflate (1 equiv.). The reaction is heated at 80° C. overnight and then is cooled to RT and concentrated in vacuo. The reaction solution is washed with 1 N HCl, then with H$_2$O, dried over Na$_2$SO$_4$ and concentrated under vacuum. Purification by flash chromatography on silica gel affords the title compound.

(c) (3R,4S)-4-((R)-1-phenylethylamino)-3-(trifluoromethyl)piperidine-1-carboxylic Acid tert-Butyl Ester To a solution of (±)-4-oxo-3-(trifluoromethyl)piperidine-1-carboxylic acid tert-butyl ester (2b) (1 equiv.) in toluene is added (R)-(+)-α-methylbenzylamine (1 equiv.) and catalytic amount of p-toluenesulfonic acid. The solution is heated to reflux under a Dean-Stark apparatus. After 12 hr, the reaction is cooled to RT, washed with 10% aqueous NaHCO$_3$, dried over Na$_2$SO$_4$, and concentrated in vacuo. The residue is dissolved in EtOH and NaBH$_4$ (1 equiv.) is added. After 12 h, the reaction is concentrated and the residue is dissolved in 1 N HCl. The solution is neutralized with 6 N NaOH and extracted with EtOAc. The organic fraction is dried over Na$_2$SO$_4$ and concentrated under vacuum. The crude product is purified by chromatography on silica gel to afford the title compound. The three other diastereomers are also separated.

(d) (3R,4S)-4-amino-3-(trifluoromethyl)piperidine-1-carboxylic acid tert-butyl ester To a solution of (3R,4S)-4-((R)-1-phenylethylamino)-3-(trifluoromethyl)piperidine-1-carboxylic acid tert-butyl ester (2c) (1 equiv.) in ethanol in a Parr flask is added 10% Pd/C and the reaction is shaken under H$_2$ (50 psi) for 6 hrs. The mixture is then filtered through celites and the filter pad is washed with EtOH. The filtrate is concentrated to give the title compound.

(e) (3R,4S)-4-[(3-oxo-3,4-dihydro-2H-benzo-[1,4] thiazin-6-ylmethyl)amino]-3-(trifluoromethyl)piperidine-1-carboxylic Acid tert-Butyl Ester To a solution of (3R,4S)-4-amino-3-(trifluoromethyl)piperidine-1-carboxylic acid tert-butyl ester (2d) (1 equiv.) in acetonitrile is added Na$_2$SO$_4$ and 3-oxo-3,4-dihydro-2H-benzo[1,4]thiazine-6-carboxaldehyde (in) (1 equiv.). After 12 hr at RT, the reaction is filtered through a sintered-glass funnel and the filtrate is concentrated under vacuum. The remaining residue is dissolved in EtOH and NaBH$_4$ (1 equiv.) is added. After 12 h, the reaction is concentrated and the residue is dissolved in 1 N HCl. The solution is neutralized with 6 N NaOH and extracted with EtOAc. The organic fraction is dried over Na$_2$SO$_4$ and concentrated under vacuum. The crude product is purified by flash chromatography on silica gel to afford the title compound.

(f) 6-[((3R,4S)-3-(trifluoromethyl)piperidin-4-ylamino)methyl]-4H-benzo[1,4]thiazin-3-one (3R,4S)-4-[(3-oxo-3,4-dihydro-2H-benzo-[1,4]thiazin-6-ylmethyl)amino]-3-(trifluoromethyl)piperidine-1-carboxylic acid tert-butyl ester (2e) (1 equiv.) is dissolved in CH$_2$Cl$_2$ and TFA (1:1, v/v). After 2 hrs, the solution is concentrated to dryness under vacuum and the residue is dissolved in 4 M HCl in dioxane. After 30 min, the slurry is triturated with Et$_2$O and filtered. The solid is dissolved in H$_2$O and the solution is made basic with aqueous NaOH. The basic aqueous solution is concentrated under vacuum and the residue is dried under high vacuum. The resulting solid is extracted with CH$_2$Cl$_2$/MeOH (10:1, v/v) and the solution is concentrated. The residue is dried under high vacuum to give the title compound.

(g) 6-({(3R,4S)-1-[(R)-2-Hydroxy-2-(6-methoxy-[1,5]naphthyridin-4-yl)ethyl]-3-(trifluoromethyl)piperidin-4-ylamino}methyl)-4H-benzo[1,4]thiazin-3-one (Title Compound)

To a solution of 6-methoxy-4(R)-oxiranyl-[1,5]naphthyridine (1i) (1 equiv.) and LiClO₄ (1 equiv.) in DMF is added 6-[((3R,4S)-3-(trifluoromethyl)piperidin-4-ylamino)methyl]-4H-benzo[1,4]thiazin-3-one (2f) (1 equiv.). The reaction solution is heated to 70° C. for 18 hrs and then cooled to RT and concentrated under vacuum. Purification by chromatography on silica affords the title compound.

Example 3

6-({1-[(R)-2-Hydroxy-2-(6-methoxy-[1,5]naphthyridin-4-yl)ethyl]-4-(trifluoromethyl)piperidin-4-ylamino}methyl)-4H-benzo[1,4]thiazin-3-one

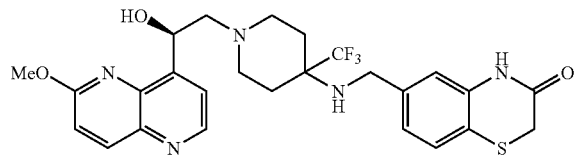

(a) Ethyl 1-(tert-butoxycarbonyl)piperidine-4-carboxylate

Di-tert-butyl dicarbonate (1.1 equiv.) is added to a solution of ethyl isonipecotate (1 equiv.) in CH₂Cl₂ at room temperature. When the reaction is complete, the solvent is removed in vacuo and the residue is purified by flash chromatography on silica gel to afford the title compound.

(b) Ethyl 1-(tert-butoxycarbonyl)-4-(trifluoromethyl)piperidine-4-carboxylate A solution of ethyl 1-(tert-butoxycarbonyl)piperidine-4-carboxylate (3a) (1 equiv.) in dry THF is added dropwise to a solution of LDA (1.5 equiv., prepared in standard fashion from diisopropylamine and n-BuLi) in dry THF at −78° C. The solution is stirred for 15 min, then a solution of S-(trifluoromethyl)dibenzothiophenium trifluoromethanesulfonate (1.1 equiv.) in dry THF is added. The reaction is allowed to warm to room temperature and is stirred until complete, then is quenched with saturated NH4Cl solution. The mixture is extracted with EtOAc, and the combined organic extracts are dried (MgSO₄) and concentrated in vacuo. The residue is purified by flash chromatography on silica gel to afford the title compound.

(c) 1-(tert-Butoxycarbonyl)-4-(trifluoromethyl)piperidine-4-carboxylic acid A solution of ethyl 1-(tert-butoxycarbonyl)-4-(trifluoromethyl)piperidine-4-carboxylate (3b) (1 equiv.) and 1.0 N NaOH (1.2 equiv.) in EtOH is heated at 50° C. When the reaction is complete, the solvents are removed in vacuo, and the residue is taken up in H₂O. The solution is acidified to pH 5-6 with dilute HCl, and the precipitate is collected and washed with H₂O. Drying in high vacuum gives the title compound.

(d) 4-(Benzyloxycarbonyl)amino-1-(tert-butoxycarbonyl)-4-(trifluoromethyl)piperidine Diphenylphosphoryl azide (1.1 equiv.) is added to a solution of 1-(tert-butoxycarbonyl)-4-(trifluoromethyl)piperidine-4-carboxylic acid (3c) (1 equiv.) and Et₃N (1 equiv.) in dry toluene at room temperature, and the reaction is warmed gradually to 80° C. The reaction is kept at 80° C. until gas evolution stops, then dry benzyl alcohol (2 equiv.) is added. The reaction is stirred at 80° C. until the isocyanate is consumed, then the solvents are removed in vacuo. The residue is taken up in CH₂Cl₂ and the solution is washed sequentially with dilute HCl, dilute NaOH, and H₂O. The solution is dried (MgSO₄) and concentrated in vacuo, and the residue is purified by flash chromatography on silica gel to afford the title compound.

(e) 4-Amino-1-(tert-butoxycarbonyl)-4-(trifluoromethyl)piperidine

10% Palladium on carbon (a catalytic amount) is added carefully to a solution of 4-(benzyloxycarbonyl)amino-1-(tert-butoxycarbonyl)-4-(trifluoromethyl)piperidine (3d) (1 equiv.) in EtOH, and the mixture is shaken under H₂ (50 psi) on a Parr apparatus. When the reaction is complete, the solution is filtered through a pad of celite®, and the filter pad is washed with EtOH. The filtrate is concentrated to yield the title compound.

(f) 6-[{1-(tert-Butoxycarbonyl)-4-(trifluoromethyl)piperidin-4-ylamino}methyl]-4H-benzo[1,4]thiazin-3-one A mixture of 4-amino-1-(tert-butoxycarbonyl)-4-(trifluoromethyl)piperidine (3 e) (1 equiv.), 3-oxo-3,4-dihydro-2H-benzo[1,4]thiazine-6-carbaldehyde (1n) (1.1 equiv.), and Na₂SO₄ in DMF is stirred until the imine has formed, then is filtered through a sintered glass funnel. The filtrate is concentrated to dryness in vacuo, and the residue is dissolved in EtOH. NaBH₄ (1 equiv.) is added, and the reaction is stirred until the imine is consumed. The solvent is removed in vacuo and the residue is taken up in dilute HCl. The mixture is neutralized with dilute NaOH and extracted with CH₂Cl₂. Drying (Na₂SO₄), concentration, and flash chromatography on silica gel gives the title compound.

(g) 6-[{4-(Trifluoromethyl)piperidin-4-ylamino}methyl]-4H-benzo[1,4]thiazin-3-one A solution of 6-[{1-(tert-butoxycarbonyl)-4-(trifluoromethyl)piperidin-4-ylamino}methyl]-4H-benzo[1,4]thiazin-3-one (3f) in 1:1 TFA/CH₂Cl₂ is stirred at room temperature until the starting material is consumed, then is concentrated to dryness in vacuo. The residue is partitioned between dilute NaOH and CH₂Cl₂, and the layers are separated. The aqueous layer is extracted with CH₂Cl₂, and the combined organic extracts are dried (Na₂SO₄) and concentrated in vacuo to afford the title compound.

(h) 6-({1-[(R)-2-Hydroxy-2-(6-methoxy-[1,5]naphthyridin-4-yl)ethyl]-4-(trifluoromethyl)piperidin-4-ylamino}methyl)-4H-benzo[1,4]thiazin-3-one A solution of 6-[{4-(trifluoromethyl)piperidin-4-ylamino}methyl]4H-benzo[1,4]thiazin-3-one (3g) (1 equiv.), 6-methoxy-4(R)-oxiranyl-[1,5]naphthyridine (1i) (1 equiv.), and LiClO₄ (1 equiv.) in DMF is heated at 100° C.

When the reaction is complete, the solution is cooled to room temperature and concentrated to dryness in vacuo. Flash chromatography on silica gel gives the title compound.

Example 4

6-({1-[(R)-2-Hydroxy-2-(6-methoxyquinolin-4-yl)ethyl]-2-oxopiperidin-4 ylamino}methyl)-4H-benzo[1,4]thiazin-3-one

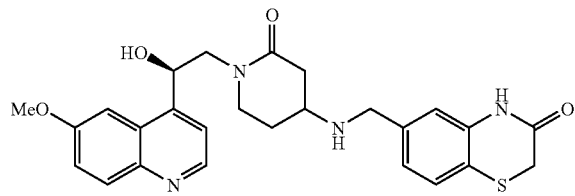

(a) (R,S)-4-Dibenzyl Amino-piperidin-2-one (Homo-Freidinger Lactam)

(R,S)-4-benzylamino)piperidin-2-one (Homo-Freidinger Lactam) was prepared from (R,S)-aspartic acid according to the procedure of Weber and Gmeiner, *Synlett,* 1998, 885-887. MS (ES) m/e 295 (M+H)+.

(b) 6-Methoxyquinoline-4-carboxylic acid

The title compound was prepared by modification of the procedure described by W. E. Doering and J. D. Chanley, *J. Amer. Chem. Soc.,* 1946, 68, 586. A mixture of quinone (derived from quinine by reaction with potassium tert-butoxide and benzophenone in toluene) (225 g, 0.70 mol), tert-butanol (1 litre) and water (10 ml) was treated with potassium tert-butoxide (170 g, 1.5 mol). The mixture was stirred at 30° C., while air was bubbled through for 3 days. The mixture was diluted with diethyl ether and water and the layers separated. The aqueous phase was extracted with ethyl acetate. The combined diethyl ether and ethyl acetate extracts were dried over magnesium sulfate and evaporated to give recovered starting material (approximately 100 g). The aqueous phase was acidified to pH5 with 5M hydrochloric acid. The precipitate was collected by filtration, washed with water and methanol, then dried to give 6-methoxyquinoline-4-carboxylic acid as a yellow solid (64.6 g, 46%).

δH (d-6 DMSO) 6.23-5.95 (1H, m), 5.34-5.06 (2H, m), 3.37-2.92 (5H, m), 2.70 (1H, m), 2.38-2.15 (3H, m), 1.94-1.52 (2H, m)

(c) [R]-2-(6-Methoxyquinolin-4-yl)oxirane

A solution of 6-methoxyquinoline-4-carboxylic acid (4b) (10 g) in dichloromethane was heated under reflux with oxalyl chloride (5 ml) and dimethylformamide (2 drops) for 1 hour and evaporated to dryness. The residue, in dichloromethane (100 ml) was treated with a 2M solution of trimethylsilyldiazomethane in hexane (50 ml) and stirred at room temperature for 18 hours. 5M Hydrochloric acid (150 ml) was added and the solution was stirred at room temperature for 3 hours. It was basified with sodium carbonate solution, extracted with ethyl acetate and chromatographed on silica gel eluting with ethyl acetate-hexane to give the chloromethyl ketone (4.2 g). A batch of the chloromethyl ketone (20 g) was reduced with (+)-B-chlorodiisopinocampheylborane (40 g) in dichloromethane (400 ml) at room temperature for 18 hours followed by treatment with diethanolamine (30 g) for 3 hours. The product was chromatographed on silica gel eluting with ethyl acetate-hexane to give the chloroalcohol (16.8 g), which was dissolved in tetrahydrofuran (100 m) and reacted with sodium hydroxide (2.6 g) in water (13 ml) for 1.5 hours. The reaction mixture was evaporated to dryness and chromatographed on silica gel eluting with ethyl acetate-hexane to give the title compound as a solid (10.4 g) (84% ee by chiral HPLC).

Recrystallisation from ether-pentane gave mother-liquor (7.0 g) (90% ee).

MS (+ve ion electrospray) m/z 202 (MH+)

The absolute stereochemistry was defined to be (R) by an NMR study on the Mosher's esters derived from the product obtained by reaction with 1-t-butylpiperazine.

(d) Dibenzylamino-[(R)-2-hydroxy-2-(6-methoxyquinolin-4-yl)ethyl]piperidin-2-one To a stirred solution of (R,S)-4-(dibenzylamino)piperidin-2-one (0.14 g, 0.47 mmole) in THF (5 mL) at 0° C. was added sodium hydride (60% dispersion in oil, 40 mg, 0.94 mmole). The resulting mixture was stirred at 0° C. for 30 min and then was allowed to warm to RT over 1 h. To this mixture was added 6-methoxy-4-(R)-oxiranylquinoline (4c) (0.17 g, 0.58 mmole) in THF (2 mL). The resulting mixture was stirred at RT for 24 h then was extracted with EtOAc. The organic layer was washed with sodium bicarbonate, H2O, and brine, then was dried over MgSO4. Concentration in vacuo followed by flash column chromatography on silica gel (50% EtOAc/hexanes) gave the title compound (50 mg, 30%) as a solid: MS (ES) m/e 496 (M+H)+.

(e) 4-Amino-1-[(R)-2-hydroxy-2-(6-methoxyquinolin-4-yl)ethyl]piperidin-2-one Dibenzylamino-[(R)-2-hydroxy-2-(6-methoxyquinolin-4-yl)ethyl]pipendin-2-one (4d) (1 equiv.) is dissolved in MeOH, treated with 10% Pd/C (a catalytic amount), and the mixture is shaken under H2 (50 psi) on a Parr apparatus. When the reaction is complete, the solution is filtered through a pad of celite®, and the filter pad is washed with MeOH. The filtrate is concentrated to yield the title compound.

(f) 6-({1-[(R)-2-hydroxy-2-(6-methoxyquinolin-4-yl)ethyl]-2-oxopiperidin-4-ylamino }-methyl)-4H-benzo[1,4]thiazin-3-one A mixture of 4-amino-1-[(R)-2-hydroxy-2-(6-methoxyquinolin-4-yl)ethyl]piperidin-2-one (4e) (1 equiv.), 3-oxo-3,4-dihydro-2H-benzo[1,4]thiazine-6-carbaldehyde (in) (1.1 equiv.), and Na2SO4 in DMF is stirred until the imine has formed, then is filtered through a sintered glass funnel. The filtrate is concentrated to dryness in vacuo, and the residue is dissolved in MeOH. NaBH4 (1 equiv.) is added, and the reaction is stirred until the imine is consumed. The solvent is removed in vacuo and the residue is taken up in dilute HCl. The mixture is neutralized with dilute NaOH and extracted with CH2Cl2. Drying (Na2SO4), concentration, and flash chromatography on silica gel gives the title compound.

Example 5

6-[({(3S,4R)-3-Fluoro-1-[(R)-2-hydroxy-2-(6-methoxyquinolin-4-yl)-ethyl]piperidin-4-ylamino}methyl)-4H-benzo[1,4]thiazin-3-one and 6-[({(3R,4S)-3-fluoro-1-[(R)-2-hydroxy-2-(6-methoxyquinolin-4-yl)-ethyl]piperidin-4-ylamino}methyl)-4H-benzo[1,4]thiazin-3-one Bis Trifluoroacetate

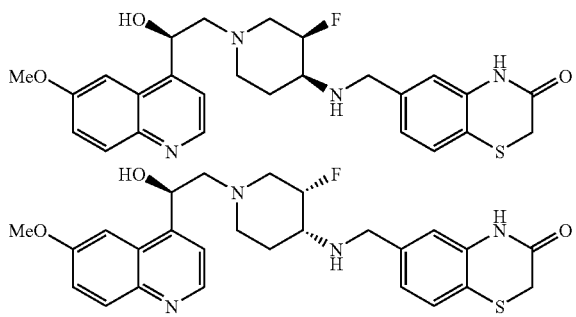

(a) (3R,4S) and (3S,4R)-4-Amino-1-tert-butoxycarbonyl-3-fluoropiperidine

To a solution of the enantiomeric mixture of cis-4-benzylamino-1-tert-butoxycarbonyl-3-fluoropiperidine (prepared according to the procedures of *J. Med. Chem.* 1999, 42, 2087-2104, 1.0 g, 3.2 mmole) in EtOH (40 mL) was added 3 N HCl (2.5 mL) and 10% Pd/C (50 mg). The reaction was shaken under $H_2$ (40 psi) on a Parr aparatus for 14 h, then was filtered through celites. The filtrate was concentrated under reduced pressure, and the residue was purified by flash chromatography on silica gel (10% MeOH/CHCl$_3$) to afford the title compound (370 mg, 53%) as a white solid: MS (ES) m/e 219 (M+H)$^+$.

(b) (3R,4S) and (3S,4R)-3-Fluoro-4-[(3-oxo-3,4-dihydro-2-H-pyrido[3,2-b][1,4]thiazin-6-ylmethyl)-amino]-piperidine A solution of cis-4-amino-1-tert-butoxycarbonyl-3-fluoropiperidine (5a) (220 mg, 1.00 mmole) in CH$_2$Cl$_2$ (5 mL) and EtOH (0.5 mL) was treated with anhydrous Na$_2$SO$_4$ (280 mg) and 3-oxo-3,4-dihydro-2-benzo[1,4]thiazine-6-carboxaldehyde (1n) (210 mg, 1.10 mmole). The resulting solution was stirred at room temperature for 14 hr, then sodium triacetoxy borohydride (320 mg, 1.50 mmole) was added. The resulting slurry was stirred at room temperature for a further 10 hr. then was quenched by the addition of water (2 mL) and the volatiles were removed in vacuo. The residue was partitioned between EtOAc (2×50 mL) and brine (20 mL). The organic phases were combined, dried (MgSO$_4$), and concentrated in vacuo. The residue was dissolved in CH$_2$Cl$_2$, passed through a plug of silica gel, and treated with a 2:1 mixture of CH$_2$Cl$_2$ and trifluoroacetic acid (30 mL). After 4 h the volatiles were removed in vacuo and the residue was purified by reversed-phase HPLC (30×75 mm ODS-A column; gradient elution: 10-90% CH$_3$CN/H$_2$O containing 0.1% TFA). Concentration under reduced pressure gave the desired compound as a white solid: MS (ES) m/e 296 (M+H)$^+$.

(c) 6-[({(3S,4R)-3-Fluoro-1-[(R)-2-hydroxy-2-(6-methoxyquinolin-4-yl)-ethyl]piperidin-4-ylamino}methyl)-4H-benzo[1,4]thiazin-3-one and 6-[({(3R,4S)-3-fluoro-1-[(R)-2-hydroxy-2-(6-methoxyquinolin-4-yl)-ethyl]piperidin-4-ylamino}methyl)-4H-benzo[1,4]thiazin-3-one To an enantiomeric mixture of 3-fluoro-4-[(3-oxo-3,4-dihydro-2-H-pyrido[3,2-b][1,4]thiazin-6-ylmethyl)amino] piperidine (5b) (100 mg, 0.33 mmole) in DMF (2 mL) was added LiClO$_4$ (38 mg, 0.33 mmole), K$_2$CO$_3$ (88 mg, 0.66 mmole), and 6-methoxy-4-(R)-oxiranylquinoline (4c) (70 mg, 0.33 mmole). The reaction was heated at 90° C. for 18 h, cooled to RT and concentrated under reduced pressure. The residue was partitioned between ethyl acetate and H$_2$O, and the layers were separated. The aqueous phase was further extracted with ethyl acetate, and the combined organic extracts were dried over MgSO$_4$ and concentrated under reduced pressure. The residue was purified by flash chromatography on silica gel followed by reversed-phase HPLC (30×75 mm ODS-A column; gradient elution: 10-90% CH$_3$CN/H$_2$O containing 0.1% TFA). Concentration under reduced pressure gave the desired compound as a white solid: (ES) m/e 497 (M+H)$^+$. $^1$H NMR AH (CD$_3$OD, 400 MHz), 2.44-2.59 (2H, m), 3.41-3.98 (7H, m), 3.89 (2H, m), 4.02 (3H, s), 4.33 (1H, s), 4.88 (1H, d), 5.42 (1H, dd), 6.29 (1H, d), 7.10 (1H, d), 7.31 (1H, d), 7.37 (1H, dd), 7.63 (2H, m), 8.05 (2H, d), 8.77 (1H, s), 8.85 (1H, d).

Example 6

6-({cis-3-Fluoro-1-[(R)-2-hydroxy-2-(6-methoxyquinolin-4-yl)-ethyl]piperidin-4-ylamino}methyl)-4H-pyrido[3,2-b][1,4]thiazin-3-one Diastereoisomer 1 Dihydrochloride

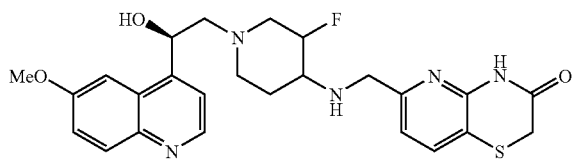

(a) cis-4-Benzylamino-1-tert-butoxycarbonyl-3-fluoropiperidine

4-Benzyl-1-tert-butoxycarbonyl-3-fluoropiperidine was prepared according to the procedures of *J. Med. Chem.* 1999, 42, 2087-2104 as a mixture of isomers (approx 8:1 cis:trans, 29.8 g, 0.096 mole). The mixture was dissolved in DCM, extracted with 0.2M HCl, basified with Na$_2$CO$_3$ solution, extracted with DCM and chromatographed on silica gel to give the cis-isomer in the later fractions (15.6 g, 52%). Combined batches (32 g, 0.103 mole) were separated by preparative BPLC on a Chiralpak AD column eluting with hexane:ethanol (9:1) to give faster running enantiomer [Enantiomer 1] (15.0 g, 47%, 99% ee) [α]$_D$+40.5° and slower running enantiomer [Enantiomer 2] (15.0 g, 47%, 97% ee) [α]$_D$−39.5°.

(b) 4-Benzyloxycarbonylamino-3-fluoropiperidine Enantiomer 1 cis-(+)-4-Benzylamino-1-tert-butoxycarbonyl-3-fluoropiperidine [Enantiomer 1] (15.0 g, 0.049 mole) in ethanol (300 ml) was hydrogenated over 20% palladium hydroxide on carbon (4 g) at 30 psi for 5 h, then filtered through celite and evaporated. The crude amine was dissolved in ethyl acetate (100 mL), saturated sodium hydrogen carbonate solution (100 mL) was added followed by benzyl chloroformate (7.6 mL, 0.53 mole) and the mixture stirred vigorously for 4 h. The organic phase was separated dried and evaporated. The product was dissolved in DCM (75 mL) and stirred with TFA (20 mL) for 4 h then evaporated. The residue was basified with sodium carbonate solution, extracted with 10% methanol in DCM and the extracts dried and evaporated to give a white solid (12.1 g, 98%), [α]$_D$+61.10 (MeOH).

(c) (R)-2-(4-Amino-3-fluoropiperidin-1-yl)-1-(6-methoxyquinolin-4-yl)-ethanol Diastereoisomer 1

4-Benzyloxycarbonylamino-3-fluoropiperidine Enantiomer 1 (2.4 g, 9.5 mmole) and 6-methoxy-4-(R)-oxiranylquinoline (1.9 g, 9.5 mmole) were heated together at 80° C. for 2 h, then allowed to cool, and the product was purified on silica gel. The material obtained was dissolved in ethanol (80 mL) and hydrogenated with 10% Pd/C (0.6 g) for 6 h, then filtered through Celite® and evaporated to give a yellow foam (1.9 g, 62%)

MS (ES) m/z 320 (M+H)$^+$.

(d) Methyl 3-oxo-3,4-dihydro-2H-pyrido[3,2-b][1,4]thiazine-6-carboxylate

A solution of ethyl 2-mercaptoacetate (1.473 mL) in DMF (48 mL) was ice-cooled and treated with sodium hydride (540 mg of a 60% dispersion in oil). After 1 hour methyl 6-amino-5-bromopyridine-2-carboxylate (3 g) (T. R. Kelly and F. Lang, *J. Org. Chem.* 61, 1996, 4623-4633) was added and the mixture stirred for 16 hours at room temperature. The solution was diluted with EtOAc (1 litre), washed with water (3×300 mL), dried and evaporated to about 10 mL. The white solid was filtered off and washed with a little EtOAc to give the ester (0.95 g).

MS (APCI$^-$) m/z 223 ([M−H]$^-$, 100%)

(e) 3-Oxo-3,4-dihydro-2H-pyrido[3,2-b][1,4]thiazine-6-carboxylic acid

A solution of ester (6d) (788 mg) in dioxan (120 ml)/water (30 mL) was treated dropwise over 2 hours with 0.5M NaOH solution (8 mL) and stirred overnight. After evaporation to approx. 3 ml, water (5 mL) was added and 2N HCl to pH4. The precipitated solid was filtered off, washed with a small volume of water and dried under vacuum to give a solid (636 mg).

MS (APCI$^-$) m/z 209 ([M−H]$^-$, 5%), 165([M-COOH]$^-$, 100%)

(f) 6-Hydroxymethyl-3-oxo-3,4-dihydro-2H-pyrido[3,2-b][1,4]thiazine

A solution of the carboxylic acid (6e) (500 mg) in THF (24 mL) with triethylamine (0.396 mL) was cooled to −10° C. and isobutyl chloroformate (0.339 ml) added. After 20 minutes the suspension was filtered through kieselguhr into an ice-cooled solution of sodium borohydride (272 mg) in water (8 mL), the mixture stirred 30 minutes and the pH reduced to 7 with dilute HCl. The solvent was evaporated and the residue triturated under water. The product was filtered and dried under vacuum to give a white solid (346 mg).

MS (APCI$^-$) m/z 195 ([M−H]$^-$, 50%), 165(100%)

(g) 3-Oxo-3,4-dihydro-2H-pyrido[3,2-b][1,4]thiazine-6-carboxaldehyde

A solution of the alcohol (6f) (330 mg) in dichloromethane (30 mL)/THF (30 mL) was treated with manganese dioxide (730 mg) and stirred at room temperature. Further manganese dioxide was added after 1 hour (730 mg) and 16 hours (300 mg). After a total of 20 hours the mixture was filtered through kieselguhr and the filtrate evaporated. The product was triturated with EtOAc/hexane (1:1) and collected to give a solid (180 mg).

MS (APCI$^-$) m/z 195 ([M−H]$^-$, 95%), 165 (100%)

(h) Title Compound (R)-2-(4-Amino-3-fluoropiperidin-1-yl)-1-(6-methoxyquinolin-4-yl)-ethanol Diastereoisomer 1 (0.45 g, 1.41 mmole) and aldehyde (6g) (0.275 g, 1.41 mmol) in DMF (12 mL), ethanol (12 mL), and acetic acid (1.2 mL) were stirred with 4A sieves at 80° C. for 2 h, then allowed to cool. Sodium cyanoborohydride (0.215 g, 3.4 mmole) was added and the mixture stirred at room temperature for 3 days, then evaporated to dryness. The residue was basified with sodium carbonate solution and extracted with 20% methanol in DCM. The extracts were concentrated and chromatographed on silica gel to give the title compound (0.44 g, 62%) as the free base.

MS (ES) m/z 498 (M+H)$^+$. $^1$H NMR δH (CDCl$_3$, 400 MHz), 1.65-1.96 (5H, m), 2.41-2.95 (6H, m), 3.43-3.54 (1H, m), 3.91 (2H, s), 3.93 (3H, s), 4.25 (1H, s), 4.88 (1H, d), 5.41 (1H, dd), 7.04 (1H, d), 7.17 (1H, d), 7.37 (1H, dd), 7.58 (1H, d), 7.63 (1H, d), 8.05 (1H, d), 8.68 (1H, s), 8.77 (1H, d).

This material, as a solution in chloroform/methanol, was treated with an excess of 4M HCl in dioxan and evaporated to dryness. The solid was triturated under ether, filtered and dried under vacuum to provide the title compound.

Example 7

6-({cis-3-Fluoro-1-[(R)-2-hydroxy-2-(6-methoxyquinolin-4-yl)-ethyl]-piperidin-4-ylamino}-methyl)-4H-pyrido [3,2-b][1,4]thiazin-3-one Diastereoisomer 2 Dihydrochloride

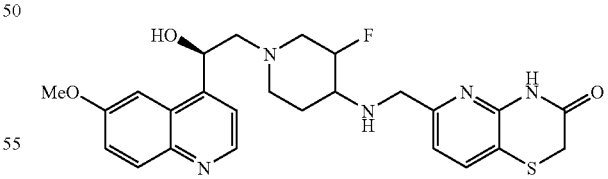

(a) cis-4-Benzyloxycarbonylamino-3-fluoropiperidine Enantiomer 2

This was prepared from cis-(−)-4-benzylamino-1-tert-butoxycarbonyl-3-fluoropiperidine [(6a; Enantiomer 2] by the method of Example (6b) to give a foam, [α]$_D$−62.50 (MeOH).

(b) (R)-2-(4-Amino-3-fluoropiperidin-1-yl)-1-(6-methoxyquinolin-4-yl)-ethanol Diastereoisomer 2

This was prepared from amine (7a) and 6-methoxy-4-(R)-oxiranylquinoline followed by hydrogenation over 10% Pd/C as described in Example (6c) to give the product as a foam (62%).
MS (ES) m/z 320 (M+H)+.

(c) Title Compound

This was prepared from (R)-2-(4-amino-3-fluoropiperidin-1-yl)-1-(6-methoxyquinolin-4-yl)-ethanol Diastereoisomer 2 (0.45 g, 1.41 mmole) by the method of Example (6h) to give the title compound as the free base (0.54 g, 77%).
MS (ES) m/z 498 (M+H)+. $^1$H NMR δH (CDCl$_3$, 400 MHz), 1.57-1.98 (4H, m), 2.26-2.81 (5H, m), 2.95 (1H, dd), 3.17-3.28 (2H, m), 3.85-4.00 (5H, m), 4.22 (1H, s), 4.84 (1H, d), 5.45 (1H, dd), 7.04 (1H, d), 7.17 (1H, d), 7.37 (1H, dd), 7.59 (1H, d), 7.63 (1H, d), 8.05 (1H, d), 8.46 (1H, s), 8.78 (1H, d).

This material, as a solution in chloroform/methanol, was treated with an excess of 4M HCl in dioxan and evaporated to dryness. The solid was triturated under ether, filtered and dried under vacuum to provide the title compound.

Example 8

7-Chloro-6-({cis 3-fluoro-1-[(R)-2-hydroxy-2-(6-methoxyquinolin-4-yl)-ethyl]piperidin-4-ylamino}methyl)-4H-pyrido[3,2-b][1,4]thiazin-3-one Diastereoisomer 1 Dihydrochloride

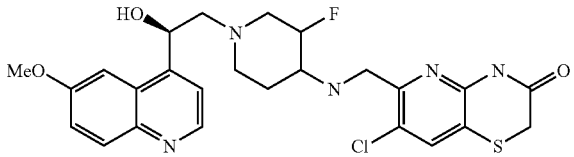

(a) Methyl 6-amino-5-bromo-3-chloropyridine-2-carboxylate

To a solution of methyl 6-amino-5-bromopyridine-2-carboxylate (20.04 g) in acetic acid (900 mL) was added N-chlorosuccinimide (13.96 g) and the resultant solution was heated to 120° C. for 1 hour. The solution was then evaporated and treated with excess aqueous sodium bicarbonate and extracted with dichloromethane. The organic fraction was dried and evaporated to give the product (21.98 g).
MS (+ve ion electrospray) m/z 265 and 267 (MH+, 100%)

(b) Methyl 7-chloro-3-oxo-3,4-dihydro-2H-pyrido[3,2-b][1,4]thiazine-6-carboxylate This was prepared (51%) from the ester (8a) (23.8 g) by the method of Example (6d) to give a solid (11.8 g).
MS (+ve ion electrospray) m/z 257 (MH+, 100%)

(c) 7-Chloro-3-oxo-3,4-dihydro-2H-pyrido[3,2-b][1,4]thiazine-6-carboxylic acid

This compound was prepared (96%) from the ester (8b) (11.84 g) by the method of Example (6e) to give a solid (9.6 g).

MS (APCI−) m/z 243 ([M−H]−, 2%), 199 ([M-COOH], 100%)

(d) 7-Chloro-6-hydroxymethyl-3-oxo-3,4-dihydro-2H-pyrido[3,2-b][1,4]thiazine

This compound was prepared (70%) from the carboxylic acid (8c) by the method of Example (6f).
MS (+ve ion electrospray) m/z 231 (MH+, 100%)

(e) 7-Chloro-3-oxo-3,4-dihydro-2H-pyrido[3,2-b][1,4]thiazine-6-carboxaldehyde

This compound was prepared (49%) from the alcohol (8d) by the method of Example (6g) to give a solid (2.01 g).
MS (+ve ion electrospray) m/z 229 (NM+, 100%)

(f) Title Compound

The free base of the title compound was prepared from R)-2-(4-amino-3-fluoropiperidin-1-yl)-1-(6-methoxyquinolin-4-yl)-ethanol Diastereoisomer 1 (6c) and aldehyde (8e) by the method of Example (6h) (71%).
MS (ES) m/z 532 (MH)+. $^1$H NMR δH (CDCl$_3$, 400 MHz), 1.86-2.02 (3H, m), 2.42-2.65 (4H, m), 2.74-2.95 (3H, m), 3.44-3.55 (1H, m), 3.93 (3H, s), 4.03 (2H, q), 4.23 (1H, s), 4.90 (1H, d), 5.42 (1H, dd), 7.17 (1H, d), 7.60 (1H, s), 7.64 (1H, dd), 7.59 (1H, d), 8.05 (1H, d), 8.66 (1H, s), 8.77 (1H, d).

This material, as a solution in chloroform/methanol, was treated with an excess of 4M HCl in dioxan and evaporated to dryness. The solid was triturated under ether, filtered and dried under vacuum to provide the title compound.

Example 9

7-Chloro-6-({cis-3-Fluoro-1-[(R)-2-hydroxy-2-(6-methoxyquinolin-4-yl)-ethyl]piperidin-4-ylamino}methyl)-4H-pyrido[3,2-b][1,4]thiazin-3-one Diastereoisomer 2 Dihydrochloride

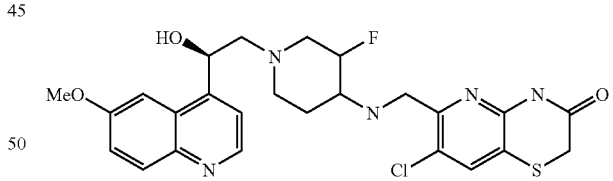

The free base of the title compound was prepared from (R)-2-(4-amino-3-fluoropiperidin-1-yl)-1-(6-methoxyquinolin-4-yl)-ethanol Diastereoisomer 2 (7b) and aldehyde (8e) by the method of Example (6h) (59%).
MS (ES) n/e 532 (M+H)+. $^1$H NMR δH (CDCl$_3$, 400 MHz), 1.90-2.01 (3H, m), 2.29-2.40 (1H, m), 2.44-3.04 (5H, m), 3.17-3.30 (2H, m), 3.92 (3H, s), 4.03 (2H, s), 4.29 (1H, s), 4.86 (1H, dd), 5.46 (1H, dd), 7.17 (1H, d), 7.37 (1H, dd), 7.59 (1H, s), 7.65 (1H, d), 8.05 (1H, d), 8.77 (1H, d), 8.91 (1H, s).

This material, as a solution in chloroform/methanol, was treated with an excess of 4M HCl in dioxan and evaporated to dryness. The solid was triturated under ether, filtered and dried under vacuum to provide the title compound.

Example 10

6-({cis-3-Fluoro-1-[(R)-2-hydroxy-2-(6-methoxyquinolin-4-yl)-ethyl]piperidin-4-ylamino}methyl)-4H-pyrido[3,2-b][1,4]oxazin-3-one Diastereoisomer 1 Dihydrochloride

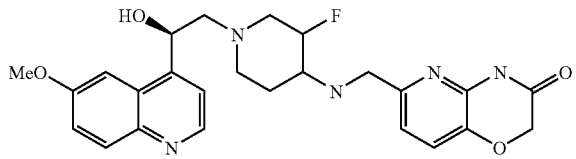

(a) 2-Bromo-5-hydroxy-6-nitropyridine

3-Hydroxy-2-nitropyridine (20 g, 0.143 mole) was dissolved in methanol (400 mL) and a solution of 25% sodium methoxide in methanol (33 mL, 0.13 mole) was added at room temperature. The mixture was stirred for 30 min, then was cooled to 0° C., and bromine (7.2 mL, 0.14 mole) was added slowly. The reaction was stirred at 0° C. for 30 min, then was quenched with glacial AcOH (2.5 ml). The solvent was removed in vacuo to afford material (30 g, 96%), which was used without further purification.

MS (ES) m/z 219.0 (M+H)$^+$.

(b) Ethyl (6-bromo-2-nitro-pyridin-3-yloxy)acetate

The hydroxypyridine (10a) (30 g, 0.14 mole) was suspended in acetone (200 ml), and potassium carbonate (39 g, 0.28 mole) was added, followed by ethyl bromoacetate (15.7 ml, 0.14 mmole). The reaction was heated at reflux for 10 hr, then was cooled to room temperature and diluted with Et$_2$O. The precipitate was removed by suction filtration, and the filtrate was concentrated in vacuo to afford material (38 g, 89%), which was used without further purification.

MS (ES) m/z 305.0 (M+H)$^+$.

(c) 6-Bromo-4H-pyrido[3,2-b](1,4]oxazin-3-one

The nitropyridine (10b) (38 g, 0.125 mole) was dissolved in glacial AcOH (150 mL), and iron powder (20 g, 0.36 mole) was added. The mixture was mechanically stirred and heated at 90° C. for 5 hr, then was cooled to room temperature and diluted with EtOAc (300 mL). The mixture was filtered through a pad of silica gel and the filtrate was concentrated in vacuo and the residue recrystallized from MeOH (15 g, 52%).

MS (ES) m/z 229.0 (M+H)$^+$.

(d) 6-((E)-Styryl)-4H-pyrido [3,2-b][1,4]oxazin-3-one

The bromopynidine (10c) (6.0 g, 26.3 mmole) and trans-2-phenylvinylboronic acid (3.9 g, 26.3 mmole) were dissolved in 1,4-dioxane (150 mL) and the solution was degassed with argon. (Ph$_3$P)$_4$Pd (230 mg, 0.2 mmole) was added, followed by a solution of potassium carbonate (6.9 g, 50 mmole) in H$_2$O (20 mL). The reaction was heated at reflux under argon overnight, then was cooled to room temperature and diluted with EtOAc (200 mL). The solution was washed sequentially with H$_2$O and brine, dried (Na$_2$SO$_4$), and concentrated in vacuo. The solid residue was purified by flash chromatography on silica gel (5-10% EtOAc/CHCl$_3$) to afford a solid (2.5 g, 38%).

MS ES) m/z 253.0 M+H)$^+$.

(e) 3-Oxo-3,4-dihydro-2H-pyrido[3,2-b][1,4]oxazine-6-carboxaldehyde

The pyridine (10d) (1.2 g, 4.8 mmole) was dissolved in CH$_2$Cl$_2$ (200 mL) and the solution was cooled to −78° C. Ozone was bubbled through the solution with stirring until a pale blue color appeared, then the excess ozone was removed by bubbling oxygen through the solution for 15 min. Dimethylsulfide (1.76 mL, 24 mmole) was added to the solution, and the reaction was stirred at −78° C. for 3 hr, then at room temperature overnight. The solvent was removed in vacuo, and the residue was triturated with Et$_2$O (50 mL). The collected solid was washed with additional Et$_2$O and dried to afford a solid (700 mg, 82%).

MS (ES) m/z 179.0 (M+H)$^+$.

(f) Title Compound

The free base of the title compound was prepared from (R)-2-(4-amino-3-fluoropiperidin-1-yl)-1-(6-methoxyquinolin-4-yl)-ethanol Diastereoisomer 1 (6c) and aldehyde (10e) by the method of Example (6h) (75%).

MS (ES) m/z 482 (M+H)$^+$. $^1$H NMR δH (CDCl$_3$, 400 MHz), 1.84-1.99 (4H, m), 2.41-2.98 (6H, m), 3.45-3.56 (1H, m), 3.89 (2H, q), 3.92 (3H, s), 4.23 (1H, s), 4.88 (1H, d), 5.42 (1H, dd), 6.99 (1H, d), 7.18 (1H, d), 7.21 (1H, d), 7.37 (1H, dd), 7.63 (1H, dd), 8.05 (1H, d), 8.77 (1H, s), 8.85 (1H, d).

This material, as a solution in chloroform/methanol, was treated with an excess of 4M HCl in dioxan and evaporated to dryness. The solid was triturated under ether, filtered and dried under vacuum to provide the title compound.

Example 11

6-({cis-3-Fluoro-1-[(R)-2-hydroxy-2-(6-methoxyquinolin-4-yl)-ethyl]piperidin-4-ylamino}methyl)-4H-pyrido[3,2-b][1,4]oxazin-3-one Diastereoisomer 2 Dihydrochloride

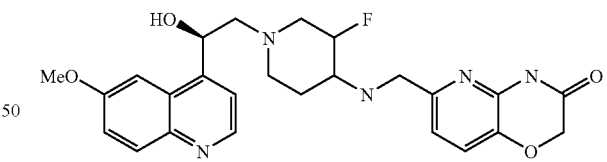

The free base of the title compound was prepared from (R)-2-(4-amino-3-fluoropiperidin-1-yl)-1-(6-methoxyquinolin-4-yl)-ethanol Diastereoisomer 2 (7b) and aldehyde (10e) by the method of Example (6h) (52%).

MS (ES) m/e 532 (M+H)$^+$. $^1$H NMR δH (CDCl$_3$, 400 MHz), 1.80-2.18 (5H, m), 2.61-2.97 (6H, m), 3.15-3.28 (2H, m), 3.91 (3H, s), 3.92 (2H, q), 4.36 (1H, s), 4.84 (1H, d), 5.45 (1H, dd), 6.98 (1H, d), 7.16 (1H, d), 7.20 (1H, d), 7.36 (1H, dd), 7.65 (1H, dd), 8.06 (1H, d), 8.78 (1H, d), 9.30-10.00 (1H, s).

This material, as a solution in chloroform/methanol, was treated with an excess of 4M HCl in dioxan and evaporated to dryness. The solid was triturated under ether, filtered and dried under vacuum to provide the title compound.

Example 12

7-Chloro-6-[({(3S,4R)-3-fluoro-1-[(R)-2-hydroxy-2-(6-methoxyquinolin-4-yl)-ethyl]piperidin-4-ylamino}methyl)-4H-pyrido[3,2-b][1,4]thiazin-3-one and 7-chloro-6-[({(3R,4S)-3-fluoro-1-[(R)-2-hydroxy-2-(6-methoxyquinolin-4-yl)-ethyl]piperidin-4-ylamino}methyl)-4H-pyrido[3,2-b][1,4]thiazin-3-one Dihydrochloride

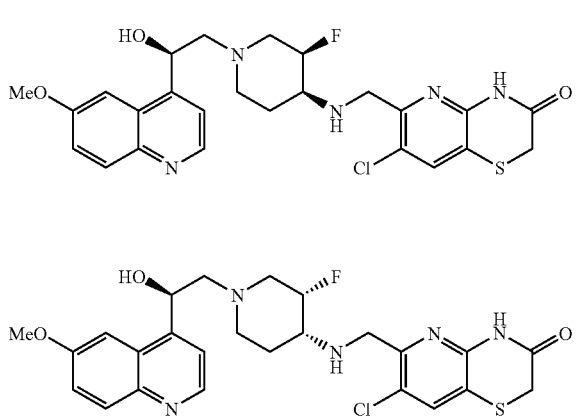

(a) (3R,4S) and (3S,4R)-4-Benzyloxycarbonylamino-3-fluoropiperidine

A mixture of enantiomers of cis-4-benzylamino-1-tert-butoxycarbonyl-3-fluoropiperidine, prepared as described in Example (6a) was reacted by the method of Example 6(b) to give an off white solid (86%).

(b) (R)-2-(3R,4S)-(4-Amino-3-fluoropiperidin-1-yl)-1-(6-methoxyquinolin-4-yl)-ethanol and (R)-2-(3S,4R)-(4-Amino-3-fluoropiperidin-1-yl)-1-(6-methoxyquinolin-4-yl)-ethanol (3R,4S) and (3S,4R)-4-Benzyloxycarbonylamino-3-fluoropiperidine was reacted as described in Example (6c) to give a pale yellow foam (64%).

(c) Title Compounds

The free base of the title compounds were prepared as a 1:1 mixture from amines (12b) and aldehyde (8e) by the method of Example (6h) (67%).

MS (ES) m/z 516 (M+H)$^+$. $^1$H NMR δH (CDCl$_3$, 400 MHz), 1.82-2.01 (2H, m), 2.17-3.01 (8.5H, m), 3.18-3.31 (1H, m), 3.43-3.57 (0.5H, m), 3.93 (3H, s), 4.02 (2H, q), 4.87, 4.91 (1H, 2d), 5.43 (1H, m), 7.18 (1H, d), 7.21 (1H, m), 7.37 (1H, dd), 7.60 (1H, s), 7.64 (1H, dd), 8.05 (1H, d), 8.72 (1H, s), 8.78 (1H, d).

This material, as a solution in chloroform/methanol, was treated with an excess of 4M HCl in dioxan and evaporated to dryness. The solid was triturated under ether, filtered and dried under vacuum to provide the title compound.

Example 13

7-Fluoro-6-({(3S,4R)-3-fluoro-1-[(R)-2-hydroxy-2-(6-methoxyquinolin-4-yl)-ethyl]piperidin-4-ylamino}methyl)-4H-pyrido[3,2-b][1,4]thiazin-3-one and 7-fluoro-6-[({(3R,4S)-3-fluoro-1-[(R)-2-hydroxy-2-(6-methoxyquinolin-4-yl)-ethyl]piperidin-4-ylamino}methyl)-4H-pyrido[3,2-b][1,4]thiazin-3-one Dihydrochloride

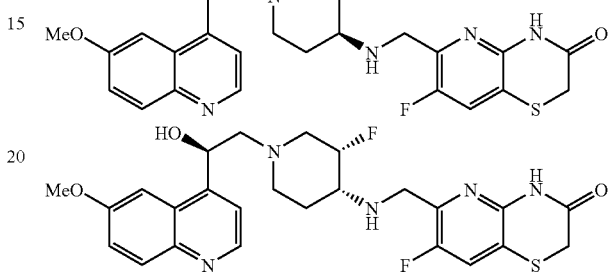

(a) Methyl 6-amino-5-bromo-3-fluoropyridine-2-carboxylate

A mixture of methyl 6-amino-5-bromopyridine-2-carboxylate (19.8 g) (T. R. Kelly and F. Lang, *J. Org. Chem.* 61, 1996, 4623-4633) and 1-chloromethyl-4-fluoro-1,4-diazoniabicyclo[2.2.2]octane bis(tetrafluoroborate) (34.3 g) in acetonitrile (340 mL) under argon was heated to 40° C. for 1 hour, 60° C. for 1 hour and then 80° C. overnight. After partitioning between EtOAc and water (500 mL each) the aqueous fraction was re-extracted with EtOAc (300 mL) and the combined organic solution dried with MgSO$_4$ and evaporated. Chromatography (20% then 30% EtOAc in hexane) separated various byproducts from the required ester (2.09 g).

MS (+ve ion electrospray) m/z 249 and 251 (MH$^+$, 100%)

(b) Methyl 6-amino-5-ethoxycarbonylmethylthio-3-fluoropyridine-2-carboxylate A solution of ethyl mercaptoacetate (1.15 mL) in DMP (40 mL) was ice-cooled under argon, treated with sodium hydride (420 mg of a 60% dispersion in oil) and stirred until all was in solution (about 1 hour). The ester (308a) (2.48 g) was added, the mixture allowed to warm to room temp. and stirred overnight. EtOAc (150 mL) was added, the solution washed with water (3×150 mL), dried and evaporated. Chromatography of the residue (30 then 40% EtOAc in hexane) gave the product as an oil (1.7 g).

MS (+ve ion electrospray) m/z 289 (, 100%)

(c) Methyl 7-fluoro-3-oxo-3,4-dihydro-2H-pyrido[3,2-b][1,4]thiazine-6-carboxylate A solution of the fluoropyridine (13b) (1.7 g) in acetic acid (100 mL) was heated at 110° C. overnight, evaporated and dried under vacuum to give the product as a white solid (1.55 g, containing 0.33 equivalent of acetic acid).

MS (+ve ion electrospray) m/z 243 W, 85%), 211 (100%)

(d) 7-Fluoro-3-oxo-3,4-dihydro-2H-pyrido[3,2-b][1,4]thiazine-6-carboxylic Acid This compound was prepared from the ester (13c) by the method of Example (6e) (86%).

(e) 7-Fluoro-6-hydroxymethyl-3-oxo-3,4-dihydro-2H-pyrido[3,2-b][1,4]thiazine This compound was prepared from carboxylic acid (13d) by the method of Example (6f) (73%).
MS (−ve ion electrospray) m/z 213 ([M−H]⁻, 100%)

(f) 7-Fluoro-3-oxo-3,4-dihydro-2H-pyrido[3,2-b][1,4]thiazine-6-carboxaldehyde A mixture of the 7-fluoro-pyridothiazinone (13e) (971 mg), manganese dioxide (3.72 g), THF (70 mL) and 1,2-dichloroethane (70 mL) was heated at 60° C. under argon for 20 hours. Filtration through kieselguhr and evaporation of solvent gave a solid which was triturated under EtOAc/hexane 1:3 and collected (608 mg).
MS (+ve ion electrospray) m/z 213 (MH⁺, 100%)

(g) Title Compounds

The free base of the title compounds were prepared as a 1:1 mixture from amines (12b) and aldehyde (13f) by the method of Example (6h)(71%).
MS (ES) m/z 515 (M+H)⁺. ¹H NMR δH (CDCl₃, 400 MHz), 1.67-2.04 (3H, m), 2.30-2.98 (6.5H, m), 3.16-3.28 (1H, m), 3.39 (s covering m, 0.5H), 3.92 (3H, 2s), 3.95 (2H, q), 4.23 (1H, s), 4.84, 4.87 (1H, 2d), 5.43 (1H, m), 7.17 (1H, m), 7.37 (2H, m), 7.64 (1H, dd), 8.05 (1H, dd), 8.67 (1H, d), 8.77 (1H, d).

This material, as a solution in chloroform/methanol, was treated with an excess of 4M HCl in dioxan and evaporated to dryness. The solid was triturated under ether, filtered and dried under vacuum to provide the title compound.

Example 14

7-({(3S,4R)-3-fluoro-1-[(R)-2-hydroxy-2-(6-methoxyquinolin-4-yl)-ethyl]piperidin-4-ylamino}methyl)-1H-pyrido[2,3-b][1,4]thiazin-2-one and 7-({(3R,4S)-3-fluoro-1-[(R)-2-hydroxy-2-(6-methoxyquinolin-4-yl)-ethyl]piperidin-4-ylamino}methyl)-1H-pyrido[2,3-b][1,4]thiazin-2-one Dihydrochloride

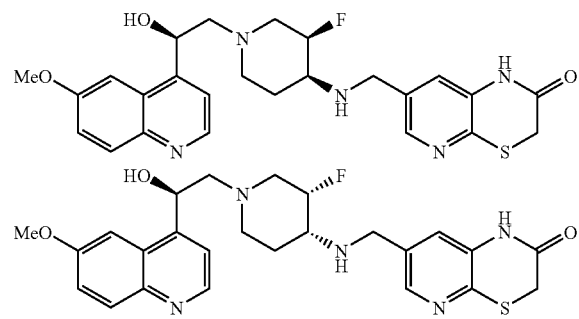

(a) 6-Methoxycarbonylmethylsulfanyl-5-nitro-nicotinic Acid Methyl Ester

A solution of 6-chloro-5-nitro-nicotinic acid methyl ester (1.0 g) [prepared as described by A. H. Berrie et al. *J. Chem. Soc.* 2590-2594 (1951)] in dichloromethane (10 mL) containing triethylamine (0.76 mL) was treated with mercaptoacetic acid methyl ester (0.44 mL) and the solution was stirred at room temperature for 1 hour and evaporated to dryness. Sodium bicarbonate solution was added and the mixture was extracted with dichloromethane, dried (anhydrous sodium sulfate) and evaporated to afford a solid (1.0 g).
MS (+ve ion electrospray) m/z 287 (MH⁺).

(b) 2-Oxo-2,3-dihydro-1H-pyrido[2,3-b][1,4]thiazine-7-carboxylic Acid Methyl Ester The ester (13a) (1.0 g) in acetic acid (50 mL) was treated with iron powder (10 g) and the mixture was stirred and heated at 60° C. for 1 hour, cooled and filtered. The filtrate was evaporated, treated with sodium bicarbonate solution and extracted with warm chloroform. It was dried (anhydrous sodium sulfate) and evaporated to give a white solid (0.85 g).
MS (+ve ion electrospray) m/z 225 (MH+).

(c) 2-Oxo-2,3-dihydro-1H-pyrido[2,3-b][1,4]thiazine-7-carboxylic acid

The ester (13b) (2.8 g) was hydrolysed with aqueous sodium hydroxide in tetrahydrofin=by the method of Example (6e) to afford a solid (2.5 g).
MS (−ve ion electrospray) m/z 209 (M−H⁻).

(d) 7-Hydroxymethyl-1H-pyrido[2,3-b][1,4]thiazin-2-one

The carboxylic acid (13c) (2.48 g) was reacted with isobutylchloroformate and sodium borohydride by the method of Example (6f) to afford a solid (1.3 g), after recrystallisation from chloroform-methanol (9:1).
MS (+ve ion electrospray) m/z 197 (MH+).

(e) 2-Oxo-2,3-dihydro-1H-pyrido[2,3-b][1,4]thiazine-7-carboxaldehyde

The alcohol (13d) (1.22 g) was oxidised with manganese dioxide by the method of Example (6g) to afford a solid (0.7 g).
MS (−ve ion electrospray) m/z 193 (M−H⁻).

(f) Title Compound

The free base of the title compounds were prepared as a 1:1 mixture from amines (12b) and aldehyde (14e) by the method of Example (6h) (58%).
MS (ES) m/z 498 (M+H)⁺. ¹H NMR δH (CDCl₃, 400 MHz), 1.76-1.95 (3H, m), 2.26-2.99 (6.5H, m), 3.15-3.28 (1H, m), 3.46-3.55 (0.5H, m), 3.85 (2H, s), 3.92 (3H, s), 4.80, 4.84 (1H, 2d), 5.42 (1H, dd), 7.17 (1H, dd), 7.22 (1H, s), 7.37 (1H, dd), 7.63 (1H, dd), 8.05 (1H, d), 8.16 (1H, d), 8.77 (1H, d), 9.02 (1H, d).

This material, as a solution in chloroform/methanol, was treated with an excess of 4M HCl in dioxan and evaporated to dryness. The solid was triturated under ether, filtered and dried under vacuum to provide the title compound.

Example 15

7-Chloro-6-[({(3S,4R)-3-fluoro-1-[(R)-2-hydroxy-2-(6-methoxyquinolin-4-yl)-ethyl]piperidin-4-ylamino}methyl)-4H-pyrido[3,2-b][1,4]oxazin-3-one and 7chloro-6-[({(3R,4S)-3-fluoro-1-[(R)-2-hydroxy-2-(6-methoxyquinolin-4-yl)-ethyl]piperidin-4-ylamino}methyl)-4H-pyrido[3,2-b][1,4]oxazin-3-one Dihydrochloride

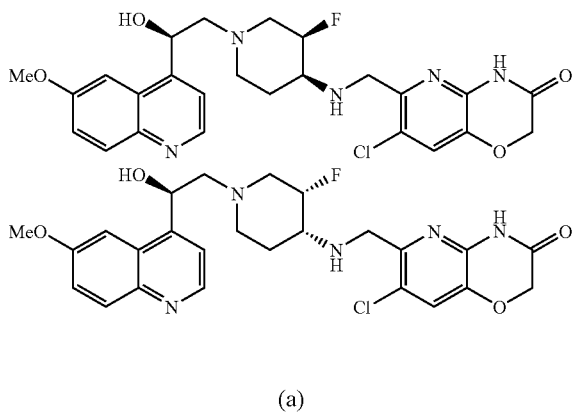

(a) 6-Bromo-7-chloro-4H-pyrido[3,2-b][1,4]oxazin-3-one

6-Bromo-4H-pyrido[3,2-b][1,4]oxazin-3-one (10c) (20 g, 87.7 mmole) was dissolved in DMF (175 mL) and cooled in an ice bath. Chlorine gas was then slowly bubbled in for 45 minutes, and then the saturated solution was stirred in the ice bath for 2 hours. The mixture was purged with nitrogen and slowly added with stirring to 1L of ice water which contained 100 g of $Na_2SO_3$, making sure to keep the temperature <15° C. After stirring 30 minutes the product was filtered, washed thoroughly with water and dried to afford (22.5 g, 98%) of a white solid.

$^1$H NMR (400 MHz, DMSO-$d_6$): 4.76 (2H, s,), 7.78 (1H, s), 11.71 (1H, s).

(b) 7-Chloro-6-((E)-styryl)-4H-pyrido[3,2-b][1,4]oxazin-3-one

6-Bromo-7-chloro-4H-pyrido[3,2-b][1,4]oxazin-3-one (15a) (22 g, 83.7 mmole) and trans-2-phenylvinylboronic acid (17.33 g, 117 mmole) were dissolved in 1,4-dioxane (300 mL) and the solution was degassed with argon. $(Ph_3P)_4Pd$ (1.9 g, 2 mole %) was added, followed by a solution of potassium hydrogen carbonate (21 g, 210 mmole) in $H_2O$ (100 mL). The reaction was heated at reflux under argon overnight, then was cooled to room temperature and diluted with ethyl acetate (1 L). The solution was washed sequentially with $H_2O$ and brine, dried ($Na_2SO_4$), and concentrated in vacuo. The residue was slurried with chloroform (120 mL), then diluted with diethyl ether (100 mL). The precipitated product was collected by filtration and washed with ether to provide the product (16.4 g, 68%) as an off-white solid.

$^1$H NMR (400 MHz, DMSO-$d_6$): 4.71 (2H, s), 7.32-7.46 (3H, m), 7.54-7.74 (4H, m), 11.6 (1H, s).

(c) 7-Chloro-3-oxo-3,4-dihydro-2H-pyrido[3,2-b][1,4]oxazine-6-carboxaldehyde

7-Chloro-6-((E)-styryl)-4H-pyrido[3,2-b][1,4]oxazin-3-one (15b) (8.0 g, 27.9 mmole) was dissolved in a mixture of DMF (400 mL) and methanol (40 mL), and the solution was cooled to −78° C. Ozone was bubbled through the solution with stirring for 45 minutes, then the excess ozone was removed by bubbling oxygen through the solution for 30 min. Dimethylsulfide (21 mL, 279 mmole) was added to the solution, and the reaction was stirred at −78° C. for 3 hr, then at room temperature overnight. The solvent was removed in vacuo, and the residue was triturated with $Et_2O$ (150 mL). The collected solid was washed with additional $Et_2O$ and dried to afford a white solid (4 g, 68%).

$^1$H NMR (400 MHz, DMSO-d6): 4.86 (2H, m), 7.73 (1H, s); 10.05 (1H, s), 11.84 (1H, s).

(d) Title Compounds

The free base of the title compounds were prepared as a 1:1 mixture from amines (12b) and aldehyde (15c) by the method of Example (6h) (60%).

MS (ES) m/z 516 (M+H)$^+$. $^1$H NMR δH (CDCl$_3$, 400 MHz), 1.50-2.00 (4H, m), 2.48-2.98 (6.5H, m), 3.24-3.31 (1H, m), 3.44-3.56 (0.5H, m), 3.91 (3H, s), 4.01 (2H, q), 4.32 (1H, s), 4.87, 4.90 (1H, 2d), 5.43 (1H, dd), 7.16 (1H, d), 7.24 (1H, s), 7.36 (1H, dd), 7.64 (1H, dd), 8.06 (1H, d), 8.78 (1H, d), 9.63 (1H, s).

This material, as a solution in chloroform/methanol, was treated with an excess of 4M HCl in dioxan and evaporated to dryness. The solid was triturated under ether, filtered and dried under vacuum to provide the title compound.

Example 16

6-[({(3S,4S)-3-Fluoro-1-[(R)-2-hydroxy-2-(6-methoxyquinolin-4-yl)-ethyl]piperidin-4-ylamino}methyl)-4H-pyrido[3,2-b][1,4]thiazin-3-one and 6-[({(3R,4R)-3-fluoro-1-[(R)-2-hydroxy-2-(6-methoxyquinolin-4-yl)-ethyl]piperidin-4-ylamino}methyl)-4H-pyrido[3,2-b][1,4]thiazin-3-one Dihydrochloride

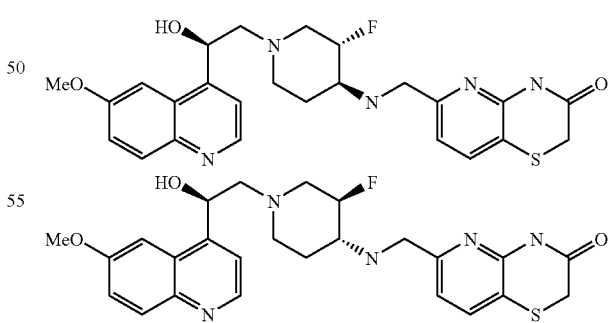

(a) (3S,4S) and (3R,4R)-4-Benzylamino-1-tert-butoxycarbonyl-3-fluoropiperidine

An approximately 1:1 mixture of cis and trans-4-benzylamino-1-tert-butoxycarbonyl-3-fluoropiperidine from Example (6a) (2.2 g) was chromatographed on silica gel (ethyl acetate-hexane) to give the trans-isomer in the early fractions (0.75 g).

(b) 6-[((3S,4S)-3-Fluoro-piperidin-4-ylamino)-methyl]-4H-pyrido[3,2-b][1,4]thiazin-3-one and 6-[((3R,4R)-3-fluoro-piperidin-4-ylamino)-methyl]-4H-pyrido[3,2-b][1,4]thiazin-3-one The trans-amine (16a) (0.7 g) in methanol (30 mL) was hydrogenated over 20% palladium hydroxide on carbon (0.24 g) at 30 psi for 5 h, then filtered through Celite® and evaporated to give the crude piperidine (0.45 g). A portion (0.23 g) was dissolved in DMF (5 mL), methanol (5 mL) and acetic acid (0.5 mL) and aldehyde (6 g) was added and the mixture was heated with 4A sieves at 85° C. for 2 h, cooled, and sodium cyanoborohydride (0.2 g) was added and the mixture stirred at room temperature overnight. It was filtered, sodium carbonate solution was added and the mixture extracted with 10% methanol-chloroform, dried (sodium sulfate), evaporated to dryness, and chromatographed on silica gel (methanol-DCM). The product (0.3 g) was dissolved in DCM (15 mL) and stirred with TFA (15 mL) for 2 h then evaporated. The residue was basified with sodium carbonate solution, extracted with 10% methanol-chloroform and the extracts dried and evaporated to give a foam (0.19 g).

LC/MS (ES) m/z 297 (M+H)$^+$.

(c) Title Compounds

The trans-amine (16b) (0.19 g) and 6-methoxy-4-(R)-oxiranylquinoline (0.129 g) were heated together with DMF (3 drops) at 85° C. for 3 h, then allowed to cool, and the product purified by chromatography on silica gel (methanol-DCM) to give the free base of the title compounds as a 1:1 mixture, as a white solid (0.125 g).

LC/MS (ES) m/z 498 (M+H)$^+$. $^1$H NMR δH (CDCl$_3$, 250 MHz), 1.50-1.90 (4H, m), 2.10-2.98 (6.5H, m), 3.20-3.25 (1H, m), 3.50 (0.5H, m), 3.92 (5H, s and m), 4.45 and 4.78 (total 1H, m), 5.44 (1H, d), 6.95 (1H, d), 7.15 (1H, d), 7.40 (1H, dd), 7.60 (2H, overlapping d), 8.06 (1H, d), 8.50 (1H, br s), 8.80 (1H, d).

This material, as a solution in chloroform/methanol, was treated with an excess of 4M HCl in dioxan and evaporated to dryness. The solid was triturated under ether, filtered and dried under vacuum to provide the title compound.

Example 17

6-[({(3S,4S)-3-Fluoro-1-[(R)-2-hydroxy-2-(6-methoxyquinolin-4-yl)-ethyl]piperidin-4-ylamino}methyl)-4H-pyrido[3,2-b][1,4]oxazin-3-one and 6-[({(3R,4R)-3-fluoro-1-[(R)-2-hydroxy-2-(6-methoxyquinolin-4-yl)-ethyl]piperidin-4-ylamino}methyl)-4H-pyrido[3,2-b][1,4]oxazin-3-one Dihydrochloride

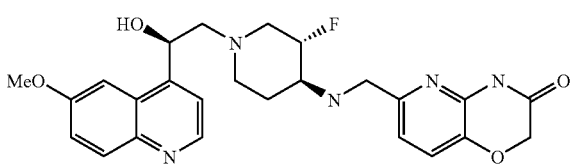

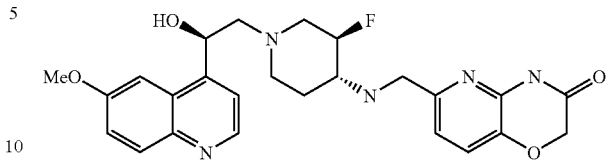

(a) (3S,4S) and (3R,4R)-4-Benzyloxycarbonylamino-3-fluoropiperidine

The trans-amine (16a) (0.7 g) in methanol (25 mL) was hydrogenated over 20% palladium hydroxide on carbon (0.28 g) at 30 psi for 3.5 h, then filtered through Celite® and evaporated to give a foam (0.45 g). The crude amine (0.65 g) was dissolved in DCM (20 mL) containing triethylamine (0.45 mL), cooled in ice, and benzyl chloroformate (0.52 mL) was added and the mixture was stirred at room temperature for 2 h. Sodium carbonate solution was added and the mixture extracted with DCM, dried (sodium sulfate), evaporated to dryness, and chromatographed on silica gel (ethyl acetate-hexane). The product (0.52 g) was dissolved in DCM (15 mL) and stirred with TFA (15 mL) for 2 h then evaporated. The residue was basified with sodium carbonate solution, extracted with 10% methanol in DCM and the extracts dried and evaporated to give a white solid (0.352 g).

LC/MS (ES) m/z 253 (M+H)$^+$.

(b) (3S,4S) and (3R,4R)-2-(4-Amino-3-fluoropiperidin-1-yl)-1-(6-methoxyquinolin-4-yl)-ethanol The trans-amine (17a) (0.34 g) and 6-methoxy-4-(R)-oxiranylquinoline (0.271 g) were heated together with DMF (3 drops) at 85° C. for 3 h, then allowed to cool, and the product purified by chromatography on silica gel. The material obtained (0.28 g) was dissolved in ethanol (30 mL) and hydrogenated with 10% Pd/C (0.25 g) for 4 h, then filtered through Celite® and evaporated to give a foam (0.197 g).

LC/MS (ES) m/z 320 (M+H)$^+$.

(c) Title Compounds

The free base of the title compounds was prepared (45 mg) as a 1:1 mixture from amines (17b) (70 mg) and aldehyde (10e (40 mg) by the method of Example (6h).

MS (ES) m/z 482 (M+H)$^+$. $^1$H NMR δH (CDCl$_3$, 250 MHz), 1.50-1.90 (4H, m), 2.00-2.90 (6.5H, m), 3.10-3.25 (1H, m), 3.50 (0.5H, m), 3.90 (5H, s and m), 4.45 and 4.70 (total 1H, m), 5.46 (1H, d), 6.92 (1H, d), 7.19 (1H, d), 7.20 (1H, d), 7.35 (1H, dd), 7.60 (1H, d), 8.06 (1H, d), 8.80 (1H, d), 9.30 (1H, br s).

This material, as a solution in chloroform/methanol, was treated with an excess of 4M HCl in dioxan and evaporated to dryness. The solid was triturated under ether, filtered and dried under vacuum to provide the title compound.

Example 18

7-Fluoro-6-[({(3S,4S)-3-fluoro-1-[(R)-2-hydroxy-2-(6-methoxyquinolin-4-yl)-ethyl]piperidin-4-ylamino}methyl)-4H-pyrido[3,2-b][1,4]thiazin-3-one and 7-Fluoro-6-[({(3R,4R)-3-fluoro-1-[(R)-2-hydroxy-2-(6-methoxyquinolin-4-yl)-ethyl]piperidin-4-ylamino}methyl)-4H-pyrido[3,2-b][1,4]thiazin-3-one Dihydrochloride

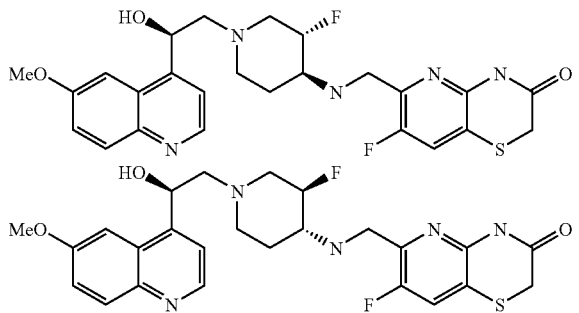

The free base of the title compounds were prepared (57 mg) as a 1:1 mixture from amines (17b) (65 mg) and aldehyde (13f) (48 mg) by the method of Example (6h).

MS (ES) m/z 516 (M+H)+.

$^1$H NMR δH (CDCl$_3$, 250 MHz), 1.50-1.80 (4H, m), 2.10-2.95 (6.5H, m), 3.10-3.30 (1H, m), 3.50 (0.5H, m), 3.90 (3H, s), 4.00 (2H, q), 4.50 and 4.70 (total 1H, m), 5.45 (1H, d), 7.15 (1H, br s), 7.40 (2H, m), 7.62 (1H, d), 8.05 (1H, d), 8.50 (1H, br s), 8.80 (1H, d).

This material, as a solution in chloroform/methanol, was treated with an excess of 4M HCl in dioxan and evaporated to dryness. The solid was triturated under ether, filtered and dried under vacuum to provide the title compound.

Example 19

6-[({(3S,4S)-3-Fluoro-1-[(R)-2-hydroxy-2-(6-methoxyquinolin-4-yl)-ethyl]piperidin-4-ylamino}methyl)-1H-pyrido[2,3-b][1,4]thiazin-3-one and 6-[({(3R,4R)-3-Fluoro-1-[(R)-2-hydroxy-2-(6-methoxyquinolin-4-yl)-ethyl]piperidin-4-ylamino}methyl)-1H-pyrido[2,3-b][1,4]thiazin-3-one Dihydrochloride

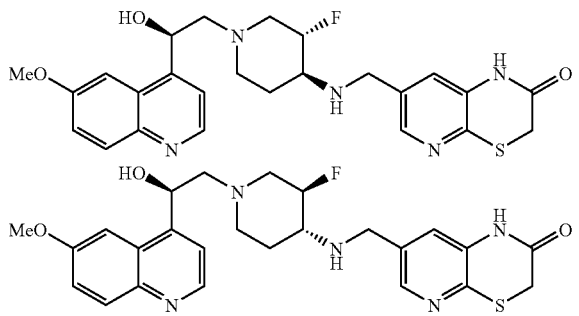

The free base of the title compounds was prepared (38 mg) as a 1:1 mixture from amines (17b) (50 mg) and aldehyde (14e) (32 mg) by the method of Example (6h).

MS (ES) m/z 498 (M+H)+. $^1$H NMR δH (CDCl$_3$, 250 MHz), 1.50-1.80 (m), 1.95-2.90 (6.5H, m), 3.10-3.30 (1H, m), 3.50 (0.5H, m), 3.87 (2H, s), 3.92 (3H, s), 4.40 and 4.65 (total 1H, m), 5.45 (1H, d), 7.15 (2H, m), 7.35 (1H, dd), 7.62 (1H, d), 8.05 (1H, d), 8.15 (1H, s), 8.40 (1H, br s), 8.80 (1H, d).

This material, as a solution in chloroform/methanol, was treated with an excess of 4M HCl in dioxan and evaporated to dryness. The solid was triturated under ether, filtered and dried under vacuum to provide the title compound.

Example 20

6-({cis-3-Fluoro-1-[(R)-2-hydroxy-2-(6-methoxy-[1,5]naphthyridin)-ethyl]piperidin-4-ylamino}methyl)-4H-pyrido[3,2-b][1,4]oxazin-3-one Diastereoisomer 1 Dihydrochloride

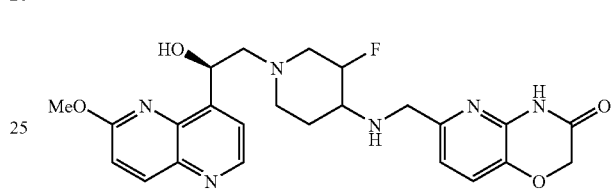

(a) 4-Hydroxy-6-methoxy-[1,5]-naphthyridine

5-Amino-2-methoxypyridine (55 g, 0.44 mol) in methanol (1000 mL) with methyl propiolate (40 mL, 0.44 mol) was stirred for 48 hours, then evaporated and the product purified by chromatography on silica gel (dichloromethane) followed by recrystallisation from dichloromethane-hexane (44.6 g, 48%).

The unsaturated ester (10.5 g, 0.05 mol) in warm Dowtherm A (50 mL) was added over 3 minutes to refluxing Dowtherm A, and after a further 20 minutes at reflux the mixture was cooled and poured into ether. The precipitate was filtered to give a solid (6.26 g, 70%)

(b) Bromomethyl-(6-methoxy-[1,5]-naphthyridin-4-yl)-ketone

The naphthyridine (20a) (10 g, 0.057 mol) in dichloromethane (200 mL) containing 2,6-lutidine (9.94 mL, 0.086 mol) and 4-dimethylaminopyridine (0.07 g, 0.0057 mol) was cooled in ice and treated with trifluoromethanesulfonic anhydride (10.5 mL, 0.063 mol). After stirring for 2.5 hours the mixture was washed with saturated ammonium chloride solution, dried, evaporated and purified on silica (dichloromethane). The triflate (13.2 g, 0.044 mol) in DMF (20 mL) with triethylamine (12 ml, 0.086 mol) butyl vinyl ether (22 mL, 0.17 mol), palladium (0) acetate (0.97 g, 0.0044 mol) and 1,3-bis(diphenylphosphino)propane (1.77 g, 0.0044 mol) was heated at 60° C. for 3 hours then evaporated and chromatographed on silica gel (dichloromethane) to give a yellow solid (10.7 g, 95%). This was dissolved in THF (250 mL), water (40 mL) and treated with N-bromosuccinimide (7.4 g, 0.042 mol) for 1 hour, then evaporated and chromatographed on silica gel (dichloromethane) to give the ketone (10.42 g, 98%).

(c) (R)-2-Bromo-1-(6-methoxy-[1,5]-naphthyridinyl)ethanol

The ketone (20b) (6.6 g, 0.023 mol) in toluene was treated with (+)-B-chlorodiisopinocamphenylborane ((+)-DIP-chloride) (12 g, 0.037 mol) and stirred overnight, then diethanolamine (15 g, 0.14 mol) was added and the mixture stirred for 3 hours, filtered and evaporated. Chromatography on silica gel (ethyl acetate-hexane) gave a white solid (4.73 g, 73%).

(d) (R)-2-(6-Methoxy-[1,5]-naphthyridin-4-yl)oxirane

The alcohol (20c) (4.8 g, 0.017 mol) in methanol (20 mL) was stirred with potassium carbonate (2.6 g, 0.019 mol) for 1 hour, then evaporated and chromatographed on silica gel (ethyl acetate-hexane-dichloromethane) to give a solid (3.14 g, 92%), (Batches typically >90% ee by chiral HPLC).

MS (+ve ion electrospray) m/z 203 (MH+).

(e) (R)-2-(4-Amino-3-fluoropiperidin-1-yl)-1-(6-methoxy-[1,5]naphthyridin-4-yl)-ethanol Diastereoisomer 1 cis-4-Benzyloxycarbonylamino-3-fluoropiperidine Enantiomer 1 (6b) (2.49 g) and (R)-2-(6-Methoxy-[1,5]-naphthyridin-4-yl)oxirane (20d) (100% ee) (2.0 g) were heated together at 80-88° C. for 2.5 h with 2 drops of DMF, then allowed to cool, and the product purified on silica gel (methanol-DCM) to give a solid (3.88 g). The material was dissolved in ethanol (40 mL), 1,4-cyclohexadiene (7.7 mL) was added and the solution was stirred at room temperature with 10% Pd/C (3.5 g) for 2 h, then filtered through Celite® and evaporated to give a foam (2.53 g).

LC/MS (ES) m/z 321 (M+H)$^+$.

(f) Title Compound

The free base of the title compound was prepared from amine (20e) and aldehyde (10e) by the method of Example (6h) (75%).

LC/MS (ES) m/z 483 (M+H)$^+$. $^1$H NMR δH (CDCl$_3$, 250 MHz), 1.70-1.9 (2H, m), 2.30-2.90 (5H, m), 3.15 (1H, dd), 3.55 (1H, m), 3.90 (2H, s), 4.01 (3H, s), 4.62 (2H, s), 4.85 (1H, d), 5.70 (1H, dd), 6.98 (1H, d), 7.12 (1H, d), 7.25 (1H, d), 7.80 (1H, d), 8.20 (1H, d), 8.70 (1H, br s), 8.80 (1H, d).

This material, as a solution in chloroform/methanol, was treated with an excess of 4M HCl in dioxan and evaporated to dryness. The solid was triturated under ether, filtered and dried under vacuum to provide the title compound.

Example 21

6-({cis-3-Fluoro-1-[(R)-2-hydroxy-2-(6-methoxy-[1,5]naphthyridin)-ethyl]piperidin-4-ylamino}methyl)-4H-pyrido[3,2-b][1,4]oxazin-3-one Diastereoisomer 2 Dihydrochloride

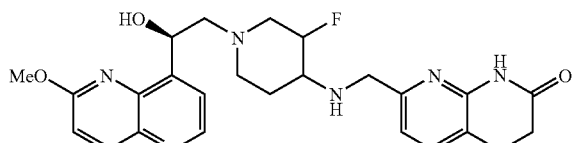

(a) (R)-2-(4-Amino-3-fluoropiperidin-1-yl)-1-(6-methoxy-[1,5]naphthyridin-4-yl)-ethanol Diastereoisomer 2

This was prepared from cis-4-benzyloxycarbonylamino-3-fluoropiperidine Enantiomer 2 (7a) and (R)-2-(6-methoxy-[1,5]-naphthyridin-4-yl)oxirane (20d) (100% ee) by the method of Example (20e).

LC/MS (ES) m/z 321 (M+H)$^+$.

(b) Title Compound

The free base of the title compound was prepared from amine (21a) and aldehyde (10e) by the method of Example (6h) (63%).

LC/MS (ES) m/z 483 (M+H)$^+$. $^1$H NMR δH (CDCl$_3$, 250 MHz), 1.70-1.9 (2H, m), 2.20-2.90 (5H, m), 3.15 (1H, dd), 3.25 (1H, m), 3.88 (2H, s), 4.01 (3H, s), 4.62 (2H, s), 4.80 (1H, d), 5.70 (1H, dd), 6.98 (1H, d), 7.12 (1H, d), 7.25 (1H, d), 7.80 (1H, d), 8.22 (1H, d), 8.75-(1H, br s), 8.80 (1H, d).

This material, as a solution in chloroform/methanol, was treated with an excess of 4M HCl in dioxan and evaporated to dryness. The solid was triturated under ether, filtered and dried under vacuum to provide the title compound.

Example 22

6-({cis-3-Fluoro-1-[(R)-2-hydroxy-2-(6-methoxy-[1,5]naphthyridin)-ethyl]piperidin-4-ylamino}methyl)-4H-pyrido[3,2-b][1,4]thiazin-3-one Diastereoisomer 1 Dihydrochloride

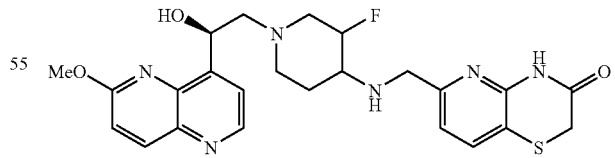

The free base of the title compound was prepared from amine (20e) and aldehyde (6g) by the method of Example (6h) (58%).

LC/MS (ES) m/z 499 (M+H)$^+$. $^1$H NMR δH (CDCl$_3$, 400 MHz), 1.67-2.02 (6H, m), 2.39-2.55 (3H, m), 2.67-2.81 (1H, m), 2.84-2.92 (1H, m), 3.15 (1H, dd), 3.44-3.59 (1H, m), 3.90 (2H, s), 4.03 (3H, s), 4.85 (1H, d), 5.71 (1H, dd), 7.04

(1H, d), 7.12 (1H, d), 7.58 (1H, d), 7.79 (1H, d), 8.22 (1H, d), 8.35 (1H, s), 8.78 (1H, d).

This material, as a solution in chloroform/methanol, was treated with an excess of 4M HCl in dioxan and evaporated to dryness. The solid was triturated under ether, filtered and dried under vacuum to provide the title compound.

Example 23

6-({cis-3-Fluoro-1-[(R)-2-hydroxy-2-(6-methoxy-[,5]naphthyridin)-ethyl]piperidin-4-ylamino}methyl)-4H-pyrido[3,2-b][1,4]thiazin-3-one Diastereoisomer 2 Dihydrochloride

The free base of the title compound was prepared from amine (21a) and aldehyde (6g) by the method of Example (6h) (71%).

LC/MS (ES) m/z 499 (M+H)+. $^1$H NMR δH (CDCl$_3$, 250 MHz), 1.70-2.00 (2H, m), 2.20-2.90 (5H, m), 3.15 (1H, dd), 3.25 (1H, m), 3.45 (2H, s), 3.90 (2H, s), 4.05 (3H, s), 4.81 (1H, d), 5.75 (1H, dd), 7.05 (1H, d), 7.12 (1H, d), 7.60 (1H, d), 7.85 (1H, d), 8.22 (1H, d), 8.75 (1H, br s), 8.80 (1H, d).

This material, as a solution in chloroform/methanol, was treated with an excess of 4M HCl in dioxan and evaporated to dryness. The solid was triturated under ether, filtered and dried under vacuum to provide the title compound.

Example 24

7-Chloro-6-({cis-3-fluoro-1-[(R)-2-hydroxy-2-(6-methoxy-[1,5]naphthyridin)-ethyl]piperidin-4-ylamino}methyl)-4H-pyrido[3,2-b][1,4]oxazin-3-one Diastereoisomer 1 Dihydrochloride

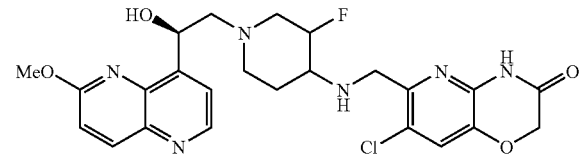

The free base of the title compound was prepared from amine (20e) and aldehyde (15c) by the method of Example (6h) (70%).

LC/MS (ES) m/z 517 (M+H)+. $^1$H NMR δH (CDCl$_3$, 400 MHz), 1.82-2.03 (2H, m), 2.20-2.95 (5H, m), 3.12 (1H, m), 3.54 (1H, m), 3.98-4.02 (4H, m), 4.60 (2H, s), 4.90 (1H, d), 5.72 (1H, m), 7.08 (1H, d), 7.21 (1H, s), 7.81 (1H, d), 8.24 (1H, d), 8.79 (1H, d).

This material, as a solution in chloroform/methanol, was treated with an excess of 4M HCl in dioxan and evaporated to dryness. The solid was triturated under ether, filtered and dried under vacuum to provide the title compound.

Example 25

7-Chloro-6-({cis-3-fluoro-1-[(R)-2-hydroxy-2-(6-methoxy-[1,5]naphthyridin)-ethyl]piperidin-4-ylamino}methyl)-4H-pyrido[3,2-b][1,4]oxazin-3-one Diastereoisomer 2 Dihydrochloride

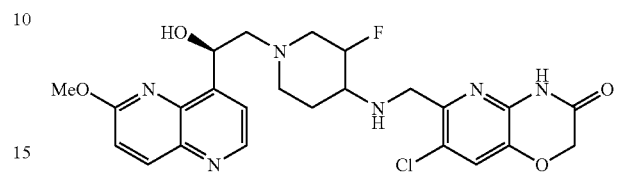

The free base of the title compound was prepared from amine (21a) and aldehyde (15c) by the method of Example (6h) (68%).

LC/MS (ES) m/z 517 (M+H)+. $^1$H NMR δH (CDCl$_3$, 250 MHz), 1.85-1.95 (2H, m), 2.20-2.90 (5H, m), 3.15 (1H, dd), 3.32 (1H, m), 4.01 (5H, s and m overlapping), 4.62 (2H, s), 4.88 (1H, d), 5.78 (1H, dd), 7.10 (1H, d), 7.25 (1H, s), 7.83 (1H, d), 8.25 (1H, d), 8.80 (1H, d).

This material, as a solution in chloroform/methanol, was treated with an excess of 4M HCl in dioxan and evaporated to dryness. The solid was triturated under ether, filtered and dried under vacuum to provide the title compound.

Example 26

6-({cis-3-Fluoro-1-[(R)-2-hydroxy-2-(8-fluoro-6-methoxy-quinolin-4-yl)-ethyl]piperidin-4-ylamino}methyl)-4H-pyrido[3,2-b][1,4]oxazin-3-one Diastereoisomer 1 Dihydrochloride

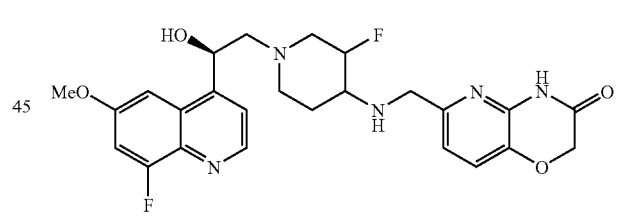

(a) 8-Fluoro-6-methoxy-quinolin-4-ol

2-Fluoro-4-methoxy-phenylamine (3.80 g; 26.7 mmol) and methyl propiolate (2.37 mL, 0.267 mol) in methanol (100 mL) was stirred for 72 hours at room temperature, then heated at 50° C. for 24 hours. It was evaporated and the product purified by chromatography on silica gel (dichloromethane) to give a solid (1.66 g), a portion of which was recrystallised from dichloromethane-hexane.

The unsaturated ester (0.96 g) in warm Dowtherm A (5 mL) was added over 3 minutes to refluxing Dowtherm A (15 mL), and after a further 20 minutes at reflux the mixture was cooled and poured into ether. The precipitate was filtered to give a solid (0.50 g, 61%)

(b) Bromomethyl-(8-fluoro-6-methoxy-quinolin-4-yl)-ketone

This was prepared from (26a) by the method of Example (20b).
MS (+ve ion electrospray) m/z 298/300 (MH+).

(c) 8-Fluoro-6-methoxy-4(R)-oxiranyl-quinoline

The bromomethyl ketone (26b) (8.6 g) was converted to the oxirane (1.04 g) by the methods of Examples (20c,d).
MS (+ve ion electrospray) m/z 220 (MH+).

(d) (R)-2-(4-Amino-3-fluoropiperidin-1-yl)-1-(8-fluoro-6-methoxyquinolin-4-yl)-ethanol Diastereoisomer 1

This was prepared from amine (6b) (99% ee) and epoxide (26c) (97% ee) followed by transfer hydrogenation over 10% Pd/C as described in Example (20e) to give the product as a foam (70%).
MS (ES) m/z 472 (M+H)+.

(e) Title Compound

The free base of the title compound was prepared from amine (26d) and aldehyde (10e) by the method of Example (6h) (65%).
LC/MS (ES) m/z 500 (M+H)+.
1H NMR δH (CDCl3, 250 MHz), 1.80-1.95 (2H, m), 2.35-2.95 (6H, m), 3.45 (1H, m), 3.88 (2H, s) 3.90 (3H, m), 4.28 (1H, br s), 4.63 (2H, s), 4.88 (1H, d), 5.37 (1H, dd), 7.00 (2H, br d), 7.10 (1H, d), 7.20 (1H, d), 7.70 (1H, d), 8.80 (1H, d), 9.00 (1H, br s).

This material, as a solution in chloroform/methanol, was treated with an excess of 4M HCl in dioxan and evaporated to dryness. The solid was triturated under ether, filtered and dried under vacuum to provide the title compound.

Example 27

6-({cis-3-Fluoro-1-[(R)-2-hydroxy-2-(8-fluoro-6-methoxy-quinolin-4-yl)-ethyl]piperidin-4-ylamino}methyl)-4H-pyrido[3,2-b][1,4]thiazin-3-one Diastereoisomer 1 Dihydrochloride

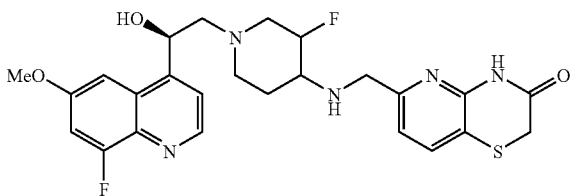

The free base of the title compound was prepared from amine (26d) and aldehyde (6g) by the method of Example (6h) (63%).
LC/MS (ES) m/z 516 (M+H)+. 1H NMR δH (CDCl3, 400 MHz), 1.80-1.95 (2H, m), 2.35-2.95 (6H, m), 3.45 (3H, s and m overlapping), 3.88 (2H, s) 3.90 (3H, m), 4.20 (1H, br s), 4.88 (1H, d), 5.38 (1H, dd), 6.98 (1H, s), 7.03 (1H, d), 7.10 (1H, d), 7.60 (1H, d), 7.70 (1H, d), ), 8.42 (1H, br s) 8.80 (1H, d).

This material, as a solution in chloroform/methanol, was treated with an excess of 4M HCl in dioxan and evaporated to dryness. The solid was triturated under ether, filtered and dried under vacuum to provide the title compound.

Example 28

6-({(3R,4S)-1-[2-(3-Chloro-6-methoxy-quinolin-4-yl)-ethyl]-3-fluoro-piperidin-4-ylamino}methyl)-4H-pyrido[3,2-b][1,4]thiazin-3-one and 6-({(3S,4R)-1-[2-(3-Chloro-6-methoxy-quinolin-4-yl)-ethyl]-3-fluoro-piperidin-4-ylamino}methyl)-4H-pyrido [3,2-b][1,4]thiazin-3-one Dihydrochloride

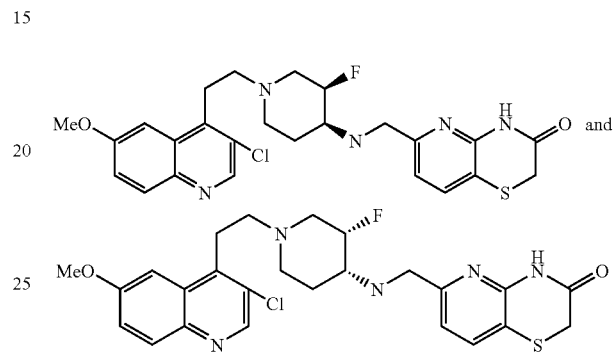

(a) 4-Bromo-3-chloro-6-methoxy-quinoline

3-Chloro-6-methoxy-quinolin-4-ol was prepared as described in WO 02\40474 by heating 6-methoxy-quinolin-4-ol with N-chloro-succinimide in acetic acid at 65° C. (96%) and (11 g) in dry DMF (80 mL) cooled in ice, was treated with phosphorus tribromide (15.6 g) and stirred at room temperature for 3.5 h. It was treated with iced-water, basified with sodium carbonate solution, and the solid collected and washed with water and dried in vacuo to afford a yellow solid (13.2 g).
LC/MS (ES) m/z 272/274/276 (M+H)+.

(b) 3-Chloro-6-methoxy-4-vinyl-quinoline

The bromo-quinoline (28a) (1.0 g) in de-gassed toluene (17 mL) was treated with tetrakis(triphenylphosphine)palladium(0) (212 mg), vinyltributyltin (1.3 mL) and lithium chloride (462 mg) and the mixture was heated under reflux for 5 h. It was evaporated to dryness and chromatographed on silica gel (hexane then ethyl acetate-DCM) to afford a solid (0.9 g).
LC/MS (ES) m/z 220/222 (M+H)+.

(c) (3R,4S)-1-[2-(3-Chloro-6-methyl-quinolin-4-yl)-ethyl]-3-fluoro-piperidin-4-ylamine and (3S,4R)-1-[2-(3-chloro-6-methyl-quinolin-4-yl)-ethyl]-3-fluoro-piperidin-4-ylamine The 4-vinyl-quinoline (28b)(0.5 g) and (3R,4S) and (3S,4R)-4-benzyloxycarbonylamino-3-fluoropiperidine (12a) (0.574 g) were heated in chloroform (2 mL) for 24 h and chromatographed on silica gel (ethyl acetate-DCM then methanol-DCM) and the product hydrogenated in dioxan (15 mL) over 10% palladium-carbon, filtered and evaporated to dryness to afford a foam (0.25 g).

(d) Title Compounds

The free base of the title compounds were prepared as a 1:1 mixture from amine (28c) and aldehyde (6g) by the method of Example (6h) (13%).

¹H NMR δH (CD₃OD, 250 MHz), 1.80-2.80 (7H, m), 3.15 (1H, m), 3.45 (5H, s and m overlapping), 3.90 (2H, s), 3.98 (3H, m), 4.92 (1H, d), 7.05 (1H, d), 7.40 (2H, m), 7.70 (1H, d), 7.92 (1H, d), 8.60 (1H, s).

This material, as a solution in chloroform/methanol, was treated with an excess of 1M HCl in ether and evaporated to dryness. The solid was triturated under ether, filtered and dried under vacuum to provide the title compound.

Example 29

6-({(3R,4S)-3-Fluoro-1-[2-(6-methoxy-[1,5]naphthyridin-4-yl)-ethyl]-piperidin-4-ylamino}-methyl)-4H-pyrido[3,2-b][1,4]thiazin-3-one and 6-({(3S,4R)-3-fluoro-1-[2-(6-methoxy-[1,5]naphthyridin-4-yl)-ethyl]-piperidin-4-ylamino}-methyl)-4H-pyrido[3,2-b][1,4]thiazin-3-one Dihydrochloride

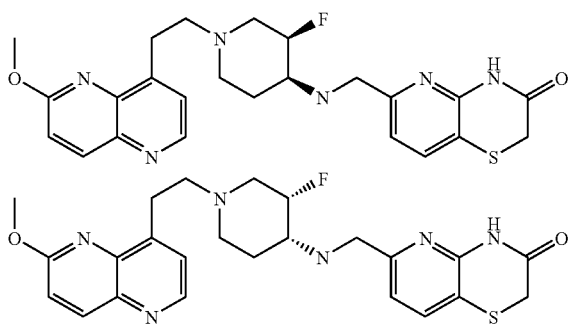

(a) 6-Methoxy-4-vinyl-[1,5]naphthyridine

The naphthyridine-4-triflate (see Example 20b) was reacted with tetrakis(triphenylphosphine)palladium(0) and vinyltributyltin by the method of Example (28b) to give a solid (53%).

LC/MS (ES) m/z 187 (M+H)⁺.

(b) (3R,4S)-3-Fluoro-1-[2-(6-methoxy-[1,5]naphthyridin-4-yl)-ethyl]-piperidin-4-ylamine and (3S,4R)-3-Fluoro-1-[2-(6-methoxy-[1,5]naphthyridin-4-yl)-ethyl]-piperidin-4-ylamine The 4-vinyl-naphthyridine (29a)(1.4 g) and (3R,4S) and (3S,4R)-4-benzyloxycarbonylamino-3-fluoropiperidine (12a) (1.5 g) were heated together neat at 110-120° C. for 24 h and chromatographed on silica gel (hexane-DCM then methanol-DCM) and the product (1.03 g) hydrogenated in dioxan (25 mL) over 10% palladium-carbon at atmospheric pressure, then at 50 psi with fresh catalyst, filtered and evaporated to dryness to afford a foam (0.62 g).

(c) Title Compounds

The free base of the title compounds were prepared as a 1:1 mixture from amine (29b) and aldehyde (6g) by the method of Example (6h) (19%).

LC/MS (ES) m/z 483 (M+H)⁺. ¹H NMR 5H (CDCl₃, 400 MHz), 1.80-2.80 (7H, m), 3.15 (1H, m), 3.48 (3H m), 3.48 (2H, s), 3.95 (2H, s) 4.08 (3H, m), 4.85 (1H, d), 7.05 (1H, d), 7.05 (1H, d), 7.10 (1H, d), 7.41 (1H, d), 7.60 (1H, d), 8.20 (1H, d), 8.68 (1H, d), 9.80 (1H, br s).

This material, as a solution in chloroform/methanol, was treated with an excess of 1M HCl in ether and evaporated to dryness. The solid was triturated under ether, filtered and dried under vacuum to provide the title compound.

Example 30

6-[({(3S,4R)-3-Fluoro-1-[(S)-2-hydroxy-2-(6-methoxyquinolin-4-yl)-ethyl]piperidin-4-ylamino}methyl)-4H-pyrido[3,2-b][1,4]thiazin-3-one and 6-[({(3R,4S-3-fluoro-1-[(S)-2-hydroxy-2-(6-methoxyquinolin-4-yl)-ethyl]piperidin-4-ylamino}methyl)-4H-pyrido[3,2-b][1,4]thiazin-3-one Dihydrochloride

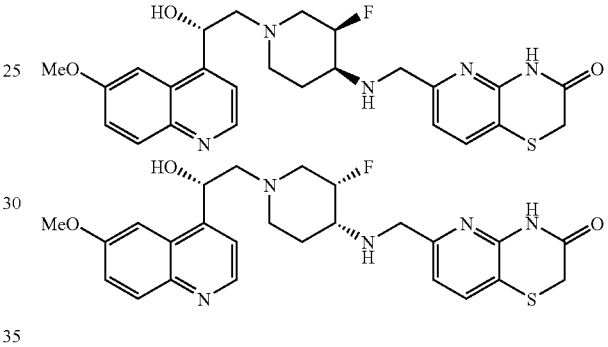

(a) 6-Methoxy-4-(S)-oxiranyl-quinoline

This was prepared by the method of Example (4c) using (−)-B-chlorodiisopinocamphenylborane [(−)-DIP chloride] as the reducing agent, to give a solid (98% ee).

(b) (S)-2-(3R,4S)-(4-Amino-3-fluoropiperidin-1-yl)-1-(6-methoxyquinolin-4-yl)-ethanol and (S)-2-(3S,4R)-(4-Amino-3-fluoropiperidin-1-yl)-1-(6-methoxyquinolin-4-yl)-ethanol (3R,4S) and (3S,4R)-4-Benzyloxycarbonylamino-3-fluoropiperidine (12a), prepared as described in Examples (6a,b) was reacted with epoxide (30a) and then hydrogenated as described in Example (6c) to give a pale yellow foam (66% overall).

(c) Title Compounds

The free base of the title compounds were prepared as a 1:1 mixture from amines (30b) and aldehyde (6g) by the method of Example (6h) (34%).

MS (ES) m/z 498 (M+H)⁺. ¹H NMR δH ((CD₃)₂SO, 400 MHz), 1.60-1.80 (2H, m), 2.20-2.80 (5H, m), 2.98 (1H, m), 3.21 (1H, m), 3.52 (2H s), 3.78 (2H, s), 3.92 (3H, s), 4.72 (1H, d), 5.40 (2H, m), 7.09 (1H, d), 7.40 (2H, m), 7.57 (1H, d), 7.74 (1H, d), 7.95 (1H, d), 8.73 (1H, d), 10.90 (1H, s).

This material, as a solution in chloroform/methanol, was treated with an excess of 4M HCl in dioxan and evaporated to dryness. The solid was triturated under ether, filtered and dried under vacuum to provide the title compound.

Example 31

6-({(3R,4S)-1-[2-(2,3-Dihydro-[1,4]dioxino[2,3-f]quinolin-10-yl)-ethyl]-3-fluoro-piperidin-4-ylamino}-methyl)-4H-pyrido[3,2-b][1,4]thiazin-3-one and 6-({(3S,4R)-1-[2-(2,3-dihydro-[1,4]dioxino[2,3-f]quinolin-10-yl)-ethyl]-3-fluoro-piperidin-4-ylamino}-methyl)-4H-pyrido[3,2-b][1,4]thiazin-3-one Dihydrochloride

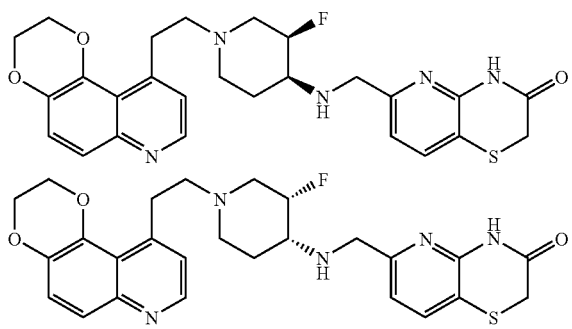

(a) 7-Bromo-2,3-dihydro-benzo[1,4]dioxin-6-ylamine

A solution of 2,3-dihydro-benzo[1,4]dioxin-6-ylamine (32 g, 212 mmol) in dichloromethane (1 litre) was treated with a solution of bromine (10.8 mL, 212 mmol) in dichloromethane (100 mL) at 0° C. After the addition the mixture was stirred at room temperature for 1 hour then washed with saturated aqueous sodium bicarbonate solution containing a small amount of sodium sulphite. The organic extract was dried and evaporated to an oil that was chromatographed on silica gel eluting with dichloromethane to afford an oil (14.8 g, 30%).

MS (+ve ion electrospray) m/z 231 (MH+).

(b) 5-[(7-Bromo-2,3-dihydro-benzo[1,4]dioxin-6-ylamino)-methylene]-2,2-dimethyl-[1,3]dioxane-4,6-dione A mixture of aniline (31a) (14.8 g, 64.3 mmol), triethyl orthoformate (12.7 mL, 77.2 mmol) and 2,2-dimethyl-[1,3]dioxane-4,6-dione (Meldrum's acid) (11.1 g, 77.2 mmol) in ethanol (70 mL) was heated to reflux. After 1 hour the mixture was allowed to cool to room temperature then filtered, washing with ethanol then ether, to afford a white solid (22.9 g, 93%).

MS (+ve ion electrospray) m/z 385 (H+).

(c) 6-Bromo-2,3-dihydro-7H-[1,4]dioxino[2,3-f]quinolin-10-one

Enamine (31b) (22.9 g) was added portionwise to refluxing Dowtherm A (45 mL) over 3 minutes. After a further 3 minutes at reflux the mixture was cooled to room temperature. Ethyl acetate/hexane (10 mL/20 mL) was added and a black solid isolated by filtration. This residue was dissolved in hot methanol (400 mL) and filtered through Keiselguhr. Water (800 mL) was added and the mixture stored at 5° C. overnight. Filtration and drying afforded a pale yellow solid (10.3 g, 61%).

MS (APCI−) m/z 281 [M−H]−

(d) 2,3-Dihydro-7H-[1,4]dioxino[2,3-f]quinolin-10-one

A suspension of (31c) (3.4 g, 12 mmol) in water/dioxan (150 mL/80 mL) was treated with 1M aqueous sodium hydroxide solution then hydrogenated over 10% palladium on charcoal (1.5 g) for 20 hours. The mixture was filtered then acidified with 5M aqueous hydrochloric acid. On concentrating to ca 100 mL, a solid began to crystallise out. The mixture was stored at 5° C. overnight. Filtration and drying afforded a pale yellow solid (2.8 g, 100%).

MS (APCI−) m/z 202 [M−H]−

(e) 10-Bromo-2,3-dihydro-[1,4]dioxino[2,3-f]quinoline

A mixture of (31d) (2.5 g) and phosphorus oxybromide (7.8 g) was heated at 120° C. for 0.75 hour. After cooling to room temperature the mixture was treated with water, basified with potassium carbonate and extracted with ethyl acetate. The organic extract was dried and evaporated to afford an oil (475 mg, 14%).

MS (+ve ion electrospray) m/z 268 (MH+).

(f) 10-Vinyl-2,3-dihydro-[1,4]dioxino[2,3-f]quinoline

The bromide (31e) was reacted with tetrakis(triphenylphosphine)palladium(0) and vinyltributyltin in toluene and DMF at 115-130° C., by the method of Example (28b) to give a solid (100%).

LC/MS (ES) m/z 214 (M+H)+.

(g) (3R,4S)-1-[2-(2,3-Dihydro-[1,4]dioxino[2,3-f]quinolin-10-yl)-ethyl]-3-fluoro-piperidin-4-ylamine and (3S,4R)-1-[2-(2,3-Dihydro-[1,4]dioxino[2,3-f]quinolin-10-yl)-ethyl]-3-fluoro-piperidin-4-ylamine The 10-vinyl-quinoline (31f)(0.373 g) and (3R,4S) and (3S,4R)-4-benzyloxycarbonylamino-3-fluoropiperidine (12a) (0.44 g) were heated together at 120° C. for 24 h and chromatographed on silica gel (hexane then methanol-DCM) and the product (0.48 g) hydrogenated in ethanol (30 mL) over 10% palladium-carbon, filtered and evaporated to dryness to afford a foam (0.24 g).

LC/MS (ES) m/z 332 (M+H)+.

(h) Title Compounds

The free base of the title compounds were prepared as a 1:1 mixture from amine (31 g) and aldehyde (6g) by the method of Example (6h) (27%).

LC/MS (ES) m/z 510 (M+H)+.

$^1$H NMR δH (CDCl$_3$, 250 MHz), 1.80-2.80 (7H, m), 3.05 (1H, m), 3.10-3.70 (3H m), 3.50 (2H, s), 3.95 (2H, m) 4.35 (4H, s), 4.8 (1H, m), 7.10 (2H, m), 7.30 (1H, d), 7.60 (1H, d), 7.65 (1H, d), 8.60 (1H, d), 9.70 (1H, br s).

This material, as a solution in chloroform/methanol, was treated with an excess of 1M HCl in ether and evaporated to dryness. The solid was triturated under ether, filtered and dried under vacuum to provide the title compound.

Example 32

6-({(3R,4S)-1-[2-(6,8-Difluoro-quinolin-4-yl)-
ethyl]-3-fluoro-piperidin-4-ylamino}-methyl)-4H-
pyrido[3,2-b][1,4]thiazin-3-one and 6-({(3S,4R)-1-
[2-(6,8-difluoro-quinolin-4-yl)-ethyl]-3-fluoro-
piperidin-4-ylamino}-methyl)-4H-pyrido[3,2-b][1,4]
thiazin-3-one Dihydrochloride

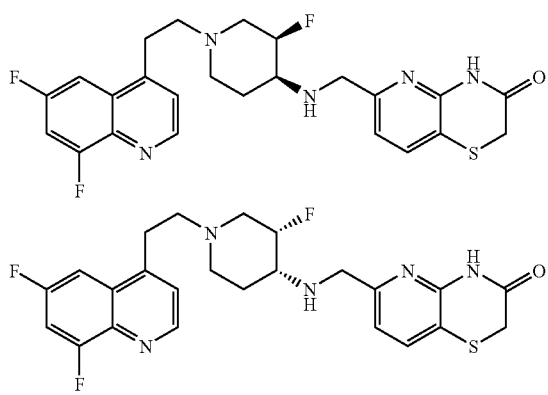

(a) 4-Bromo-6,8-difluoro-quinoline 6,8-Difluoro-quinolin-4-ol (commercially available) (7.43 g) in DMF (200 mL) was treated with phosphorus tribromide (4.24 mL) by the method of Example (28a) to give a solid (9.03 g).

LC/MS (ES) m/Z 245 (M+H)$^+$.

(b) 6,8-Difluoro-4-vinyl-quinoline

This was prepared by the method of I. Perez et al. (J. Am. Chem. Soc. 2001, 123, 4155-4160). Indium trichloride (1.051 g) in THF (20 mL) was cooled to −78° C. and vinylmagnesium bromide (1M in THF, 14.26 mL) was added and the solution was stirred at room temperature for 0.5 h. The 4-bromoquinoline (32a) (1.051 g) and [1,1'-bis (diphenyl-phosphino]ferrocene palladium(II) chloride 1:1 complex with DCM (70.6 mg) in THF (20 mL) were added and the mixture was heated under reflux for 2 h. It was filtered and ethyl acetate added and the organic fraction washed with water, dried and evaporated to dryness to afford a solid that was used in the next stage without purification.

LC/MS (ES) m/z 192 (M+H)$^+$.

(c) (3R,4S)-1-[2-(6,8-Difluoro-quinolin-4-yl)-ethyl]-3-fluoro-piperidin-4-ylamine and (3S,4R)-1-[2-(6,8-difluoro-quinolin-4-yl)-ethyl]-3-fluoro-piperidin-4-ylamine The 4-vinyl-quinoline (32b) (0.729 g) and (3R,4S) and (3S,4R)-4-benzyloxycarbonylamino-3-fluoropiperidine (12a) (0.962 g) were heated together at 100° C. for 24 h and chromatographed on silica gel (methanol-DCM) to give the product (0.86 g). A portion (0.39 g) was treated with 1,4-cyclohexadiene (0.72 g), and 10% palladium-carbon (0.35 g) in ethanol (5 mL) at room temperature overnight, filtered and evaporated to dryness to afford a foam (0.29 g).

LC/MS (ES) m/z 310 (M+H)$^+$.

(d) Title Compounds

The free base of the title compounds were prepared as a 1:1 mixture from amine (32c) and aldehyde (6g) by the method of Example (6h) (29%).

LC/MS (ES) m/z 510 (M+H)$^+$. $^1$H NMR δH (CD$_3$OD, 400 MHz), 1.80-1.95 (2H, m), 2.20-2.40 (3H, m), 2.70-2.90 (3H m), 3.10 (1H, m), 3.25-3.45 (3H, m), 3.50 (2H, s), 3.95 (2H, m) 4.90 (1H, d), 7.05 (1H, d), 7.45 (1H, m), 7.52 (1H, d), 7.69 (1H, d), 7.75 (1H, d), 8.71 (1H, d).

This material, as a solution in chloroform/methanol, was treated with an excess of 4M HCl in dioxan and evaporated to dryness. The solid was triturated under ether, filtered and dried under vacuum to provide the title compound.

Example 33

6-[({(3S,4R)-3-Fluoro-1-[(R)-2-hydroxy-2-(6-meth-
oxy-[1,5]naphthyridin-4-yl)-ethyl]piperidin-4-
ylamino}methyl)-4H-benzo[1,4]thiazin-3-one and
6-[({(3R,4S)-3-Fluoro-1-[(R)-2-hydroxy-2-(6-meth-
oxy-[1,5]naphthyridin-4-yl)-ethyl]piperidin-4-
ylamino}methyl)-4H-benzo[1,4]thiazin-3-one Bis-
trifluoroacetate

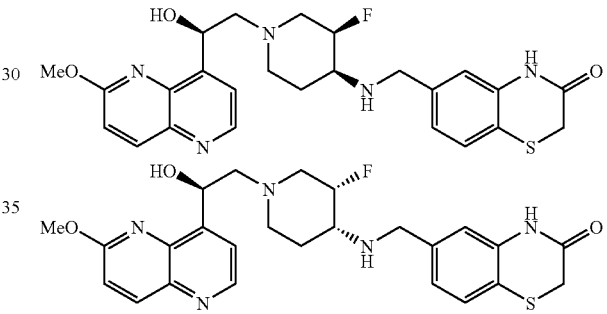

(a) (3S,4R) and (3R,4RS)-6-[(3-Fluoro-piperidin-4-ylamino)-methyl]-4H-benzo[1,4]thiazin-3-one A solution of cis-4-amino-1-tert-butoxycarbonyl-3-fluoropiperidine (5a) (340 mg, 1.60 mmole) in ClCH$_2$CH$_2$Cl (8 mL) and EtOH (0.8 mL) was treated with anhydrous Na$_2$SO$_4$ (450 mg) and 3-oxo-3,4-dihydro-2-benzo[1,4]thiazine-6-carboxaldehyde (1n) (330 mg, 1.80 mmole). The resulting solution was stirred at room temperature for 6 hr, then sodium triacetoxy borohydride (500 mg, 2.40 mmole) was added. The resulting slurry was stirred at room temperature for a further 10 hr, then was quenched by the addition of water (2 mL) and the volatiles were removed in vacuo. The residue was partitioned between EtOAc (2×50 mL) and brine (20 mL). The organic phases were combined, dried (MgSO$_4$), and concentrated in vacuo. The residue was passed through a column of silica gel (100% ethyl acetate), the eluant was concentrated in vacuo and the residue was disolved in 10 mL of CH$_2$Cl$_2$ and treated with 1.25 mL of 4N HCl in dioxane for 2 h. The volitiles were removed in vacuo and the residue was dissolved in 10 mL of CH$_3$OH. MP-carbonate resin (1.08 g) was added and stirred at rt for 1 h. The reaction was filtered to remove the resin and concentration under reduced pressure gave the desired compound as a white solid:

MS (+ve ion electrospray) m/z 296 (MH+)

(b) Title Compound

To an enantiomeric mixture of piperidines (33a) (130 mg, 0.44 mmole) in EtOH (2 mL) was added and [R]-2-(6-methoxynaphthyridin-4-yl)oxirane (20d) (90 mg, 0.44 mmole). The reaction was heated at 80° C. for 18 h, cooled to room temperature and concentrated under reduced pressure. The residue was purified by reversed phase BPLC (30×75 mm ODS-A column) CH₃CN in H₂O (10-90%, 0.1% TFA). Concentration under reduced pressure gave the title compound (108 mg, 49%) as a white solid:

MS (+ve ion electrospray) m/z 497 (MH+)

Example 34

6-[({cis-3-Fluoro-1-[(R)-2-hydroxy-2-(6-methoxy-[1,5]naphthyridin-4-yl)-ethyl]piperidin-4-ylamino}methyl)-4H-benzo[1,4]thiazin-3-one Faster Running Diastereoisomer A diastereomeric mixture of 6-[({((3R,4S)-3-fluoro-1-[(R)-2-hydroxy-2-(6-methoxy-[1,5]naphthyridin-4-yl)-ethyl]piperidin-4-ylamino}methyl)-4H-benzo[1,4]thiazin-3-one and 6-[({(3S,4R)-3-fluoro-1-[(R)-2-hydroxy-2-(6-methoxy-[1,5]naphthyridin-4-yl)-ethyl]piperidin-4-ylamino}methyl)-4H-benzo[1,4]thiazin-3-one (Example 33) (230 mg, 0.46 mmole) was purified by chiral HPLC using a Chiralcel-OD column (10 uM, 20 mm×250 mm), 30% EtOH (0.1% diethylamine) in hexanes at 17.5 mL/in at 10 mg/injection×23 injections. The fractions containing the faster-running diastereoisomer ($R_t$ 12.88 min.) were collected to give the title compound

Example 35

6-[({cis-3-Fluoro-1-[(R)-2-hydroxy-2-(6-methoxy-[1,5]naphthyridin-4-yl)-ethyl]piperidin-4-ylamino}methyl)-4H-benzo[1,4]thiazin-3-one Slower-Running Diastereoisomer The fractions containing the slower-running diastereoisomer of Example 34 ($R_t$ 14.99 min.) were collected to give the title compound

Examples 36 and 37

6-({2S,4S)-1-[(R)-2-hydroxy-2-(6-methoxy-[1,5]naphthyridin-4-yl)ethyl]-2-(trifluoromethyl)piperidin-4-ylamino}methyl)-4H-pyrido[1,4]thiazin-3-one and 6-({2S,4R)-1-[(R)-2-hydroxy-2-(6-methoxy-[1,5]naphthyridin-4-yl)ethyl]-2-(trifluoromethyl)piperidin-4-ylamino}methyl)-4H-pyrido[1,4]thiazin-3-one

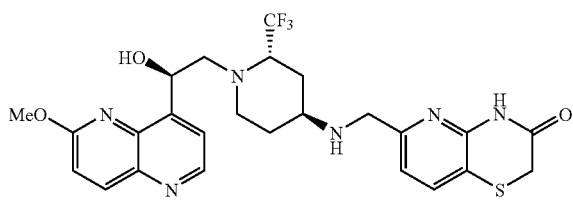

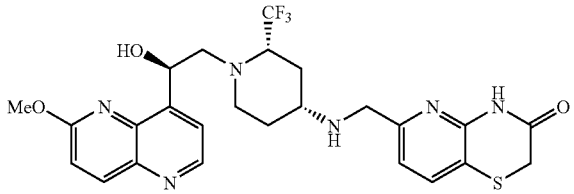

(a) (R)-Phenylethyl-(2,2,2-trifluoroethylidene)amine

To solution of (trifluoromethyl)acetaldehyde ethyl hemiacetal (100 mmole, 15.0 g) in toluene was added (R)-(+)-α-methylbenzylamine (75 mmole, 9.0 g) and a catalytic amount of p-toluenesulfonic acid. The solution was heated at reflux under a Dean-Stark apparatus. After 3 hr, the reaction flask was fitted with a short-path condenser and the reaction contents were fractionally distilled to give the title compound (11.7 g, 69%) as a colorless oil: ¹H NMR (400 MHz, CDCl₃) δ 7.57 (br s, 1H), 7.25-7.40 (m, 5H), 4.66 (m, 1), 1.57 (d, J=6.7 Hz, 3H).

(b) 1-[1-(R)-Phenylethyl]-2-(S)-(trifluoromethyl)-2,3-dihydro-1H-pyridin-4-one and 1-[1-(R)-phenylethyl]-2-(R)-(trifluoromethyl)-2,3-dihydro-1H-pyridin-4-one To a suspension of ZnCl₂ (3.64 g, 26.7 mmole) in acetonitrile at −50° C. was added (R)-phenylethyl-(2,2,2-trifluoroethylidene) amine (36/37a) (5.4 g, 24.3 mmole). After 5 min, 1-methoxy-3-(trimethylsilyloxy)-1,3-butadiene (Danishefsky's diene, 5.0 g, 29.0 mmole) was added and stirring was continued for 14 hr at −50° C. The reaction was warmed to RT, poured onto H₂O and extracted with CH₂Cl₂. The combined organic fractions were washed with 1 M HCl, dried over Na₂SO₄ and concentrated. Purification by flash chromatography on silica gel (1:1 hexanes/EtOAc) afforded the title compounds as separable diastereomers. Faster running diastereomer (2.2 g, 34%): ¹H NMR (400 MHz, CDCl₃) 7.35-7.50 (m, 6H), 5.12 (d, J=8.0 Hz, 1H), 4.57 (m, 1H), 3.81 (m, 1H), 2.75 (m, 1H), 2.56 (d, J=17.5 Hz, 1H), 1.67 (d, J=6.9 Hz, 3H); LCMS (ES) m/e 270 (M+H)⁺. Slower running diastereomer and (0.4 g, 6%): ¹H NMR (400 MHz, CDCl₃) δ 7.35-7.45 (m, 5H), 6.83 (d, J=6.9 Hz, 1H), 4.95 (d, J=7.9 Hz, 1H), 4.65 (m, 1H), 4.10 (m, 1H), 2.82 (m, 1H), 2.64 (d, J=17.6 Hz, 1H), 1.67 (d, J=6.9 Hz, 3H). LCMS (ES) m/e 270 (M+H)⁺.

(c) 1-[(R)-1-Phenylethyl]-2-(S)-(trifluoromethyl)piperidin-4-ol

To a solution of 1-[1-(R)-1-phenylethyl]-2-(S)-(trifluoromethyl)-2,3-dihydro-1H-pyridin-4-one (36/37b) (1.4 g, 5.2 mmole, faster running diastereomer from above procedure) at −78° C. in THF was added L-Selectride® (lithium tri-sec-butylborohydride) (10.4 mL, 1M in THF) dropwise. After 3 hr, the reaction was quenched with H₂O and EtOAc was added. The organic layer was separated, washed sequentially with saturated aqueous NaHCO₃ and brine, then dried over Na₂SO₄. Purification by flash chromatography on silica gel (1:1 hexanes/EtOAc) afforded the title compound (1.26 g, 89%) as a colorless oil: LCMS (ES) m/e 274 (M+H)⁺.

(d) 1-[(R)-1-Phenylethyl]-2-(S)-(trifluoromethyl) piperidin-4-one

To a solution of 1-[1-(R)-1-phenylethyl]-2-(S)-(trifluoromethyl)-2,3-dihydro-1H-pyridin-4-ol (36/37c) (1.26 g, 4.63 mmole) at RT in $CH_2Cl_2$ was added PDC (2.61 g, 6.95 mmole). After 12 hr, the reaction was filtered through celite® and the filter pad was washed with EtOAc. The filtrate was concentrated in vacuo and the residue was purified by flash chromatography on silica gel (1:1 hexanes/EtOAc) to afford the title compound (0.89 g, 71%) as a light yellow oil: LCMS (ES) m/e 272 (M+H)$^+$.

(e) 1-[1-(R)-Phenylethyl]-((2S,4S)-2-(trifluoromethyl)piperidin-4-yl)carbamic acid tert-butyl ester and 1-[1-(R)-phenylethyl]-((2S,4R)-2-(trifluoromethyl)piperidin-4-yl)carbamic acid tert-butyl ester To a solution of methoxy]amine hydrochloride (0.34 g, 4.92 mmole) and sodium acetate (2.2 eq.) in ethanol was added 1-[(R)-1-phenylethyl]-2-(S)-(trifluoromethyl)piperidin-4-one (36/37d) (0.89 g, 3.28 mmole). After 12 hr at RT, the solution was concentrated and the residue was partitioned between EtOAc and 10% aqueous $NaHCO_3$ solution. The layers were separated and the organic phase was dried over $Na_2SO_4$, then was concentrated to an oil. This oil (the O-methyloxime) was dissolved in EtOH (15 mL) and 2N NaOH (15 mL). Al—Ni alloy (1.40 g, 16.4 mmole) was added to the solution and the reaction was stirred at RT for 3 hr. The resulting slurry was filtered through a glass frit and the filtrate was concentrated in vacuo. The residue was dissolved in $CH_2Cl_2$ and the solution was dried over $Na_2SO_4$ then was concentrated in vacuo. The resulting residue (the crude amine) was dissolved in dry TMF at RT, and di-tert-butyl dicarbonate (0.79 g, 3.6 mmole) was added. After 6 hr, the reaction solution was concentrated and the remaining residue was purified by flash chromatography on silica gel (4:1 hexanes/EtOAc) to afford the title compounds (0.83 g, 68%) as a mixture of diastereomers: LCMS (ES) m/e 373 (M+H)$^+$.

(f) ((2S,4S)-2-(trifluoromethyl)piperidin-4-yl)carbamic Acid tert-Butyl Ester and ((2S,4R)-2-(trifluoromethyl)piperidin-4-yl)carbamic acid tert-butyl ester A mixture of 1-[1-(R)-phenylethyl]-((2S,4S)-2-(trifluoromethyl)piperidin-4-yl)carbamic acid tert-butyl ester and 1-[1-(R)-phenylethyl]-((2S,4R)-2-(trifluoromethyl)piperidin-4-yl)carbamic acid tert-butyl ester (36/37e) (0.83 g, 2.23 mmole), from step (e), was dissolved in ethanol, and a catalytic amount of 20% Pd(OH)$_2$ was added. The reaction was stirred vigorously under a balloon of $H_2$. After 20 hr, the mixture was filtered through celite®, and the filter pad was washed with ethanol. The filtrate was concentrated in vacuo to give the title compounds (0.57 g, 95%) as a colorless oil. LCMS (ES) m/e 269 (M+H)$^+$.

(g) {(2S,4S)-[(R)-hydroxy-(6-methoxy-[1,5]naphthyridin-4-yl)ethyl]-2-(trifluoromethyl)piperidin-4-yl}carbamic acid tert-butyl ester and {(2S,4R)-[(R)-hydroxy-(6-methoxy-[1,5]naphthyridin-4-yl)ethyl]-2-(trifluoromethyl)piperidin-4-yl}carbamic acid tert-butyl ester To a solution of 6-methoxy-4(R)-oxiranyl-[1,5]naphthyridine (1i) (0.47 g, 2.34 mmole) in DMF (3 mL) was added a mixture of ((2S,4S)-2-(trifluoromethyl)piperidin-4-yl) carbamic acid tert-butyl ester and ((2S,4R)-2-(trifluoromethyl) piperidin-4-yl) carbamic acid tert-butyl ester (36/37f) (0.57 g, 2.13 mmole). The solution was heated at 100° C. for 72 hr and then cooled to RT and concentrated in vacuo. Purification by flash chromatography on silica gel (9:1 $CHCl_3$/MeOH) afforded the title compounds (0.70 g, 70%) as a mixture of diastereomers: LCMS (ES) m/e 471 (M+H)$^+$.

(h) (R)-2-((2S,4S)-4-amino-2-(trifluoromethyl)piperidin-1-yl)-1-(6-methoxy-[1,5]naphthyridin-4-yl) ethanol and (R)-2-((2S,4R)-4-amino-2-(trifluoromethyl)piperidin-1-yl)-1-(6-methoxy-[1,5] naphthyridin-4-yl)ethanol A mixture of diastereomers {(2S,4S)-[(R)-hydroxy-(6-methoxy-[1,5]naphthyridin-4-yl)ethyl]-2-(trifluoromethyl) piperidin-4-yl}carbamic acid tert-butyl ester and {(2S,4R)-[(R)-hydroxy-(6-methoxy-[1,5]naphthyridin-4-yl)ethyl]-2-(trifluoromethyl)piperidin-4-yl}carbamic acid tert-butyl ester (36/37g) was dissolved in 1:1 $CH_2Cl_2$/TFA. After 2 hr, the solution was concentrated to dryness in vacuo and the residue was dissolved in $H_2O$. The solution was made basic with aqueous NaOH then was concentrated to dryness in vacuo. The residue was dried under high vacuum, and the resulting solid was extracted with 9:1 $CH_2Cl_2$/MeOH. The combined extracts were concentrated and dried under high vacuum to give the title compounds: LCMS (ES) m/e 371 (M+H)$^+$.

(i) 6-({2S,4S)-1-[(R)-2-Hydroxy-2-(6-methoxy-[1,5] naphthyridin-4-yl)ethyl ]-2-(trifluoromethyl)piperidin-4-ylamino}methyl)-4H-pyrido[1,4]thiazin-3-one and 6-({2S,4R)-1-[(R)-2-Hydroxy-2-(6-methoxy-[1, 5]naphthyridin-4-yl)ethyl]-2-(trifluoromethyl)piperidin-4-ylaniino}methyl)-4H-pyrido[1,4]thiazin-3-one To a solution of diastereomers (R)-2-((2S,4S)-4-amino-2-(trifluoromethyl)piperidin-1-yl)-1-(6-methoxy-[1,5]naphthyridin-4-yl)ethanol and (R)-2-((2S,4R)-4-amino-2-(trifluoromethyl)piperidin-1-yl)-1-(6-methoxy-[1,5] naphthyridin-4-yl)ethanol (36/37h) (0.55 g, 1.49 mmole) in $CH_2Cl_2$ (15 mL) and EtOH (15 mL) was added $Na_2SO_4$ (100 mg) and 3-oxo-3,4-dihydro-2H-pyrido[3,2-b][1,4]thiazine-6-carboxaldehyde (6g) (0.32 g, 1.64 mmole). The mixture was stirred at RT for 12 hr, then $NaBH_4$ (57 mg, 1.5 mmole) was added. The reaction was allowed to stir overnight then was concentrated, and the residue was dissolved in 6 N HCl. The resulting solution was neutralized with 6 N NaOH and extracted with EtOAc. The combined organic layers were dried over $Na_2SO_4$ and concentrated in vacuo. The crude product was purified by reverse phase chromatography on HPLC to afford the title compounds as separable and distinct diastereomers. The major and more polar diastereomer (400 mg, 42%): $^1$H NMR (400 MHz, $d_4$-MeOH) 8.84 (d, J=4.5 Hz, 1H), 8.30 (d, J=9.0 Hz, 1H), 8.03 (d, J=4.5 Hz, 1H), 7.81 (d, J=7.7 Hz, 1H), 7.36 (d, J=8.9 Hz, 1H), 7.09 (d, J=7.8 Hz, 1H), 5.95 (m, 1H), 4.34 (m, 1H), 4.10 (s, 3H), 3.70 (m, 1H), 3.65 (s, 2H), 3.55 (s, 2H), 3.18 (m, 1H), 3.02 (m, 1H), 2.64 (m, 1H), 2.31 (m, 1H), 2.18 (m, 1H), 1.69 (m, 2H); LCMS (ES) m/e 549 (M+H)$^+$. The minor and less polar diastereomer (240 mg, 28%): $^1$H NMR (400 MHz, $d_4$-MeOH) δ 8.80 (d, J=4.5 Hz, 111), 8.28 (d, J=9.0 Hz, 1H), 8.01 (d, J=4.5 Hz, 1H), 7.77 (d, J=7.7 Hz, 1H), 7.36 (d, J=8.9 Hz, 1H), 7.08 (d, J=7.8 Hz, 1H), 5.90 (m, 1H), 4.30 (m, 1H), 4.10 (s, 3H), 3.79 (m, 1H), 3.65 (s, 2H), 3.57 (s, 2H), 3.45 (m, 1H), 3.10 (m, 2H), 3.01 (m, 1H), 2.29 (m, 1H), 2.01 (m, 1H), 1.75 (m, 1H), 1.48 (m, 1H); LCMS (ES) m/e 549 (M+H)$^+$.

The other slower running diastereomer described in step (b) can be processed similarly (steps (c) and (i)) to afford the following products:

6-({2R,4S)-1-[(R)-2-hydroxy-2-(6-methoxy-[1,5]naphthyridin-4-yl)ethyl]-2-(trifluoromethyl)piperidin-4-ylamino}methyl)-4H-benzo[1,4]thiazin-3-one 6-({2R,4R)-1-[(R)-2-hydroxy-2-(6-methoxy-[1,5]naphthyridin-4-yl)ethyl]-2-(trifluoromethyl)piperidin-4-ylamino}methyl)-4H-benzo[1,4]thiazin-3-one.

Note: The configurations at positions 2 and 4 of the piperidine were not rigorously determined, and were assigned randomly.

The following Examples were prepared by analogous methods:

| Example | salt B p= hydrochloride | A | $R^1$ | $R^{1a}$ | X | $R^5$ |
|---|---|---|---|---|---|---|
| 38 enantiomer 2[a] | B | CH | MeO | F | OH | 6-[4H-pyrido[3,2-b][1,4]thiazin-3-one] |
| 39 Enantiomer 1[b] | B | CH | MeO | F | OH | 6-[7-chloro-4H-pyrido[3,2-b][1,4]oxazin-3-one] |
| 40 Enantiomer 2[a] | B | CH | MeO | F | OH | 6-[4H-pyrido[3,2-b][1,4]oxazin-3-one]] |
| 41 Enantiomer 2[a,d] | B | CH | MeO | H | OH | 7-[2,3-dihydro-[1,4]dioxino[2,3-c]pyridine] |
| 42 Enantiomer 1[b,d] | B | CH | MeO | H | OH | 7-[2,3-dihydro-[1,4]dioxino[2,3-c]pyridine] |
| 43 Enantiomer 2[a,e] | B | N | MeO | H | H | 6-[4H-pyrido[3,2-b][1,4]thiazin-3-one] |

-continued

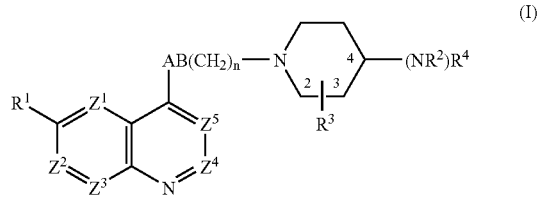

| Example | salt B p= hydrochloride | A | R¹ | R¹ᵃ | X | R⁵ |
|---|---|---|---|---|---|---|
| 44 Racemic[c,f] | B | CH | F | F | H | 6-[4H-pyrido[3,2-b][1,4]oxazin-3-one]] |

[a]Prepared from cis-4-benzylamino-1-tert-butoxycarbonyl-3-fluoropiperidine (6a) slower running Enantiomer 2.
[b]Preparfed from cis-4-benzylamino-1-tert-butoxycarbonyl-3-fluoropiperidine (6a) faster running Enantiomer 1
[c]Prepared from (3R, 4S) and (3S, 4R)-4-benzylamino-1-tert-butoxycarbonyl-3-fluoropiperidine (5a)
[d]Prepared from 2,3-dihydro-[1,4]dioxino[2,3-c]pyridine-7-carboxaldehyde. 5-Benzyloxy-2-hydroxymethyl-4-pyrone (prepared from Kojic acid by the method of D. Erol, J. Med. Chem., 1994, 29, 893) was treated with concentrated aqueous ammonia and ethanol with heating to give the corresponding 5-benzyloxy-2-hydroxymethyl-1H-pyridin-4-one. This was dehydrogenated, removing the benzyl protecting group, and the crude product was heated with 1,2-dibromoethane and potassium carbonate in DMF andheated overnight to produce, after chromatography, (2,3-dihydro-[1,4]dioxino[2,3-c]pyridin-7-yl)-methanol as a white solid. This was cleanly oxidised with manganese (II) oxide in dichloromethane to give 2,3-dihydro-[1,4]dioxino[2,3-c]pyridine-7-carboxaldehyde as a white solid.
[e]This was prepared analogously to Example 29 example 3-fluoro-1-[2-(6-methoxy-[1,5]naphthyridin-4-yl)-ethyl]-piperidin-4-ylamine Enantiomer 2 was used instead of (29b).
[f]This was prepared analogously to Example 32 except the carboxaldehyde (10e) was used instead of carboxaldehyde (6 g).

Biological Activity

The MIC (μg/ml) of test compounds against various organisms may be determined:
S. epidermidis CL7, S. aureus WCUH29, S. pneumoniae 1629, S. pyogenes CN10, H. influenzae ATCC49247, E. faecalis 2, E. faecium 8, M. catarrhalis Ravisio, E. coli 7623.

Compounds of Examples 5, 6, 7, 9-11, 15, 20-22, 24-29, 33, 34, 38-40, 43 have MIC's ≦2 μg/ml versus all of these organisms.

Compounds of Examples 8, 12-14, 16-19, 23, 30-32, 36, 41, 42 and 44 have MIC's ≦16 μg/ml versus all of these organisms.

Compound of Example 37 has MIC's ≦16 μg/ml versus some of these organisms.

The invention claimed is:

1. A compound of formula (I) or a pharmaceutically acceptable salt and/or N-oxide thereof:

(I)

wherein:
one of $Z^1$, $Z^2$, $Z^3$, $Z^4$ and $Z^5$ is N, one is $CR^{1a}$ and the remainder are CH, or one of $Z^1$, $Z^2$, $Z^3$, $Z^4$ and $Z^5$ is $CR^{1a}$ and the remainder are CH;
$R^1$ and $R^{1a}$ are independently hydrogen; hydroxy; $(C_{1-6})$alkoxy optionally substituted by $(C_{1-6})$alkoxy, amino, piperidyl, guanidino or amidino any of which is optionally N-substituted by one or two $(C_{1-6})$alkyl, acyl or $(C_{1-6})$alkylsulphonyl groups, $CONH_2$, hydroxy, $(C_{1-6})$alkylthio, heterocyclylthio, heterocyclyloxy, arylthio, aryloxy, acylthio, acyloxy or $(C_{1-6})$alkylsulphonyloxy; $(C_{1-6})$alkoxy-substituted$(C_{1-6})$alkyl; halogen; $(C_{1-6})$alkyl; $(C_{1-6})$alkylthio; trifluoromethyl; trifluoromethoxy; nitro; azido; acyl; acyloxy; acylthio; $(C_{1-6})$alkylsulphonyl; $(C_{1-6})$alkylsulphoxide; arylsulphonyl; arylsulphoxide or an amino, piperidyl, guanidino or amidino group optionally N-substituted by one or two $(C_{1-6})$alkyl, acyl or $(C_{1-6})$alkylsulphonyl groups;
or when $Z^5$ is $CR^{1a}$, $R^{1a}$ may instead be cyano, hydroxymethyl or carboxy;
or $R^1$ and $R^{1a}$ on adjacent positions may together form ethylenedioxy;
provided that when none of $Z^1$, $Z^2$, $Z^3$, $Z^4$ and $Z^5$ is N, then $R^1$ is not hydrogen;
$R^2$ is hydrogen, or $(C_{1-4})$alkyl or $(C_{2-4})$alkenyl optionally substituted with 1 to 3 groups selected from:
amino optionally substituted by one or two $(C_{1-4})$alkyl groups; carboxy; $(C_{1-4})$alkoxycarbonyl; $(C_{1-4})$alkylcarbonyl; $(C_{2-4})$alkenyloxycarbonyl; $(C_{2-4})$alkenylcarbonyl; aminocarbonyl wherein the amino group is optionally substituted by hydroxy, $(C_{1-4})$alkyl, hydroxy$(C_{1-4})$alkyl, aminocarbonyl$(C_{1-4})$alkyl, $(C_{2-4})$alkenyl, $(C_{1-4})$alkylsulphonyl, trifluoromethylsulphonyl, $(C_{2-4})$alkenylsulphonyl, $(C_{1-4})$alkoxycarbonyl, $(C_{1-4})$alkylcarbonyl, $(C_{2-4})$alkenyloxycarbonyl or $(C_{2-4})$alkenylcarbonyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; 5-oxo-1,2,4-oxadiazol-3-yl;

halogen; $(C_{1-4})$alkylthio; trifluoromethyl; hydroxy optionally substituted by $(C_{1-4})$alkyl, $(C_{2-4})$alkenyl, $(C_{1-4})$alkoxycarbonyl, $(C_{1-4})$alkylcarbonyl, $(C_{2-4})$alkenyloxycarbonyl, or $(C_{2-4})$alkenylcarbonyl; oxo; $(C_{1-4})$alkylsulphonyl; $(C_{2-4})$alkenylsulphonyl; and $(C_{1-4})$aminosulphonyl wherein the amino group is optionally substituted by $(C_{1-4})$alkyl or $(C_{2-4})$alkenyl;

$R^3$ is in the 2-, 3- or 4-position and is trifluoromethyl or is in the 2-position and is oxo; or $R^3$ is in the 3-position and is fluorine or amino wherein the amino group is optionally substituted by: hydroxy; $(C_{1-6})$alkylsulphonyl; trifluoromethylsulphonyl; $(C_{2-6})$alkenylsulphonyl; $(C_{1-6})$alkylcarbonyl; $(C_{2-6})$alkenylcarbonyl; $(C_{1-6})$alkoxycarbonyl; $(C_{2-6})$alkenyloxycarbonyl; $(C_{1-6})$alkyl; or $(C_{2-6})$alkenyl; wherein a $(C_{1-6})$alkyl or $(C_{2-6})$alkenyl moiety may be optionally substituted with up to 2 groups $R^{12}$ independently selected from:

halogen; $(C_{1-6})$alkylthio; trifluoromethyl; cyano; carboxy; tetrazolyl; 2-oxo-oxazolidinyl; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; 5-oxo-1,2,4-oxadiazol-3-yl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy optionally substituted by $(C_{1-6})$alkyl, $(C_{2-6})$alkenyl, $(C_{1-6})$alkylcarbonyl, $(C_{2-6})$alkenylcarbonyl or aminocarbonyl wherein the amino group is optionally substituted by $(C_{1-6})$alkyl, or $(C_{2-6})$alkenyl; and amino optionally mono- or disubstituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$alkenylsulphonyl or aminocarbonyl wherein the amino group is optionally substituted by $(C_{1-6})$alkyl or $(C_{2-6})$alkenyl;

in addition when $R^3$ is disubstituted with a hydroxy or amino containing substituent and a carboxy containing substituent these may together form a cyclic ester or amide linkage, respectively;

$R^4$ is a group —U—$R^5$ where

U is selected from CO, $SO_2$ and $CH_2$ and $R^5$ is an optionally substituted bicyclic carbocyclic or heterocyclic ring system (A):

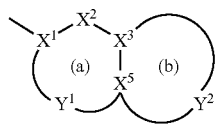

(A)

containing up to four heteroatoms in each ring in which ring (a) is aromatic and ring (b) is non-aromatic;

$X^1$ is C or N;

$X^2$ is N, $NR^{13}$, O, $S(O)_x$, CO or $CR^{14}$;

$X^3$ and $X^5$ are independently N or C;

$Y^1$ is a 0 to 4 atom linker group each atom of which is independently selected from N, $NR^{13}$, O, $S(O)_x$, CO and $CR^{14}$;

$Y^2$ is a 2 to 6 atom linker group, each atom of $Y^2$ being independently selected from N, $NR^{13}$, O, $S(O)_x$, CO, $CR^{14}$ and $CR^{14}R^{15}$;

each of $R^{14}$ and $R^{15}$ is independently selected from: H; $(C_{1-4})$alkylthio; halo; carboxy$(C_{1-4})$alkyl; halo$(C_{1-4})$alkoxy; halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$alkoxycarbonyl$(C_{1-4})$alkyl; hydroxy; hydroxy$(C_{1-4})$alkyl; mercapto$(C_{1-4})$alkyl; $(C_{1-4})$alkoxy; trifluoromethoxy; nitro; cyano; carboxy; amino or aminocarbonyl optionally substituted as for corresponding substituents in $R^3$; $(C_{1-4})$alkylsulphonyl; $(C_{2-4})$alkenylsulphonyl; aminosulphonyl wherein the amino group is optionally mono- or di-substituted by $(C_{1-4})$alkyl or $(C_{2-4})$alkenyl; aryl; aryl$(C_{1-4})$alkyl; and aryl$(C_{1-4})$alkoxy;

each $R^{13}$ is independently H; trifluoromethyl; $(C_{1-4})$alkyl optionally substituted by hydroxy, $(C_{1-6})$alkoxy, $(C_{1-6})$alkylthio, halo or trifluoromethyl; $(C_{2-4})$alkenyl; aryl; aryl $(C_{1-4})$alkyl; arylcarbonyl; heteroarylcarbonyl; $(C_{1-4})$alkoxycarbonyl; $(C_{1-4})$alkylcarbonyl; formyl; $(C_{1-6})$alkylsulphonyl; or aminocarbonyl wherein the amino group is optionally substituted by $(C_{1-4})$alkoxycarbonyl, $(C_{1-4})$alkylcarbonyl, $(C_{2-4})$alkenyloxycarbonyl, $(C_{2-4})$alkenylcarbonyl, $(C_{1-4})$alkyl or $(C_{2-4})$alkenyl and optionally further substituted by $(C_{1-4})$alkyl or $(C_{2-4})$alkenyl;

each x is independently 0, 1 or 2 n is 0 and AB is $NR^{11}CO$, $CO—CR^8R^9$, $CR^6R^7—CO$, $NHR^{11}SO_2$, $CR^6R^7—SO_2$ or $CR^6R^7—CR^8R^9$, provided that $R^8$ and $R^9$ are not optionally substituted hydroxy or amino and $R^6$ and $R^8$ do not represent a bond:

or n is 1 and AB is $NR^{11}CO$, $CO—CR^8R^9$, $CR^6R^7—CO$, $NR^{11}SO_2$, $CONR^{11}$, $CR^6R^7—CR^8R^9$, $O—CR^8R^9$ or $NR^{11}—CR^8R^9$;

each of $R^6$, $R^7$, $R^8$ and $R^9$ is independently selected from: hydrogen; $(C_{1-6})$alkoxy; $(C_{1-6})$alkylthio; halo; trifluoromethyl; azido; $(C_{1-6})$alkyl; $(C_{2-6})$alkenyl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy, amino or aminocarbonyl optionally substituted as for corresponding substituents in $R^3$; $(C_{1-6})$alkylsulphonyl; $(C_{2-6})$alkenylsulphonyl; and aminosulphonyl wherein the amino group is optionally substituted by $(C_{1-6})$alkyl or $(C_{2-6})$alkenyl;

or when n=1 $R^6$ and $R^8$ together represent a bond and $R^7$ and $R^9$ are as above defined;

or $R^6$ and $R^7$ or $R^8$ and $R^9$ together represent oxo;

$R^{10}$ is selected from $(C_{1-4})$alkyl; $(C_{2-4})$alkenyl and aryl any of which may be optionally substituted by a group $R^{12}$ as defined above; carboxy; aminocarbonyl wherein the amino group is optionally substituted by hydroxy, $(C_{1-6})$alkyl, $(C_{2-6})$alkenyl, $(C_{1-6})$alkylsulphonyl, trifluoromethylsulphonyl, $(C_{2-6})$alkenylsulphonyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl or $(C_{2-6})$alkenyl; and $R^{11}$ is hydrogen; trifluoromethyl; $(C_{1-6})$alkyl; $(C_{2-6})$alkenyl; $(C_{1-6})$alkoxycarbonyl; $(C_{1-6})$alkylcarbonyl; or aminocarbonyl wherein the amino group is optionally substituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl or $(C_{2-6})$alkenyl and optionally further substituted by $(C_{1-6})$alkyl or $(C_{2-6})$alkenyl;

or where one of $R^3$ and $R^6$, $R^7$, $R^8$ or $R^9$ contains a carboxy group and the other contains a hydroxy or amino group they may together form a cyclic ester or amide linkage.

2. A compound according to claim 1 wherein $Z^5$ is CH, C—Cl or N, $Z^3$ is CH or CF and $Z^1$, $Z^2$ and $Z^4$ are each CH, or $Z^1$ is N, $Z^3$ is CH and $Z^2$ and $Z^4$ are each CH and $Z^5$ is CH or C—Cl.

3. A compound according to claim 1 wherein $R^1$ is methoxy and $R^{1a}$ is H or when $Z^3$ is $CR^{1a}$ it may be C—F or when $Z^5$ is $CR^{1a}$ it may be C—F or C—Cl.

4. A compound according to claim 1 wherein $R^2$ is hydrogen, carboxymethyl, hydroxyethyl, aminocarbonylmethyl, ethoxycarbonylmethyl, ethoxycarbonylallyl or carboxyallyl.

5. A compound according to claim 1 wherein $R^3$ is $CF_3$, fluoro, oxo or amino unsubstituted or substituted by $(C_{1-6})$alkyl or $(C_{2-6})$alkenyl.

6. A compound according to claim 1 wherein n is 0 and either A is $CH_2$ or CHOH and B is $CH_2$ or A is NH and B is CO.

7. A compound according to claim 1 wherein —U— is —$CH_2$—.

8. A compound according to claim 1 wherein in the heterocyclic ring (A) ring (a) is selected from optionally substituted benzo and pyrido and $Y^2$ has 3-5 atoms including a heteroatom bonded to $X^5$ selected from $NR^{13}$, O and S, where $R^{13}$ is other than hydrogen, and NHCO bonded via N to $X^3$, or O or NH bonded to $X^3$.

9. A compound according to claim 1 wherein $R^5$ is selected from:
- 4H-benzo[1,4]oxazin-3-one-6-yl;
- 4H-benzo[1,4]thiazin-3-one-6-yl;
- 2,3-dihydro-[1,4]dioxino[2,3-c]pyridin-7-yl;
- 3-oxo-3,4-dihydro-2H-pyrido[3,2-b][1,4]thiazin-6-yl;
- 3-oxo-3,4-dihydro-2H-pyrido[3,2-b][1,4]oxazin-6-yl;
- 7-chloro-3-oxo-3,4-dihydro-2H-pyrido[3,2-b][1,4]oxazin-6-yl; and
- 7-chloro-3-oxo-3,4-dihydro-2H-pyrido[3,2-b][1,4]thiazin-6-yl.

10. A compound according to claim 1 selected from:
- 6-({2S,4S)-1-[(R)-2-Hydroxy-2-(6-methoxy-[1,5]naphthyridin-4-yl)ethyl]-2-(trifluoromethyl)piperidin-4-ylamino}methyl)-4H-benzo[1,4]thiazin-3-one;
- 6-({(3R,4S)-1-[(R)-2-Hydroxy-2-(6-methoxy-[1,5]naphthyridin-4-yl)ethyl]-3-(trifluoromethyl)piperidin-4-ylamino}methyl)-4H-benzo[1,4]thiazin-3-one;
- 6-({1-[(R)-2-Hydroxy-2-(6-methoxy-[1,5]naphthyridin-4-yl)ethyl]-4-(trifluoromethyl)piperidin-4-ylamino}methyl)-4H-benzo[1,4]thiazin-3-one;
- 6-({1-[(R)-2-Hydroxy-2-(6-methoxyquinolin-4-yl)ethyl]-2-oxopiperidin-4-ylamino}methyl)-4H-benzo[1,4]thiazin-3-one;
- 6-[({(3S,4R)-3-Fluoro-1-[(R)-2-hydroxy-2-(6-methoxyquinolin-4-yl)-ethyl]piperidin-4-ylamino}methyl)-4H-benzo[1,4]thiazin-3-one and 6-[({(3R,4S)-3-fluoro-1-[(R)-2-hydroxy-2-(6-methoxyquinolin-4-yl)-ethyl]piperidin-4-ylamino}methyl)-4H-benzo[1,4]thiazin-3-one;
- 6-({cis-3-Fluoro-1-[(R)-2-hydroxy-2-(6-methoxyquinolin-4-yl)ethyl]piperidin-4-ylamino}methyl)-4H-pyrido[3,2-b][1,4]thiazin-3-one Diastereoisomer 1;
- 6-({cis-3-Fluoro-1-[(R)-2-hydroxy-2-(6-methoxyquinolin-4-yl)-ethyl]-piperidin-4-ylamino}-methyl)-4H-pyrido[3,2-b][1,4]thiazin-3-one Diastereoisomer 2;
- 7-Chloro-6-({cis 3-fluoro-1-[(R)-2-hydroxy-2-(6-methoxyquinolin-4-yl)-ethyl]piperidin-4-ylamino}methyl)-4H-pyrido[3,2-b][1,4]thiazin-3-one Diastereoisomer 1;
- 7-Chloro-6-({cis-3-Fluoro-1-[(R)-2-hydroxy-2-(6-methoxyquinolin-4-yl)-ethyl]piperidin-4-ylamino}methyl)-4H-pyrido[3,2-b][1,4]thiazin-3-one Diastereoisomer 2;
- 6-({cis-3-Fluoro-1-[(R)-2-hydroxy-2-(6-methoxyquinolin-4-yl)-ethyl]piperidin-4-ylamino}methyl)-4H-pyrido[3,2-b][1,4]oxazin-3-one Diastereoisomer 1;
- 6-({cis-3-Fluoro-1-[(R)-2-hydroxy-2-(6-methoxyquinolin-4-yl)-ethyl]piperidin-4-ylamino}methyl)-4H-pyrido[3,2-b][1,4]oxazin-3-one Diastereoisomer 2;
- 7-Chloro-6-[({(3S,4R)-3-fluoro-1-[(R)-2-hydroxy-2-(6-methoxyquinolin-4-yl)-ethyl]piperidin-4-ylamino}methyl)-4H-pyrido[3,2-b][1,4]thiazin-3-one and 7-chloro-6-[({(3R,4S)-3-fluoro-1-[(R)-2-hydroxy-2-(6-methoxyquinolin-4-yl)-ethyl]piperidin-4-ylamino}methyl)-4H-pyrido[3,2-b][1,4]thiazin-3-one;
- 7-Fluoro-6-({{(3S,4R)-3-fluoro-1-[(R)-2-hydroxy-2-(6-methoxyquinolin-4-yl) -ethyl]piperidin-4-ylamino}methyl)-4H-pyrido[3,2-b][1,4]thiazin-3-one and 7-fluoro-6-[({(3R,4S)-3-fluoro-1-[(R)-2-hydroxy-2-(6-methoxyquinolin-4-yl)-ethyl]piperidin-4-ylamino}methyl)-4H-pyrido[3,2-b][1,4]thiazin-3-one;
- 7-({(3S,4R)-3-fluoro-1-[(R)-2-hydroxy-2-(6-methoxyquinolin-4-yl)-ethyl]piperidin-4-ylamino}methyl)-1H-pyrido[2,3-b][1,4]thiazin-2-one and 7-({(3R,4S)-3-fluoro-1-[(R)-2-hydroxy-2-(6-methoxyquinolin-4-yl)-ethyl]piperidin-4-ylamino}methyl)-1H-pyrido[2,3-b][1,4]thiazin-2-one;
- 7-Chloro-6-[({(3S,4R)-3-fluoro-1-[(R)-2-hydroxy-2-(6-methoxyquinolin-4-yl)-ethyl]piperidin-4-ylamino}methyl)-4H-pyrido[3,2-b][1,4]oxazin-3-one and 7-chloro-6-[({(3R,4S)-3-fluoro-1-[(R)-2-hydroxy-2-(6-methoxyquinolin-4-yl)-ethyl]piperidin-4-ylamino}methyl)-4H-pyrido[3,2-b][1,4]oxazin-3-one;
- 6-[({(3S,4S)-3-Fluoro-1-[(R)-2-hydroxy-2-(6-methoxyquinolin-4-yl)-ethyl]piperidin-4-ylamino}methyl)-4H-pyrido[3,2-b][1,4]thiazin-3-one and 6-[({(3R,4R)-3-fluoro-1-[(R)-2-hydroxy-2-(6-methoxyquinolin-4-yl)-ethyl]piperidin-4-ylamino}methyl)-4H-pyrido[3,2-b][1,4]thiazin-3-one;
- 6-[({(3S,4S)-3-Fluoro-1-[(R)-2-hydroxy-2-(6-methoxyquinolin-4-yl)-ethyl]piperidin-4-ylamino}methyl)-4H-pyrido[3,2-b][1,4]oxazin-3-one and 6-[({(3R,4R)-3-fluoro-1-[(R)-2-hydroxy-2-(6-methoxyquinolin-4-yl)-ethyl]piperidin-4-ylamino}methyl)-4H-pyrido[3,2-b][1,4]oxazin-3-one;
- 7-Fluoro-6-[({(3S,4S)-3-fluoro-1-[(R)-2-hydroxy-2-(6-methoxyquinolin-4-yl)-ethyl]piperidin-4-ylamino}methyl)-4H-pyrido[3,2-b][1,4]thiazin-3-one and 7-Fluoro-6-[({(3R,4R)-3-fluoro-1-[(R)-2-hydroxy-2-(6-methoxyquinolin-4-yl)-ethyl]piperidin-4-ylamino}methyl)-4H-pyrido[3,2-b][1,4]thiazin-3-one;
- 6-[({(3S,4S)-3-Fluoro-1-[(R)-2-hydroxy-2-(6-methoxyquinolin-4-yl)-ethyl]piperidin-4-ylamino}methyl)-1H-pyrido[2,3-b][1,4]thiazin-3-one and 6-[({(3R,4R)-3-Fluoro-1-[(R)-2-hydroxy-2-(6-methoxyquinolin-4-yl)-ethyl]piperidin-4-ylamino}methyl)-1H-pyrido[2,3-b][1,4]thiazin-3-one;
- 6-({cis-3-Fluoro-1-[(R)-2-hydroxy-2-(6-methoxy-[1,5]naphthyridin)-ethyl]piperidin-4-ylamino}methyl)-4H-pyrido[3,2-b][1,4]oxazin-3-one Diastereoisomer 1;
- 6-({cis-3-Fluoro-1-[(R)-2-hydroxy-2-(6-methoxy-[1,5]naphthyridin)-ethyl]piperidin-4-ylamino}methyl)-4H-pyrido[3,2-b][1,4]oxazin-3-one Diastereoisomer 2;
- 6-({cis-3-Fluoro-1-[(R)-2-hydroxy-2-(6-methoxy-[1,5]naphthyridin)-ethyl]piperidin-4-ylamino}methyl)-4H-pyrido[3,2-b][1,4]thiazin-3-one Diastereoisomer 1;
- 6-({cis-3-Fluoro-1-[(R)-2-hydroxy-2-(6-methoxy-[1,5]naphthyridin)-ethyl]piperidin-4-ylamino}methyl)-4H-pyrido[3,2-b][1,4]thiazin-3-one Diastereoisomer 2;
- 7-Chloro-6-({cis-3-fluoro-1-[(R)-2-hydroxy-2-(6-methoxy-[1,5]naphthyridin)-ethyl]piperidin-4-ylamino}methyl)-4H-pyrido[3,2-b][1,4]oxazin-3-one Diastereoisomer 1;

7-Chloro-6-({cis-3-fluoro-1-[(R)-2-hydroxy-2-(6-methoxy-[1,5]naphthyridin)-ethyl]piperidin-4-ylamino}methyl)-4H-pyrido[3,2-b][1,4]oxazin-3-one Diastereoisomer 2;

6-({cis-3-Fluoro-1-[(R)-2-hydroxy-2-(8-fluoro-6-methoxy-quinolin-4-yl)-ethyl]piperidin-4-ylamino}methyl)-4H-pyrido[3,2-b][1,4]oxazin-3-one Diastereoisomer 1;

6-({cis-3-Fluoro-1-[(R)-2-hydroxy-2-(8-fluoro-6-methoxy-quinolin-4-yl)-ethyl]piperidin-4-ylamino}methyl)-4H-pyrido[3,2-b][1,4]thiazin-3-one Diastereoisomer 1;

6-({(3R,4S)-1-[2-(3-Chloro-6-methoxy-quinolin-4-yl)-ethyl]-3-fluoro-piperidin -4-ylamino}methyl)-4H-pyrido[3,2-b][1,4]thiazin-3-one and 6-({(3S,4R)-1-[2-(3-Chloro-6-methoxy-quinolin-4-yl)-ethyl]-3-fluoro-piperidin-4-ylamino}methyl)-4H-pyrido[3,2-b][1,4]thiazin-3-one;

6-({(3R,4S)-3-Fluoro-1-[2-(6-methoxy-[1,5]naphthyridin-4-yl)-ethyl]-piperidin-4-ylamino}-methyl)-4H-pyrido[3,2-b][1,4]thiazin-3-one and 6-({(3S,4R)-3-fluoro-1-[2-(6-methoxy-[1,5]naphthyl]-piperidin-4-ylamino}-methyl)-4H-pyrido[3,2-b][1,4]thiazin-3-one;

6-[({(3S,4R)-3-Fluoro-1-[(S)-2-hydroxy-2-(6-methoxyquinolin-4-yl)-ethyl]piperidin-4-ylamino}methyl)-4H-pyrido[3,2-b][1,4]thiazin-3-one and 6-[({(3R,4S)-3-fluoro -1-[(S)-2-hydroxy-2-(6-methoxyquinolin-4-yl)-ethyl]piperidin-4-ylamino}methyl)-4H-pyrido[3,2-b][1,4]thiazin-3-one;

6-({(3R,4S)-1-[2-(2,3-Dihydro-[1,4]dioxino[2,3-f]quinolin-10-yl)-ethyl ]-3-fluoro-piperidin-4-ylamino}-methyl)-4H-pyrido[3,2-b][1,4]thiazin-3-one and 6-({(3S,4R)-1-[2-(2,3-dihydro-[1,4]dioxino[2,3-f]quinolin-10-yl)-ethyl]-3-fluoro-piperidin-4-ylamino}-methyl)-4H-pyrido[3,2-b][1,4]thiazin-3-one;

6-({(3R,4S)-1-[2-(6,8-Difluoro-quinolin-4-yl)-ethyl]-3-fluoro-piperidin-4-ylamino}-methyl)-4H-pyrido[3,2-b][1,4]thiazin-3-one and 6-({(3S,4R)-1-[2-(6,8-difluoro-quinolin-4-yl)-ethyl]-3-fluoro-piperidin-4-ylamino}-methyl)-4H-pyrido[3,2-b][1,4]thiazin-3-one;

6-[({(3S,4R)-3-Fluoro-1-[(R)-2-hydroxy-2-(6-methoxy-[1,5]naphthyridin-4-yl)-ethyl]piperidin-4-ylamino}methyl)-4H-benzo[1,4]thiazin-3-one and 6-[({(3R,4S)-3-Fluoro-1-[(R)-2-hydroxy-2-(6-methoxy-[1,5]naphthyridin-4-yl)-ethyl]piperidin-4-ylamino}methyl)-4H-benzo[1,4]thiazin-3-one;

6-[({cis-3-Fluoro-1-[(R)-2-hydroxy-2-(6-methoxy-[1,5]naphthyridin-4-yl)-ethyl]piperidin-4-ylamino}methyl)-4H-benzo[1,4]thiazin-3-one Faster running Diastereoisomer;

6-[({(cis-3-Fluoro-1-[(R)-2-hydroxy-2-(6-methoxy-[1,5]naphthyridin-4-yl)-ethyl]piperidin-4-ylamino}methyl)-4H-benzo[1,4]thiazin-3-one Slower running Diastereoisomer;

6-({2S,4S)-1-[(R)-2-hydroxy-2-(6-methoxy-[1,5]naphthyridin-4-yl)ethyl]-2-(trifluoromethyl)piperidin-4-ylamino}methyl)-4H-pyrido[1,4]thiazin-3-one;

6-({2S,4R)-1-[(R)-2-hydroxy-2-(6-methoxy-[1,5]naphthyridin-4-yl)ethyl]-2-(trifluoromethyl)piperidin-4-ylamino}methyl)-4H-pyrido[1,4]thiazin-3-one;

and the following tabulated compounds of formula (X):

| Isomeric form | A | R¹ | R¹ᵃ | X | R⁵ |
|---|---|---|---|---|---|
| Enantiomer 2 | CH | MeO | F | OH | 6-[4H-pyrido[3,2-b][1,4]thiazin-3-one] |
| Enantiomer 1 | CH | MeO | F | OH | 6-[7-chloro-4H-pyrido[3,2-b][1,4]oxazin-3-one] |
| Enantiomer 2 | CH | MeO | F | OH | 6-[4H-pyrido[3,2-b][1,4]oxazin-3-one]] |
| Enantiomer 2 | CH | MeO | H | OH | 7-[2,3-dihydro-[1,4]dioxino[2,3-c]pyridine] |
| Enantiomer 1 | CH | MeO | H | OH | 7-[2,3-dihydro-[1,4]dioxino[2,3-c]pyridine] |
| Enantiomer 2 | N | MeO | H | H | 6-[4H-pyrido[3,2-b][1,4]thiazin-3-one] |
| Racemic | CH | F | F | H | 6-[4H-pyrido[3,2-b][1,4]oxazin-3-one]] | or a pharmaceutically acceptable salt and/or N-oxide thereof.

11. A compound according to claim 1 wherein $R^3$ is fluoro.

12. A method of treatment of bacterial infections in mammals, which method comprises the administration to a mammal in need of such treatment an effective amount of a compound according to claim 1.

13. A pharmaceutical composition comprising a compound according to claim 1, and a pharmaceutically acceptable carrier.

14. A process for preparing a compound of formula (I) according to claim 1, or a pharmaceutically acceptable salt and/or N-oxide thereof, which process comprises reacting a compound of formula (IV) with a compound of formula (V):

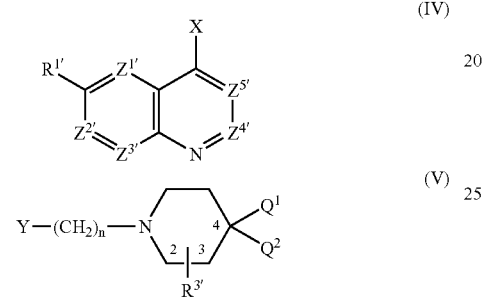

(IV)

(V)

wherein n is as defined in formula (I); $Z^{1'}$, $Z^{2'}$, $Z^{3'}$, $Z^{4'}$, $Z^{5'}$, $R^{1'}$, and $R^{3'}$ are $Z^1$, $Z^2$, $Z^3$, $Z^4$, $Z^5$, $R^1$, and $R^3$ are as defined in formula (I) or groups convertible thereto;

$Q^1$ is $NR^{2'}R^{4'}$ or a group convertible thereto wherein $R^{2'}$ and $R^{4'}$ are $R^2$ and $R^4$ as defined in formula (I) or groups convertible thereto and $Q^2$ is H or $R^{3'}$ or $Q^1$ and $Q^2$ together form an optionally protected oxo group;

(i) X is A'-COW, Y is H and n is 0;
(ii) X is $CR^6=CR^8R^9$, Y is H and n is 0;
(iii) X is oxirane, Y is H and n is 0;
(iv) X is N=C=O and Y is H and n is 0;
(v) one of X and Y is $CO_2R^y$ and the other is $CH_2CO_2R^x$;
(vi) X is $CHR^6R^7$ and Y is $C(=O)R^9$;
(vii) X is $CR^7=PR^z{}_3$ and Y is $C(=O)R^9$ and n=1;
(viii) X is $C(=O)R^7$ and Y is $CR^9=PR^z{}_3$ and n=1;
(ix) Y is COW and X is $NHR^{11'}$ or $NR^{11'}COW$ and n=0 or 1 or when n=1 X is COW and Y is $NHR^{11'}$ or $NR^{11'}COW$;
(x) X is $NHR^{11'}$ and Y is $C(=O)R^8$ and n=1;
(xi) X is $NHR^{11'}$ and Y is $CR^8R^9W$ and n=1;
(xii) X is $NR^{11'}COCH_2W$ or $NR^{11'}SO_2CH_2W$ and Y is H and n=0;
(xiii) X is $CR^6R^7SO_2W$ and Y is H and n=0;
(xiv) X is W or OH and Y is $CH_2OH$ and n is 1;
(xv) X is $NHR^{11'}$ and Y is $SO_2W$ or X is $NR^{11'}SO_2W$ and Y is H, and n is 0;
(xvi) X is W and Y is $CONHR^{11'}$;
in which W is a leaving group; $R^x$ and $R^y$ are $(C_{1-6})$alkyl; $R^z$ is aryl or $(C_{1-6})$alkyl; A' and $NR^{11'}$ are A and $NR^{11}$ as defined in formula (I), or groups convertible thereto; and oxirane is:

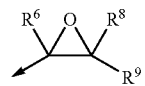

wherein $R^6$, $R^8$ and $R^9$ are as defined in formula (I);
and thereafter optionally or as necessary converting $Q^1$ and $Q^2$ to $NR^2R^4$;
converting A', $Z^{1'}$, $Z^{2'}$, $Z^{3'}$, $Z^{4'}$, $Z^{5'}$, $R^{1'}$, $R^{2'}$, $R^{3'}$, $R^{4'}$ and $NR^{11'}$ to A, $Z^1$, $Z^2$, $Z^3$, $Z^4$, $Z^5$, $R^1$, $R^2$, $R^3$, $R^4$ and $NR^{11}$;
converting A-B to other A-B,
interconverting $R^1$, $R^2$, $R^3$ and/or $R^4$, and/or forming a pharmaceutically acceptable salt and/or N-oxide thereof.

* * * * *